US 11,903,641 B1

(12) United States Patent
Sharma et al.

(10) Patent No.: US 11,903,641 B1
(45) Date of Patent: Feb. 20, 2024

(54) APPARATUS AND TECHNIQUES FOR SURGICAL LASER DELIVERY

(71) Applicant: FemtoVox Incorporated, Ladera Ranch, CA (US)

(72) Inventors: Manu Sharma, Ladera Ranch, CA (US); Wesley William Lummis, Rancho Santa Margarita, CA (US)

(73) Assignee: Femto Vox Incorporated, Ladera Ranch, CA (US)

( * ) Notice: Subject to any disclaimer, the term of this patent is extended or adjusted under 35 U.S.C. 154(b) by 0 days.

(21) Appl. No.: 18/381,941

(22) Filed: Oct. 19, 2023

Related U.S. Application Data

(60) Provisional application No. 63/417,947, filed on Oct. 20, 2022.

(51) Int. Cl.
| | |
|---|---|
| *A61B 18/22* | (2006.01) |
| *A61B 5/00* | (2006.01) |
| *A61B 18/00* | (2006.01) |

(52) U.S. Cl.
CPC ............ *A61B 18/22* (2013.01); *A61B 5/0066* (2013.01); *A61B 2018/00327* (2013.01); *A61B 2018/00607* (2013.01)

(58) Field of Classification Search
CPC .................. A61B 18/22; A61B 5/0066; A61B 2018/00327; A61B 2018/00607
See application file for complete search history.

(56) References Cited

U.S. PATENT DOCUMENTS

| | | |
|---|---|---|
| 5,720,894 A | 2/1998 | Neev et al. |
| 6,717,102 B2 | 4/2004 | Neev et al. |
| 6,839,586 B2 | 1/2005 | Webb |
| 7,131,968 B2 | 11/2006 | Bendett et al. |
| 7,231,122 B2 | 6/2007 | Weisberg et al. |
| 7,583,872 B2 | 9/2009 | Seibel et al. |
| 7,867,224 B2 | 1/2011 | Lukac et al. |
| 8,320,725 B2 | 11/2012 | Temelkuran et al. |
| 8,328,803 B2 | 12/2012 | Regadas |
| 8,636,726 B1 | 1/2014 | Wells et al. |
| 8,685,052 B2 | 4/2014 | Dubois et al. |
| 9,333,036 B2 | 5/2016 | Ben-yakar et al. |
| 10,285,568 B2 | 5/2019 | Tearney et al. |
| 10,588,694 B1 | 3/2020 | Neev |
| 10,821,023 B2 | 11/2020 | Raksi |

(Continued)

OTHER PUBLICATIONS

U.S. Appl. No. 18/381,944, filed Oct. 19, 2023, Apparatus and Techniques for Surgical Laser Delivery.

(Continued)

*Primary Examiner* — Scott Luan
(74) *Attorney, Agent, or Firm* — Schwegman Lundberg & Woessner, P.A.

(57) ABSTRACT

Apparatus and techniques described herein can include delivery of a surgical laser beam for tissue excision or to facilitate hemostasis. The surgical laser beam can be generated, for example, using an ultrafast laser source. Such an approach can provide non-invasive treatment in relation to, for example, aerodigestive anatomy, such as for treatment of laryngeal, oropharyngeal, bronchial, and oral cavity tissues. Other generally available laser sources and their associated treatments may present various drawbacks making them less suitable for treatment for laryngeal, pharyngeal or bronchial pathologies, and use of the apparatus and techniques described herein can address such drawbacks.

30 Claims, 23 Drawing Sheets

(56) References Cited

U.S. PATENT DOCUMENTS

| | | | |
|---|---|---|---|
| 10,821,024 | B2 | 11/2020 | Raksi |
| 11,110,006 | B2 | 9/2021 | Raksi |
| 11,163,324 | B2 | 11/2021 | Swanson et al. |
| 11,172,987 | B2 | 11/2021 | Anderson et al. |
| 11,173,067 | B2 | 11/2021 | Raksi |
| 11,246,754 | B2 | 2/2022 | Holland et al. |
| 11,564,567 | B2 | 1/2023 | Juhasz et al. |
| 2004/0226925 | A1 | 11/2004 | Gu et al. |
| 2009/0225324 | A1 | 9/2009 | Bernstein et al. |
| 2011/0224541 | A1 | 9/2011 | Yun et al. |
| 2020/0078217 | A1 | 3/2020 | Raksi |
| 2020/0078218 | A1 | 3/2020 | Holland et al. |
| 2021/0307964 | A1 | 10/2021 | Holland et al. |

OTHER PUBLICATIONS

Alon, Eran E., et al., "Instrumentation in endoscopic laryngeal surgery", Operative Techniques in Otolaryngology-Head and Neck Surgery vol. 30 Issue 4, (Dec. 2019), 6 pages.

Andrus, Liam, et al., "Scattering properties and femtosecond laser ablation thresholds of human and canine vocal folds at 776-nm wavelength", Journal of Biomedical Optics vol. 24 Issue 8, (Aug. 30, 2019), 8 pages.

Andrus, Liam, et al., "Ultrafast Laser Microlaryngeal Surgery for In Vivo Subepithelial Void Creation in Canine Vocal Folds", The Laryngoscope vol. 133 Issue 11, (Apr. 25, 2023), 7 pages.

Armstrong, Lori R., et al., "Initial Results From the National Registry for Juvenile-Onset Recurrent Respiratory Papillomatosis", Arch Otolaryngol Head Neck Surg/vol. 125, (Jul. 1999), 6 pages.

Armstrong, William B., et al., "Optical Coherence Tomography of Laryngeal Cancer", Laryngoscope 116, (Jul. 2006), 7 pages.

Beck, R. J., et al., "Dynamics of picosecond laser ablation for surgical treatment of colorectal cancer", Scientific Reports vol. 10 Article No. 20261, (Nov. 20, 2020), 10 pages.

Benboujja, Fouzi, et al., "Clinical and surgical implications of intraoperative optical coherence tomography imaging for benign pediatric vocal fold lesions", International Journal of Pediatric Otorhinolaryngology vol. 114, (Nov. 2018), 9 pages.

Benboujja, Fouzi, et al., "Intraoperative imaging of pediatric vocal fold lesions using optical coherence tomography", Journal of Biomedical Optics vol. 21 1, (Jan. 2016), 11 pages.

Benboujja, Fouzi, et al., "Quantitative evaluation of the human vocal fold extracellular matrix using multiphoton microscopy and optical coherence tomography", Scientific Reports vol. 11 Article No. 2440, (Jan. 28, 2021), 16 pages.

Bottcher, Arne, et al., "Reduction of thermocoagulative injury via use of a picosecond infrared laser PIRL in laryngeal tissues", Laryngology vol. 272, (Jan. 2015), 9 pages.

Braun, Andreas, et al., "Heat generation caused by ablation of dental hard tissues with an ultrashort pulse laser USPL system", Lasers in Medical Science 30 2, (May 12, 2013), 7 pages.

Burns, James A., et al., "Imaging the Mucosa of the Human Vocal Fold With Optical Coherence Tomography", The Annals of Otology Rhinology and Laryngology 114 9, (Sep. 1, 2005), 6 pages.

Cantarella, Giovanna, et al., "A High-Definition 3-Dimensional Exoscope With the ARTip Cruise System as an Effective New Tool for Phonosurgery: A Preliminary Report", Journal Voice S0892 1997 21, (Aug. 6, 2021), 4 pages.

Carobbio, Andrea Luigi Camillo, et al., "Transoral laser microsurgery: feasibility of a new exoscopic HD-3D system coupled with free beam or fiber laser", Lasers Med Sci 36 9, (Jan. 3, 2021), 8 pages.

Chauhan, Manish, et al., "Design and modeling of a three-degree-of-freedom articulating robotic microsurgical forceps for trans-oral laser microsurgery", Article in Journal of Medical Devices, (Mar. 2019), 10 pages.

Chen, C Julian, "Electromechanical deflections of piezoelectric tubes with quartered electrodes", Appl Phys Lett vol. 60 Issue 1, (Jan. 6, 1992), 4 pages.

Deshpande, Nikhil, et al., "Design and Study of a Next-Generation Computer-Assisted System for Transoral Laser Microsurgery", OTO Open vol. 2 Issue 2, (May 10, 2018), 10 pages.

Durst, Michael E., et al., "Tunable dispersion compensation by a rotating cylindrical lens", Optics Letters vol. 34 No 8, (Apr. 15, 2009), 3 pages.

Engelbrecht, Christoph J., et al., "Ultra compact fiber optic two photon microscope for functional fluorescence imaging in vivo", Optics Express vol. 16 Issue 8, (Apr. 1, 2008), 9 pages.

Ferhanoglu, Onur, et al., "A 5-mm piezo-scanning fiber device for high speed ultrafast laser microsurgery", Biomedical Optics Express, 5(7), (2014), 14 pages.

Ferlito, Salvatore, et al., "High Definition Three-Dimensional Exoscope Vitom 3D in ENT Surgery A Systematic Review of Current Experience", Journal of Clinical Medicine vol. 11 Iss 13, (Jun. 23, 2022), 20 pages.

Gill, Ruby K., et al., "The effects of laser repetition rate on femtosecond laser ablation of dry bone: a thermal and LIBS study", J Biophotonics 9, (Aug. 11, 2015), 10 pages.

Girard, B., et al., "Effects of Femtosecond Laser Irradiation on Osseous Tissues", Lasers in Surgery and Medicine 39, (Feb. 20, 2007), 13 pages.

Guo, Shuguang, et al., "Office-based optical coherence tomographic imaging of human vocal cords", Journal of Biomedical Optics Letters, 11(3): 30501, (2006), 3 pages.

Hess, Markus, et al., "Picosecond infrared laser PIRL An ideal phonomicrosurgical laser", Laryngology vol. 270, (May 2013), 12 pages.

Higbee, Russell G., et al., "Ultrafast pulsed lasers: surgical wave of the future", Proceedings vol. 5312 Lasers in Surgery Advanced Characterization Therapeutics and Systems XIV, (Jul. 13, 2004), 13 pages.

Hoy, Christopher, et al., "Miniaturized probe for femtosecond laser microsurgery and two-photon imaging", Optics Express 9996, vol. 16, No. 13, (2008), 10 pgs.

Hoy, Christopher L., et al., "Optical design and imaging performance testing of a 9.6-mm diameter femtosecond laser microsurgery probe", Opt Express, vol. 19, No. 11, (2011), 17 pages.

Hoy, Christopher L., et al., "Towards endoscopic ultrafast laser microsurgery of vocal folds", Journal of Biomedical Optics vol. 17 Issue 3, (Mar. 16, 2012), 9 pages.

Ilgner, Justus, et al., "Laser interventionsinotorhinolaryngology-Currenttechniquesand future developments", Medical Laser Application vol. 25, Issue 1, (Feb. 2010), 7 pages.

Im, Kang Bin, "Simple high speed confocal line scanning microscope", Optics Express vol. 13 Issue 13, (Jun. 27, 2005). 6 pages.

Jowett, Nathan, et al., "Heat Generation During Ablation of Porcine Skin With Erbium: YAG Laser vs a Novel Picosecond Infrared Laser", JAMA Otolaryngol Head Neck Surg 139 8, (Aug. 2013), 6 pages.

Kaur, Mandeep, et al., "Scanning and Actuation Techniques for Cantilever-Based Fiber Optic Endoscopic Scanners—A Review", Sensors Basel 21 1, (Jan. 2, 2021), 38 pages.

Kim, Beop Min, et al., "Effects of high repetition rate and beam size on hard tissue damage due to subpicosecond laser pulses", App Phys Lett vol. 76 Issue 26, (Jun. 26, 2000), 4 pages.

Kim, Cheol Hwan, et al., "See Through Type 3D Head Mounted Display Based Surgical Microscope System for Microsurgery:A Feasibility Study", JMIR Mhealth Uhealth 7 3, (Jul. 3, 2019), 13 pages.

Koch, Wayne M., et al., "Treatment of early (stage I and II) head and neck cancer: The larynx", 2021 UpToDate, Inc, (Aug. 5, 2021), 25 pages.

Lanvin, Thomas, et al., "Subsurface ablation of atherosclerotic plaque using ultrafast laser pulses", Biomedical Optics Express vol. 6 Issue 7, (Jan. 7, 2015), 10 pages.

Larson, Daniel A., et al., "Epidemiology of recurrent respiratory papillomatosis", APMIS 118: 450-454, (Jun. 10, 2010), 5 pages.

Lee, Cameron M., et al., "Scanning fiber endoscopy with highly flexible, 1 mm catheterscopes for wide-field, full-color imaging", Journal of Biophotonics, 3(5-6), (2010), pp. 385-407.

(56) References Cited

OTHER PUBLICATIONS

Liang, Kaicheng, et al., "Ultrahigh speed en face OCT capsule for endoscopic imaging". Biomedical Optics Express vol. 6 Issue 4, (Mar. 5, 2015), 18 pages.
Lo, David D., et al., "Femtosecond Plasma Mediated Laser Ablation Has Advantages Over Mechanical Osteotomy of Cranial Bone", Lasers in Surgery and Medicine 44, (Nov. 26, 2012), 10 pages.
Mahlstedt, Kathrin, et al., "An Initial Assessment of the Optical Properties of Human Laryngeal Tissue", ORL 2001 vol. 63 No. 6, (Nov. 1, 2001), 7 pages.
Martin, Chris, et al., "Determination of scattering properties and damage thresholds in tissue using ultrafast laser ablation", Journal of Biomedical Optics vol. 21 Issue 11, (Nov. 30, 2016), 6 pages.
Martin, Chris, et al., "Studying ultrafast laser parameters to deter self-focusing for deep tissue ablation", Proceedings vol. 9740 Frontiers in Ultrafast Optics Biomedical Scientific and Industrial Applications XVI, (Mar. 9, 2016), 8 pages.
Martins, Regina Helena Garcia, et al., "Voice Disorders in Teachers. A Review", Journal of Voice vol. 28 No. 6 2014, (Nov. 2014), 9 pages.
Moon, Sucbei, et al., "Semi-resonant operation of a fiber-cantilever piezotube scanner for stable optical coherence tomography endoscope imaging", Optics Express vol. 18 Issue 20, (Sep. 2010), 15 pages.
Morris, Megan A., et al., "Prevalence and etiologies of adult communication disabilities in the United States: Results from the 2012 National Health Interview Survey", Disability and Health Journal vol. 9, Issue 1, (Jan. 2016), 5 pages.
Nagappan, Shivathmihai, et al., "In Vivo Femtosecond Laser Subsurface Cortical Microtransections Attenuate Acute Rat Focal Seizures", Cerebral Cortex vol. 29 Issue 8, (Aug. 2019), 12 pages.
Neev, Joseph, et al., "Ultrashort Pulse Lasers for Hard Tissue Ablation", IEEE Journal of Selected Topics in Quantum Electronics vol. 2 No. 4, (Dec. 1996), 11 pages.
Niemz, Markolf H., "Laser-Tissue Interactions Fundamentals and Applications", Biological and Medical Physics, Biomedical Engineering, (1996), 316 pages.
Palefsky, Joel M., "Human papillomavirus infections: Epidemiology and diseaseassociations", 2021 UpToDate, Inc., (Dec. 3, 2020), 26 pages.
Petersen, Hannes, et al., "Comparative Study of Wound Healing in Rat Skin Following Incision With a Novel Picosecond Infrared Laser (PIRL) and Different Surgical Modalities", Lasers in Surgery and Medicine 48, (Mar. 4, 2016), 7 pages.
Pike, Pavlina, et al., "Temperature distribution in dental tissue after interaction with femtosecond laser pulses", Appl Opt 46 34, (Dec. 1, 2007), 5 pages.
Qiu, Zhen, et al., "New Endoscopic Imaging Technology Based on MEMS Sensors and Actuators", Micromachines 8 7, (Jul. 2, 2017), 27 pages.
Ridgway, James Matthew, et al., "Imaging of the Pediatric Airway Using Optical Coherence Tomography", The Laryngoscope Dec. 1, 2007 117 12, (Dec. 1, 2007), 7 pages.
Rivera, David R., et al., "Compact and flexible raster scanning multiphoton endoscope capable of imaging unstained tissue", Proceedings of the National Academy of Sciences of the United States of America vol. 108 No. 43, (Oct. 25, 2011), 6 pages.
Rubinstein, Marc, et al., "Transoral laser microsurgery for laryngeal cancer: A primer and review of laser dosimetry", Lasers Med Sci 2011 26, (Sep. 11, 2010), 12 pages.
Sajjadi, Amir Yousef, et al., "Ablation of subsurface tumors using an ultra short pulse laser", Optics and Lasers in Engineering vol. 49 Issue 3, (Mar. 2011), 6 pages.
Seibel, Eric J., et al., "A full-color scanning fiber endoscope", Proceedings vol. 6083, Optical Fibers and Sensors for Medical Diagnostics and Treatment Applications VI, (Feb. 15, 2006), 9 pages.

Sergeev, A. M., et al., "In vivo endoscopic OCT imaging of precancer and cancer states of human mucosa", Optics Express vol. 1 Issue 13, (Dec. 1, 1997), 9 pages.
Shakhov, Andrei, "Capabilities of optical coherence tomography in laryngology", BiOS 99 International Biomedical Optics Symposium, (Jun. 22, 1999), 12 pages.
Shakhov, Andrey V., et al., "Optical Coherence Tomography Monitoring for Laser Surgery of Laryngeal Carcinoma", Journal of Surgical Oncology 77, (Jul. 20, 2001), 6 pages.
Shen, Nan, "Photodisruption in biological tissues using femtosecond laser pulses Part I", ProQuest Dissertations and Theses Harvard University 2003 Publication No. AAI3091684 ISBN 9780496393930 Source: Dissertation Abstracts International vol. 64 05, (Jan. 2003), 100 pages.
Shen, Nan, "Photodisruption in biological tissues using femtosecond laser pulses Part II", ProQuest Dissertations and Theses Harvard University 2003 Publication No. AAI3091684 ISBN 9780496393930 Source Dissertation Abstracts International vol. 64 05, (Jan. 2003), 35 pages.
Smithwick, Quinn Y. J., et al., "A Nonlinear State-Space Model of a Resonating Single Fiber Scanner for Tracking Control: Theory and Experiment", J Dyn Sys Meas Control 126 1, (Mar. 2004), 14 pages.
Strong, M. Stuart, "Laser Surgery in the Larynx: Early Clinical Experience With Continuous CO2 Laser", Ann Otol Rhinol Laryngol USA Da vol. 81 NO 6, (1972), 8 pages.
Su, Jianping, et al., "Real time swept source optical coherence tomography imaging of the human airway using a microelectromechanical system endoscope and digital signal processor", Journal of Biomedical Optics vol. 13 3, (May 1, 2008), 3 pages.
Subramanian, Kaushik, et al., "Kagome fiber based ultrafast laser microsurgery probe delivering micro-Joule pulse energies", Biomed Optics Express, 7(11), (2016), pp. 4639-4653.
Subramanian, Kaushik Gurunthan, "Ultrafast laser microsurgery: Strategies for improving endoscopic bulk tissue ablation and cellular microsurgery", [Online]. Retrieved from the Internet: < https://repositories.lib.utexas.edu/handle/2152/85296>, (Dec. 2018), 189 pages.
Weber, Dieter, et al., "First Results with Ablating Superficial Cell Layers of the Porcine Vocal Fold Using a Femtosecond Laser", Medical Laser Application vol. 18 Issue 3, (Sep. 2003), 5 pages.
Wisweh, Henning, et al., "Optical coherence tomography monitoring of vocal fold femtosecond laser microsurgery", SPIE OSA vol. 6632, (Jun. 2007), 7 pages.
Wong, Brian J. F., et al., "In Vivo Optical Coherence Tomography of the Human Larynx: Normative and Benign Pathology in 82 Patients", The Laryngoscope, 115(11), (2005), pp. 1904-1911.
Xi, Jiefeng, et al., "Integrated multimodal endomicroscopy platform for simultaneous en face optical coherence and two-photon fluorescence imaging", Optics Letters vol. 37 No 3. (Feb. 1, 2012), 3 pages.
Yakovlev, Evgeny, et al., "Modelling of the heat accumulation process during short and ultrashort pulsed laser irradiation of bone tissue", Biomedical Optics Express vol. 10 No. 6, (Jun. 1, 2019), 11 pages.
Yan, Yan, et al., "Use of Lasers in Laryngeal Surgery", J Voice Jan. 2, 20104 1, (Jan. 2010), 19 pages.
Yildirim, Murat, "Nonlinear Imaging Assisted Ultrafast Laser Microsurgery for the Treatment of Vocal Fold Scarring", [Online]. Retrieved from the Internet: <https://repositories.lib.utexas.edu/handle/2152/31548>, (Aug. 2015), 164 pages.
Yildirim, Murat, et al., "Parameters affecting ultrafast laser microsurgery of subepithelial voids for scar treatment in vocal folds", Journal of Biomedical Optics, 1811), (2013), 14 pages.
Yu, Lingfeng, et al., "Office based dynamic imaging of vocal cords in awake patients with swept source optical coherence tomography", Journal of Biomedical Optics 14 6, (Nov. 1, 2009).
Zhang, Yuying, et al., "A compact fiber-optic SHG scanning endomicroscope and its application to visualize cervical remodeling during pregnancy", PNAS vol. 109 No. 32, (Aug. 7, 2012), 6 pages.

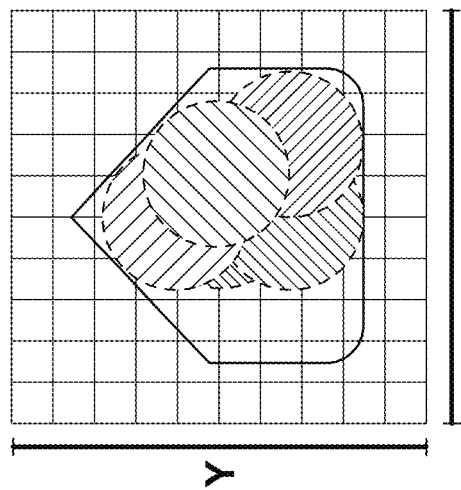
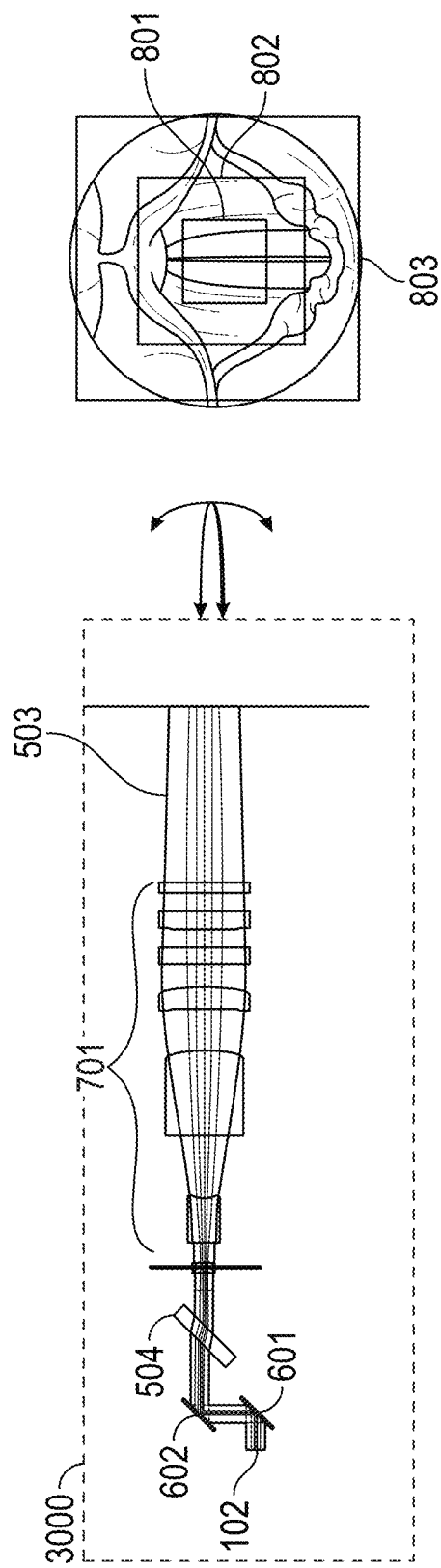
FIG. 8A
FIG. 8B

Pitch

Yaw

APPARATUS AND TECHNIQUES FOR SURGICAL LASER DELIVERY

CLAIM OF PRIORITY

This patent application claims the benefit of priority of Sharma et al., U.S. Provisional Patent Application No. 63/417,947, titled "APPARATUS AND TECHNIQUES FOR LASER SURGERY," filed on Oct. 20, 2022, which is hereby incorporated by reference herein in its entirety.

FIELD OF THE DISCLOSURE

This document pertains generally, but not by way of limitation, to controlling and delivering a surgical laser beam, and more particularly, to performing delivery of a surgical laser beam to tissue for tissue excision or to facilitate hemostasis, the surgical laser beam generated, for example, using an ultrafast laser source.

BACKGROUND

By way of introduction, the following discussion provides context in reference to human anatomy, with emphasis on certain regions of the aerodigestive anatomy, starting with the anatomy of the larynx:

FIG. 1A illustrates generally a section view of human anatomy showing a portion of the aerodigestive tract including a pharyngeal region, and FIG. 1B illustrates generally a view of human anatomy comprising a larynx including vocal cords. With reference to FIG. 1A and FIG. 1B, the location of the larynx 1 is at the C3 to C7 vertebrae and situated just below where the pharynx 3 splits into respiratory (trachea 4) and digestive (esophagus 5) functions. It has a triangular shape, suspended in position via attachments to the hyoid bone 6, and is generally 4 centimeters (cm) to 5 cm in length and width. The epiglottis 7 prevents food and water from entering the respiratory tract. Minimally invasive mechanical or optical access to the larynx is achieved through the oral cavity 2, also known as "trans-oral" access.

FIG. 2 illustrates generally a section view of human anatomy showing different laryngeal regions. With reference to FIG. 2, the larynx is sub-divided into three anatomic regions; the supraglottis 22, glottis 23, and subglottis 24. The supraglottis 22 comprises the epiglottis 25 and false cords 26, the glottis 23 are the true vocal cords 27 and the space between them and the subglottis 24 is the region below the vocal cords extending to the trachea 28. The larynx 1 comprises cartilaginous skeleton 29, extrinsic and intrinsic muscles 30, and mucosal lining. Larynx 1 functions include protection of the lungs from food and water aspiration, phonation, respiration, and swallowing. The larynx 1 protects the lower respiratory tract from aspirated food during swallowing via deflection of the epiglottis 25, respiratory inhibition and closure of the vocal folds. Phonation occurs at the level of the vocal cords 27.

Vocal Cords

The glottis 23 can be anatomically divided into anterior and posterior regions. The anterior region is most responsible for voice production, or phonation. The vocal folds act as a converter of aerodynamic energy generated by the chest, diaphragm, and abdominal musculature into acoustic energy. This conversion occurs primarily in the space between the vocal folds, which create acoustic resonance. Vocal fold vibration is crucial for voice production. Ideal vibration requires edges that close evenly and high pliability. Therefore, any damage or lesions on the vocal folds can cause voice changes, pain, and vocal fatigue.

FIG. 3A illustrates generally a section view of human anatomy showing different tissue structures that can form a vocal fold region, and FIG. 3B illustrates generally a view of human anatomy showing different tissue structures associated with a squamous epithelium and associated mucociliary blanket. With reference to FIG. 3A, at the gross anatomy level, the vocal folds comprise stratified squamous epithelium 31; three layers of the lamina propria, superficial 32A, intermediate 32B, and deep 32C; thyroarytenoid muscle 33; and fibrous ligament 34. They are actuated primarily by the lateral cricoarytenoid, thyroarytenoid, and interarytenoid muscles, which together accomplish vocal fold adduction (closing), and the posterior cricoarytenoid muscles, which by itself achieves abducts (opening). The epithelium, lamina propria, and muscle are known as the "cover," "transition," and "body" respectively. For phonation, the lamina propria and epithelium are of interest, because phonation pathologies due to musculature dysfunction generally have neurological etiology.

The squamous epithelium is very thin, on the order of 5-20 cells deep, and is the primary location of laryngeal cancers. Referring to FIG. 3B and FIG. 2, a layer of mucus, the mucociliary blanket 35, lies over the epidermis. The mucosal blanket is a circulatory layer, propelled up the trachea by the cilia 36, and its movement constantly replenishes and lubricates the vocal folds to prevent dehydration and protect underlying structures. Pathologies can arise if the blanket motion is impaired as the mucus. For example, smoking, which introduces particulates 37 into the larynx, reduces the clearance rate of the blanket. The epidermis is secured to the lamina propria 32 through the basement membrane zone (BMZ) 38. The BMZ comprises different collagen types. The attachments must be strong to resist the vibrational forces of the bulk vocal cord movement.

With further reference to FIG. 3A, the lamina propria (LP) is sub-divided into three sections: superficial 32A, intermediate 32B, and deep 32C. The LP is approximately 300-500 um thick, of which the superficial layer is approximately 20% of its thickness. The LP comprises cells and macrophages that respond to and may cause inflammation, and myofibroblasts, which are responsible for repair. The presence of myofibroblasts indicates that the vocal folds undergo microscopic trauma in need of constant repair and is supported by clinical evidence that acute vocal overuse heals within 2-3 days. Furthermore, the presence of macrophages show the LP to be vulnerable to an inflammatory response provoked by trauma, such as during surgery. With the lowest concentration of fibrous matrix, the superficial layer has the least resistance to vibration and is the most critical for proper phonation. Within increasing tissue depth, the intermediate and deep layers comprise increasing collagen concentration. The primary mass of the vocal folds comes from the thyroarytenoid muscle. Tissue changes drive vocal fold pathology. One aspect of any surgery is to preserve laryngeal function, including swallowing ability, airway protection and voice quality.

SUMMARY OF THE DISCLOSURE

The present inventors have recognized, among other things, that approaches described herein such as including use of ultrafast surgical laser delivery can facilitate laser-based surgery, such as to modify (e.g., excise) tissue while suppressing thermal trauma, collateral damage, or associated sequelae. For example, as shown and described herein, the present inventors, among other things, have developed apparatus and techniques facilitating delivery of a surgical laser beam for tissue excision or to facilitate hemostasis. According to various examples herein, the surgical laser beam can be generated, for example, using a femtosecond or picosecond laser source. The apparatus and techniques described herein are believed applicable to non-invasive treatment in relation to aerodigestive anatomy, such as for treatment of laryngeal, oropharyngeal, bronchial, and oral cavity tissues, as illustrative examples. By contrast with the techniques and related apparatus described herein, other generally available laser sources and their associated treatments may present various drawbacks making them less suitable (or even unsuitable) for treatment for laryngeal, pharyngeal or bronchial pathologies, and use of the apparatus and techniques described herein can address such drawbacks.

In an example, a system (or corresponding method) can provide depth-selective laser beam delivery. For example, a scanning assembly can co-scan respective beams in two axes, the respective beams comprising a surgical laser beam comprising monochromatic coherent pulsed light, an optical coherence tomography (OCT) beam comprising incoherent polychromatic light or coherent laser light having a varying wavelength, and a visible aiming beam. An optical system can controllably co-focus the respective beams including at least two visible aiming beam portions, including directing the at least two visible aiming beam portions trans-orally toward a tissue surface and conveying reflections of the visible aiming beam portions to a visualization imager. A control system can generate a presentation of a visible-light visualization of a tissue surface and the reflections of the visible aiming beam portions received by the visualization imager, acquire focus on the tissue surface as indicated by the respective visible aiming beam portions spatially converging in the generated presentation, by varying a focus of the optical system, and track motion in two axes using a visible feature in an in-focus generated presentation, for control of the scanning assembly.

In an example, a system (or corresponding method) can provide depth-selective laser beam delivery. A scanning assembly can co-scan respective beams in two axes to define a first addressable region, the respective beams comprising a surgical laser beam comprising monochromatic coherent pulsed light, and an optical coherence tomography (OCT) beam comprising incoherent polychromatic light or coherent laser light having a varying wavelength. An optical system can controllably co-focus the respective beams in a depth-selective manner. A movable platform comprising electrically-operated actuators can adjust an orientation of the scanning assembly and optical system to move the first addressable region within a larger second addressable region. A control system can control the movable platform using the electrically-operated actuators platform to align the first addressable region with a tissue region of interest and generate control data for actuating the optical system to direct the respective beams trans-orally including focusing the surgical laser beam at respective focal planes corresponding to different depths, and at respective depths, actuating the scanning assembly to scan the surgical laser beam across a specified two-dimensional treatment area to excise tissue using at least one of plasma-induced ablation or photodisruption.

In an example, a system (or corresponding method) can provide depth-selective surgical laser beam delivery. A scanning assembly can co-scan respective beams in two axes, the respective beams comprising a surgical laser beam comprising monochromatic coherent pulsed light, an optical coherence tomography (OCT) beam comprising incoherent polychromatic light or coherent laser light having a varying wavelength. An optical system can controllably co-focus the respective beams in a depth-selective manner. An ultrafast surgical laser source can generate the surgical laser beam to modify a volume of tissue by excision or facilitating hemostasis, or both, and a control system communicatively coupled with the scanning assembly, the optical system, and the ultrafast surgical laser source, can establish at least one characteristic of a focused pulse or focused pulses of the surgical laser beam as delivered to a tissue site to selectively enhance hemostasis.

In an example, a system (or corresponding method) can provide surgical laser beam delivery using an optical fiber. An ultrafast surgical laser source can generate a surgical laser beam for excising tissue, facilitating hemostasis, or both. An optical fiber coupled to the ultrafast surgical laser source can deliver and focus light spanning at least a wavelength of the surgical laser beam, including delivering monochromatic coherent pulsed light of the surgical laser beam, comprising ultrafast pulses defined by a duration ranging from 10 femtoseconds to 300 picoseconds (or defined by another specified range), to a tissue site. A scanning assembly can scan the light in a two-dimensional pattern, and a control system communicatively coupled with the scanning assembly and the ultrafast surgical laser source, can establish at least one characteristic of a focused pulse or focused pulses of the surgical laser beam as delivered to the tissue site by the optical fiber, to selectively enhance hemostasis.

In an example, a system (or corresponding method) can provide depth-selective surgical laser beam delivery. A scanning assembly can co-scan respective beams in two axes, the respective beams comprising a surgical laser beam comprising monochromatic coherent pulsed light, an optical coherence tomography (OCT) beam comprising incoherent polychromatic light or coherent laser light having a varying wavelength. An optical system can controllably co-focus the respective beams and supporting visible light visualization. A control system can generate a presentation of a visible-light visualization of a tissue surface, receive an input defining a two-dimensional treatment area, in response to a presentation of a visible-light visualization of the tissue surface, generate a presentation of a cross-sectional representation of a region below the tissue surface, the cross-sectional representation constructed using a scattered representation of the OCT beam conveyed by the optical system, receive an input defining a depth range for treatment by the surgical laser beam, in response to the presentation of the cross-sectional representation of the region below the tissue surface, and generate control data defining cycles to modify and visualize tissue within a volume defined by the two-dimensional treatment area and the depth range, by actuating the optical system to focus on respective focal planes corresponding to different depths, and at respective depths, actuating the scanning assembly to scan the surgical laser beam and OCT beam across the two-dimensional area including delivering the surgical laser beam and OCT beam trans-orally.

In an example, a system (or corresponding method) can provide depth-selective surgical laser beam delivery. A scanning assembly can scan a surgical laser beam in two axes. An optical system configured can focus the surgical laser beam in a depth-selective manner, the optical system comprising an objective to convey the surgical laser beam to a treatment site and supporting visible light visualization by establishing at least two distinct visible light visualization optical pathways from the treatment site to respective visualization imagers to provide respective visualization perspectives. An ultrafast surgical laser source can generate the surgical laser beam for excising tissue, facilitating hemostasis, or both.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8A illustrates generally an example comprising an optical system, such as can be positioned using a movable platform.

FIG. 8B illustrates generally an example comprising various different regions that can be addressed within a cross-sectional area of an elongate instrument, such as using the optical system of FIG. 8A.

FIG. 1 shows an illustrative example of respective visual presentations that can be used to provide image-guided laser surgery, such as including acquiring focus to visualize a tissue surface and establishing a two-dimensional treatment area.

DETAILED DESCRIPTION

Figure 1A:
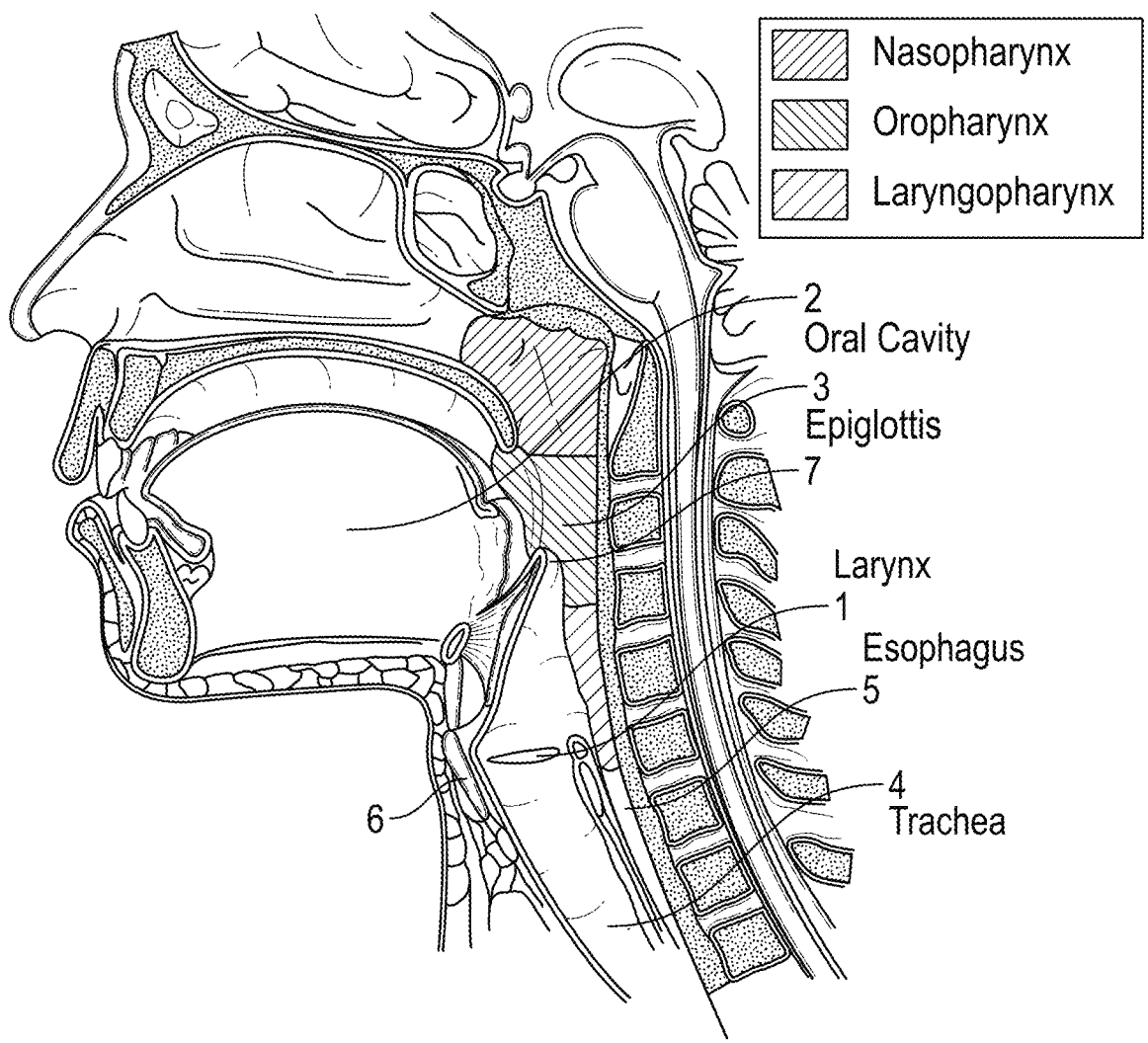
FIG. 1A illustrates generally a section view of human anatomy showing a portion of the aerodigestive tract including a pharyngeal region.
Figure 1B:
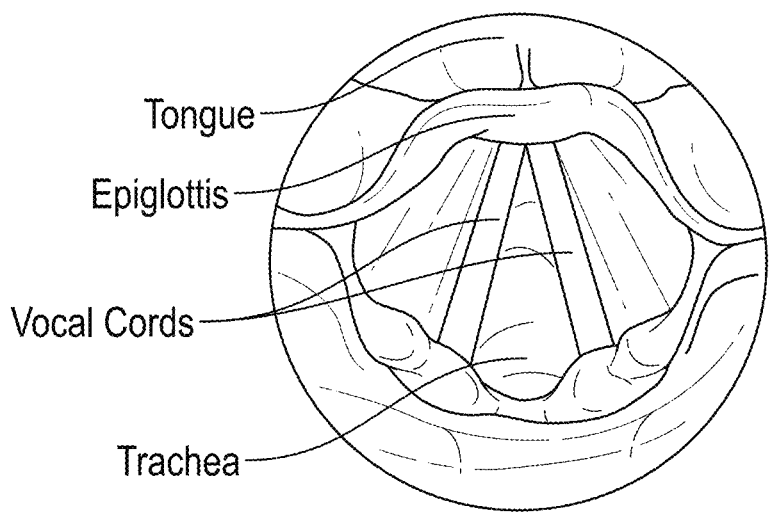
FIG. 1B illustrates generally a view of human anatomy comprising a larynx including vocal cords.

Aspects of the present subject matter can include treatment of tissue located on or within a portion of the aerodigestive anatomy. As an illustrative but non-limiting example, such treatment can include delivery of a surgical laser beam to a pharyngeal region. By way of illustration, anatomy of the pharynx relevant to such treatment can include the oropharynx and laryngopharynx sub-divisions. The oropharynx is the middle division of the pharynx, and includes the tonsillar area, tongue base, soft palate, and posterior pharyngeal wall. The hypopharynx is the lower division of the pharynx, and includes the pyriform sinuses, the posterior surface of the larynx (post-cricoid area), and the inferoposterior and inferolateral pharyngeal walls. In particular, aspects of the present subject matter can include use of a surgical laser, such as a femtosecond or picosecond laser source, to treat benign pathologies of the larynx such as polyps, cysts, nodules, granulomas, recurring respiratory papillomatoses (RRP), or Reinke's edema, which cause vocal cord dysfunction and chronic voice impairment (dysphonia); early-stage tongue, pharynx and larynx cancer; and airway repair after mechanical ventilation (MV) injury for COVID-19, and other respiratory critical-care, survivors. Voice use may be critical for 25% of jobs (e.g., teachers, singers, sales), as an illustrative example: 3% (police, pilot) are mandated for public safety. The prevalence of benign lesions in teachers is 21 times greater than the general population. Pharynx, larynx, and tongue cancer comprise 4.4% of new US cancer cases and 2.9% of deaths, according to presently-available data.

Laryngeal Cancer

In 2021, there are approximately 96.000 Americans with laryngeal cancer, 13,000 new laryngeal cancer diagnoses and 4,000 deaths. Approximately worldwide there are 180,000 cases and 100,000 deaths annually. Most laryngeal cancers originate in the squamous cell layer (~95%) and occur in the glottis (~70%). Current treatment for glottic T1 and T2 carcinoma can include $CO_2$ surgery, radiation therapy, or trans-oral robotic surgery, as examples. However, controversy exists for which therapy modality has superior phonation outcomes. In terms of outcomes, such as hoarseness, voice perturbation, pain and vocal fatigue, some studies report better outcomes for radiation therapy over laser, others favor lasers over radiation, and yet others still report no statistical difference.

Recurrent Respiratory Papillomatosis, or RRP

Recurrent respiratory papillomatosis is a disease associated with various types of human papillomavirus (HPV) and is characterized by persistent, multiple papillomas on the larynx. Although RRP is benign, it causes significant morbidity due to warts on the vocal cords inhibiting larynx function with clinical presentation of voice changes, difficulty breathing, and stridor. In rare instances, lesions can turn malignant and spread to the lungs. While onset can happen in adulthood, RRP first manifests most frequently in childhood. RRP is the most common benign pediatric laryngeal tumor, with epidemiological studies indicating a socioeconomic correlation, with an incidence of 4.3 per 100,000 children younger than 14 years. Presently, there is no cure, and the economic cost is steep: on average, a child with RRP requires 20 procedures over their lifetime; one-in-five children with aggressive disease require more than 40 procedures in their lifetime. Approximately, 15,000 surgeries are performed annually on children and adults every year.

Vocal Cord Nodules and Polyps

Generally, nodules and polyps occur due to chronic vocal fold irritation and studies have demonstrated pathologic changes occur in the superficial lamina propria. Vocal fold nodules are typically bilateral, occurring at the junction of the anterior and middle third of the vocal fold and have an opaque to white appearance, and are firm. In contrast, polyps are typically unilateral and have a translucent to red appearance.

Symptoms of both polyps and nodules include hoarseness, discomfort, or pain. The result is fluctuating phonation, which impacts quality of life and has pronounced consequences for professional voice users whose financial security and self-worth is tied to their voice, such as singers, actors, and theater performers; high profile public speakers, news reporters, and social media influencers; and clergy, teachers, and salespersons. In total, based on national epidemiological data, approximately 460,000 Americans have been diagnosed with vocal cord polyps or nodules; true numbers will be much higher as 10% of Americans report communication disabilities, but only 2% are diagnosed. Vocal cord nodules are treated conservatively by speech therapy, or with surgery. Surgical removal can be performed with cold instruments or using a laser. Data were compiled from the 2019 NASS and CMS databases, covering all Medicare in-office visits and 15.7M outpatient surgeries performed in the US. For larynx, pharynx and select bronchial CPT codes with ultrafast laser surgery potential, such data indicated 28919, 34970, and 29700 procedures in the office, outpatient, and inpatient settings respectively.

Laryngeal Laser Tissue Interactions

Laser types used for laryngeal surgery include the carbon dioxide laser ($CO_2$), Potassium Titanyl Phosphate (KTP), Thulium Yttrium-Aluminum-Garnet (Tm:YAG), Holmium: YAG (Ho:YAG), diode lasers, "TruBlue" and Pulsed Dye Laser (PDL). Trans-oral laser microsurgery, or TLM, generally refers to the use of such lasers for the treatment of any of the aforementioned pathologies. TLM can be used selectively depending upon surgeon preference, cancer staging, or disease presentation. Laser systems for otolaryngology soft tissue applications are commercially available from Boston Scientific (Marlborough, MA, USA), Convergent Laser Technologies (Alameda, CA, USA). OmniGuide (Cambridge, MA, USA), and Jena Surgical (Jena, Germany). These lasers are used to treat a variety of pathologies such as: stenoses, RRP, malignant laryngeal disease leukoplakia/dysplasia, Reinke's edema, vocal cord nodules and polyps, and granulomas. The $CO_2$ and Thulium laser wavelengths correspond to intense water absorption, while the KTP, TruBlue and PDL target hemoglobin. The present inventors have recognized, among other things, that use of the above-mentioned lasers can lead to interaction mechanisms that present challenges.

The present inventors have also recognized that inducing different levels of tissue heating can cause hemostasis (e.g., via coagulation), vaporization, carbonization, or melting depending on laser parameters such as pulsed or continuous operation, exposure time, fluence, pulse duration, power, and repetition rate. With repeated laser pulses striking the tissue, light energy is absorbed by the tissue and converted to heat energy. At 60 C, coagulation occurs and at 100 C vaporization and cutting generally occur. $CO_2$, Tm:YAG, Ho:YAG, TruBlue, and KTP lasers induce a thermal interaction with biological tissue, where an increase in local temperature is the significant parameter change resulting from application of the laser. Heating occurs due to absorption of water for the $CO_2$, Tm:YAG, and Ho:YAG lasers; the KTP and TruBlue lasers correspond to an absorption band of hemoglobin.

A fundamental, unavoidable consequence of the photothermal interaction of the above-mentioned lasers is collateral damage and inflammatory response due to heat dissipation outside the intended treatment zone. For example, in a laryngeal application, such heat dissipation can cause trauma to the delicate subepithelial structure (lamina propria) of the vocal cords. The pulse durations of the above-mentioned lasers—on the order of microseconds to one minute—is much longer than the timescale for heat to dissipate into adjacent tissue without a significant temperature rise, regardless of the laser wavelength or any other laser parameter. Photothermal effects can lead to fibrosis, reducing vocal fold pliability, which can lead to phonation problems such as hoarseness, pain, and vocal fatigue.

Because water is omnipresent in laryngeal tissues, the $CO_2$, Tm:YAG, and Ho:YAG lasers are not selective of tissue and cell morphology and can cause spatially indiscriminate thermal damage. For example, if a lesion is treated with any photothermal laser then the photothermalized area will almost invariably be larger than the desired treatment location. As an illustrative example, a measured extent adjacent tissue injury can be 0.4 mm to 1 mm for photothermal lasers (where, by contrast, ultrafast laser techniques as described herein can restrict such adjacent tissue heating to within about 0.05 mm, as an illustrative but non-limiting example). Adjacent tissue damage can be a particular challenge presented by use of a $CO_2$ laser because the SLP—as discussed above—is the most critical for phonation, yet this structure is also highly sensitive to damage and will be affected regardless of lesion location above or below the SLP. Non-localized trauma to areas critical for phonation can also occur for any cold surgery procedure, even if not performed with laser.

The KTP and TruBlue lasers have higher specificity as compared to the $CO_2$ laser because photothermal heating only occurs for vascularized areas. However, cutting vascularized tissue requires increasing local temperatures above 100 C, which still results in heat dissipation, and therefore collateral damage, to adjacent tissues. Generally available techniques (not using the ultrafast laser source as described herein) can cause trauma to the delicate vocal folds. By way of illustration, 20% of surgeries have complications, including 10% with major complications: 30% of nodule surgeries result permanent dysphonia; and 27% of office-based laser procedures require re-treatment. Complication rates and speech therapy failures are exacerbated by geographical, socio-economic, and racial disparities: otolaryngologic surgeries (out of 29 specialties) have some of the worst racial disparities and post-surgery speech pathology non-completion is 1.5× more likely for non-whites; compared to private insurance patients, larynx cancer was 7× and 2.5× more likely for Medicaid and Medicare patients; and laryngeal cancer incidence rates are 5.3× higher in rural areas than urban despite 4× lower specialist supply.

The intense photothermal effect of the $CO_2$ laser can present additional challenges such as risk of burning the patient or operative team. The $CO_2$ laser is the primary source of operating room fire. Precautions include: facial skin protection, special drapes to cover the patient, use of a smoke evacuator (and associated structure such as rigid tubular members) to remove gases associated with the laser plume, and a specially designed endotracheal tube to suppress ignition due to laser burning.

None of the generally available lasers mentioned above, and their associated treatments, are necessarily particularly suitable for treatment for laryngeal, pharyngeal or bronchial pathologies. Accordingly, the present inventors have recognized that apparatuses and methods for laser aerodigestive surgery are needed such as to effectively treat and excise tissue without thermal trauma, collateral damage, or associated sequelae. The present inventors, among other things, have developed apparatus and techniques facilitating delivery of a surgical laser beam, and more particularly, to performing depth-selective delivery of a surgical laser beam to tissue for tissue excision or to facilitate hemostasis, or both. According to various examples herein, the surgical laser beam can be generated, for example, using a femtosecond or picosecond laser source. The apparatus and techniques described herein are believed applicable to non-invasive treatment of laryngeal, oropharyngeal, bronchial and oral cavity tissues, as illustrative (but non-limiting) examples.

Ultrafast Laser Source

Generally, the examples described herein can include or can be coupled to an ultrafast pulsed laser energy source (e.g., less than 500 picosecond pulse duration, or generally less than about 1 picosecond pulse duration), such as including a femtosecond or picosecond laser. In an example, the ultrafast pulsed laser energy source can generate ultrafast pulses defined by having a duration from a range of 10 femtoseconds to 300 picoseconds. By contrast with other laser sources, an ultrafast laser generally processes tissue via optical breakdown, which causes no thermally induced collateral damage. Optical breakdown is a non-linear multi-photon process that occurs for power densities exceeding $10^{11}$ $W/cm^2$ in solids (~$10^{14}$ $W/cm^2$ in air). Optical breakdown has two physical effects: plasma generation and shockwave generation. For fluences <50 joules per square centimeter ($J/cm^2$), plasma generation occurs, and tissue is primarily removed through ionization and termed plasma-induced ablation; above 50 $J/cm^2$, mechanical forces become significant, and tissue is removed through both ionization and cavitation and such behavior can be referred to as "photodisruption."

It has been empirically determined that the plasma-induced fluence threshold—the value at which optical breakdown is initiated—is roughly proportional to a square root of a pulse duration. Therefore, with all other factors being equal such as optical performance, ultrafast laser excision initiation will occur at laser pulse energies at lower pulse durations. For laser pulses greater than approximately 500 picoseconds (ps) in duration, including all generally-available laryngeal surgical lasers, the time for excited electrons to decay to a lower energy state—the relaxation time—is faster than the pulse time and so electrons can "offload" their energy to different forms, such as heat. However, for an ultrafast laser pulse, this energy transfer is inhibited. Instead, a few initially quasi-free electrons, produced by multi-photon absorption, ionization of tissue molecules (e.g., collagen, hemoglobin, water) or defect sites, due to the very high-power densities, absorb laser photons and accelerate to kinetic energies greater than the band gap energy of the targeted tissue. When a free electron collides with an atom it then causes ionization of the atom, stripping it of two electrons. These free electrons then repeat the process of photon absorption, acceleration, and collisional ionization. This precipitates a collisional avalanche of free electrons, generating plasma and vaporization of the tissue. Plasma is generally confined to the focal region of the laser beam and non-focal regions where the beam traverses are not generally affected, unlike other approaches. As an illustrative, but non-limiting example, a focal spot is typically 5-70 micrometers in diameter and material is only disrupted in this small region. Therefore, ultrafast lasers process tissue with very high spatial and thermal confinement. Ultrafast laser optical breakdown has a "damage zone" several orders of magnitude less than lasers with longer pulses, such as the $CO_2$ and KTP lasers. For example, during excision where an ultrafast laser source is used, studies measured only a 0.2-2.5 C increase in hard and soft tissues.

Overall, the present inventors have recognized, among other things, that existing photothermal-based lasers, such as $CO_2$ and KTP, can be supplanted with a photodisruptive or plasma-induced ablative ultrafast laser to improve clinical outcomes and usability, including otherwise retaining generalized benefits of lasers for aerodigestive surgery, such as being minimally invasive with no radiation. Challenges presented by generally available non-ultrafast laser treatment do not exist due to the fundamentally different laser-tissue mechanism resulting from operation of the ultrafast laser: suppression of collateral damage and adjacent tissue trauma with associated improved wound healing; high spatial precision as excision (e.g., cutting) only occurs at the focus of the laser; and reduction (or even elimination) of any risk of burning and associated precautionary complications of photothermal TLM.

The system shown in various examples herein can include or can be coupled with a laser source to deliver ultrafast laser pulses, such as having a pulse duration from 10 femtoseconds (fs) to 500 picosecond (ps) and with a wavelength from a range of 700 nanometers (nm) to 3100 nm. Commercially available ultrafast lasers with these parameters are manufactured by several vendors, including (but not limited to) Spectra Physics (Irvine, CA), Coherent (Santa Clara, CA), NKT (Birkerod, Denmark), IPG (Oxford, MA), Light Conversion (Vilnius. Lithuania), Ekspla (Vilnius. Lithuania), and Amplitude Laser Systems (Pessac, France). Other pulse durations corresponding to ultrafast surgical laser use can include a duration from a range of 1 femtosecond to 1 nanosecond, or from 10 femtoseconds to 300 picoseconds, as illustrative examples.

Visualization System

The systems shown in various examples herein can include visualization capabilities providing a surgeon with real-time video for observation, diagnosis, and ultrafast laser surgical planning. For example, a visualization system can be configured to provide a clinically appropriate view of larynx, and adjacent anatomy such as, but not limited to, the tongue root, epiglottis, vocal fold, trachea and esophagus. As a tool for surgical planning, the optical characteristics can be constrained for suitability for such planning in terms of magnification and field-of-view, spatial resolution, and depth-of-field.

Optical Coherence Tomography (OCT)

The systems shown in various examples herein can include an OCT capability. OCT is an interference-based technique that involves scanning the focus of a broadband light source across a sample of interest, such as to construct high-resolution two-dimensional cross-sectional images. Photons that penetrate the sample and backscatter return with a different phase (due to the optical path difference) than photons in a reference path; photons that travel deeper have longer optical path differences. In one approach, using mathematical processes, including Fourier transforms, this optical path difference can be converted into depth information and subsequently a cross-sectional image. An OCT beam is non-ionizing and low power, thereby posing no safety risks for use in the oral cavity, pharynx, trachea, or larynx.

Illustrative examples of OCT include: spectral domain (SD-OCT) or swept source (SS-OCT). SD-OCT involves signal processing of the backscattered source OCT spectrum as the original source spectrum is modulated by interaction with tissue, while the reference spectrum has no such modulation. As such, SD-OCT uses a spectrometer. SS-OCT uses a source that sweeps through a wavelength range and the signal is processed in discrete "batches" or "buckets" corresponding to different wavelength ranges. Generally, either of these two techniques can be used in relation to the examples herein. Specialized individual components, such as spectrometers and light sources, are available from various vendors including Santec (Aichi, Japan), Exalos AG (Schlieren, Switzerland), Teledyne e2v (Chelmsford, UK), and Wasatch Photonics (Morrisville, NC). Turnkey OCT systems are available from vendors such as Thorlabs (Newton, NJ. USA), Carl Zeiss Meditec AG (Oberkochen, Germany), and Heidelberg (Franklin, MA). The axial resolution of an OCT system is generally a function of the source bandwidth and center wavelength. Axial spatial resolution below 5 micrometers ($\mu$m) is possible with both SD-OCT and SS-OCT configurations, as an illustrative example.

OCT, Ultrafast Laser, and Aiming Beam

Generally available photothermal laser surgery techniques, such as involving $CO_2$ and KTP lasers, are depth indiscriminate and tissue can be destroyed at depths beyond and above a targeted lesion. This can be due to multiple reasons. Firstly, photothermal tissue processing relies upon light absorption of endogenous molecules (e.g., water or hemoglobin) that are distributed throughout all tissues. Secondly, the focused laser spots of $CO_2$ and KTP lasers are large by comparison to the spot size associated with the ultrafast laser techniques described herein. For example, a spot size associated with $CO_2$ or KTP can be on the order of 200 $\mu$m to 1000 $\mu$m. In contrast, the ultrafast laser spot is on the order of 5 $\mu$m to 70 $\mu$m. Accordingly, the optical breakdown mechanism is a non-linear, hyper-localized phenomena. Thirdly, generally available lasers are only guided by visible light visualization systems which provide only superficial information, and no depth information.

The ultrafast laser is generally a near infrared light source and cannot be seen on a visible imaging system. Even if a visible-NIR detector was used, the ultrafast laser power is orders of magnitude larger than the visible light forming the image and would therefore render the image useless (e.g., because imaging settings suitable to visualize the surgical beam would preclude visualization of tissue and vice versa). Accordingly, where the user cannot directly view the ultrafast laser location, an indirect method can be used. For example, a visible "aiming beam" can be used as a range finding tool to indicate where a surface of the tissue lies. The aiming beam can be implemented using an economical, compact, and monochromatic source such as a diode laser chip mounted on custom mechanicals, or off-the-shelf fiber-coupled or free-space "plug and play" unit. Components that can be used for aiming beam implementation are available from distributors or OEM vendors such as Digikey (Thief River Falls, MN), Thorlabs (Newton, NJ. USA), Edmund Optics (Barrington, NJ, USA), Newport (Irvine, CA, USA) or Hamamatsu (Hamamatsu City, Japan).

The aiming beam can serve as a coarse locator of a surgical treatment location however it is generally indicating a location on the tissue surface alone. The present inventors have recognized, among other things, that cross-sectional OCT images can provide surgeons with depth information and spatial control, such as focus control and scanning, to target a location in tissue, such as encompassing a specified depth or region of depths within tissue. Accordingly, the present inventors have also recognized that OCT-guided ultrafast laser surgery can provide a level of surgical three-dimensional spatial precision superior to existing treatment options.

Fiber-based Delivery

In one approach, ultrafast laser-based surgical devices can deliver light using free space optics, where the light travels in air and is encompassed by mechanical structures. These structures can serve two purposes. Firstly, to contain, for safety purposes, and insulate the light from stray light contamination. Secondly, to support optical elements, primarily mirrors, responsible for relaying and changing the propagation direction of the beam. In another approach, optical systems may use a different delivery mechanism, a fiber-optic cable. In a fiber-optic cable, electromagnetic radiation from a source, such as a laser, is delivered into the proximal end of a cable and the light propagates inside the cable until it exits at the distal end.

Fiber optic delivery may offer certain benefits as compared to an exclusively-free-space delivery approach. Along a fiber-optic cable, there is no need for mirrors and the associated structural hardware, the mechanics are generally simpler, the assembly is easier and the system setup, calibration, and maintenance can be faster because an influence of environmental factors, such as temperature changes causing structural movement (e.g., affecting alignment for precise optical systems), is generally reduced. Additionally, the physical mechanism responsible for delivering the laser light from the laser itself to the surgical target, can be significantly reduced, such as conferring major ergonomic, space-saving, and usability advantages. In a free space system, the physical mechanism generally must support various motion degrees of freedom to position the laser output correctly relative to the patient. This may be accomplished with either a 3-axis motorized gantry or manual articulating arms. For conveyance of ultra-short pulses from an output of an ultrafast laser, conventional silica-core-based optical fibers are not suitable because of high dispersion, low energy thresholds, and detrimental non-linear effects.

The properties generally specified for ultra-short pulse fiber transport are single mode operation, low propagation loss, low dispersion, high coupling efficiency, high energy threshold, and sufficient bandwidth to cover the spectral spread of femtosecond and picosecond pulses. Specialized fibers meeting such properties can be used to deliver ultrafast pulses over several meters.

For example, hollow-core photonic crystal fibers (HC-PCF) guide light through a gaseous core, which is generally surrounded by a regular or irregular lattice and crystalline-like microstructure. Geometric characteristics of this lattice microstructure, which generally comprises alternating lower refractive index (gas) and higher refractive index (solid) regions, generally determine specific propagation characteristics in the hollow core, such as bandwidth/wavelength, energy, and transmission losses. As the light propagates through a gas, most commonly air, there is no material-induced chromatic dispersion, ensuring that the spectral bandwidth is preserved. The single mode, specific bandwidth, low loss, and acceptable low chromatic dispersion properties of HCF make them suitable for ultrashort pulse transmission in a robust, flexible package such as suitable for use in the ultrafast laser surgery applications described herein. Generally, in a hollow-core fiber, a cross-sectional microstructure determines the physics of the light guiding mechanism. The microstructure can include regular or irregular patterns of holes with different shapes. The guide mechanisms fall into two general categories: photonic bandgap (PBG), or inhibited coupling (IC). The PBG and IC fibers each may present respective trade-offs. PBG are more generally more mechanically robust, while IC fibers (e.g., Kagome-type fibers) may support much higher bandwidths and energy per pulse as compared to a PBG fiber.

Generally, the PBG mechanism can be considered an optical analog comparable to electron band gap behavior in solid state physics. In solids, the band gap represents an energy difference between energy levels associated with valence and conduction bands, and electrons are forbidden to have an energy lying within the band gap. Similarly, in a photonic crystalline structure, the microstructure establishes a photonic bandgap corresponding to forbidden photon energy levels, and therefore wavelength bands, for which propagation is suppressed within the solid structure: these multiple forbidden guidance regions can then only travel in the hollow core. The length scale of the photonic crystal structure periodicity is sub-wavelength of the bandgap wavelength itself. Accordingly, the configuration of deliberate "defects" (e.g., inhomogeneities corresponding to a lattice structure) in the solid core allows specific, banded light propagation in a hollow core fiber. An illustrative example of a microstructure of a PBG fiber is a stacked, hexagonal arrangement of silica rods with air spacing.

By contrast, a Kagome fiber is an IC fiber whose periodic lattice pattern comprises triangles and hexagons. The IC fiber physical mechanism is analogous to the Von Neumann bound or quasi-bound state in condensed matter physics. The microstructure comprises a lattice pattern supporting a continuum of modes, which are deliberately out-of-phase and thereby "inhibiting" the light from escaping the core.

The present apparatus and systems for ultrafast laser surgery described herein are not restricted to the use of specific PBG or IC fibers, but instead can include or use any type of fiber capable of transmitting a ultrafast laser pulse with acceptable power loss and dispersion. Hollow core fibers are available from several manufacturers including NKT (Birkerod, Denmark), GLOphotonics (Limoges, France) and iXblue Photonics (Lannion, France).

Accessing the Oral Cavity, Pharynx, Laryngeal Inlet and Trachea

According to an illustrative example, trans-oral optical access is used to treat targeted larynx tissue. Trans-oral surgery is used for a variety of diseases including: early stage laryngeal cancer and benign lesions such as papillomas, nodules and polyps; oropharynx and hypopharynx cancers; and oral cavity pre-cancerous and cancerous lesions. Other instrumentation and surgical access methods are compatible with the subject matter herein, where the present subject matter includes delivery of an ultrafast laser beam to, for example, the larynx.

A surgical laryngoscope is a long metal tube through which surgical instruments are inserted, or a laser beam is transmitted. Laryngoscopes come in different lengths, ranging from 15 cm up to 20 cm, as illustrative examples, and cross-sectional profiles depending on the patient anatomy, age (e.g., pediatric vs. adult), and anatomical area of interest. A cross-sectional profile can be constant through the length or can vary with a smaller distal cross-sectional area that expands proximally. Cross-sectional profiles can be circular, elliptical, or triangular as illustrative example. A medium-sized, most-commonly-used laryngoscope has internal profile dimensions of 13.5 mm to 16 mm. Laryngoscopes are typically named for the inventor such as the Kleinsasser, Benjamin, Lindholm, Benjamin-Parsons, Parsons, Benjamin-Lindholm, and Dedo. Examples of such laryngoscopes can be obtained from Karl Storz (Tuttlingen, Germany). To assist with $CO_2$ laser surgery, the laryngoscopes can provide lateral channels for suction tubes to remove vapor. Additionally, laryngoscopes generally include a variety of mechanisms for illumination such as light clips or exterior channels for fibers. For surgery, the patient can be placed in what is referred to as a "Jackson/traditional sniffing position," with cervical spine flexion relative to the thoracic spine and extension of the atlantooccipital joint.

Figure 4A:
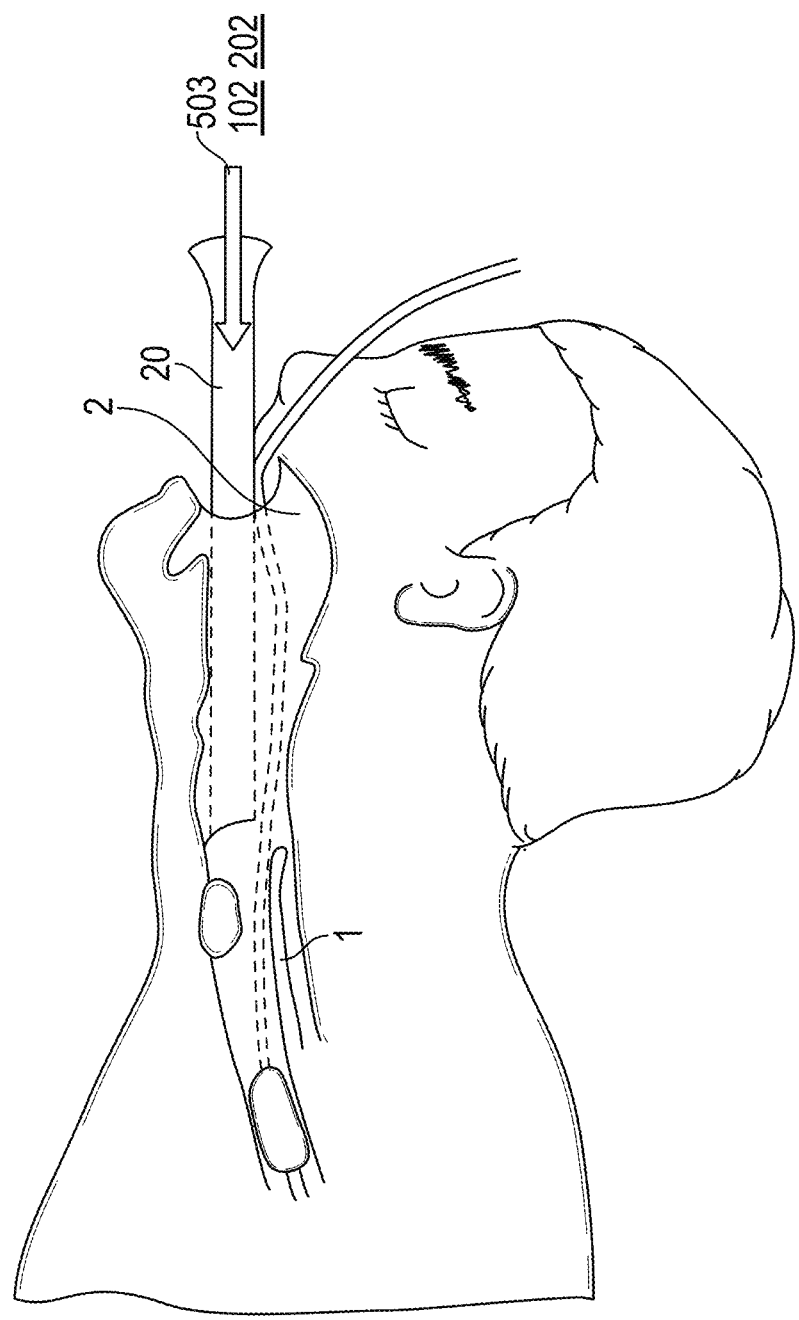
FIG. 4A illustrates generally a view of a configuration that can be used to provide optical access to a laryngeal region, such as using a laryngoscope or other elongate member.
Figure 4B:
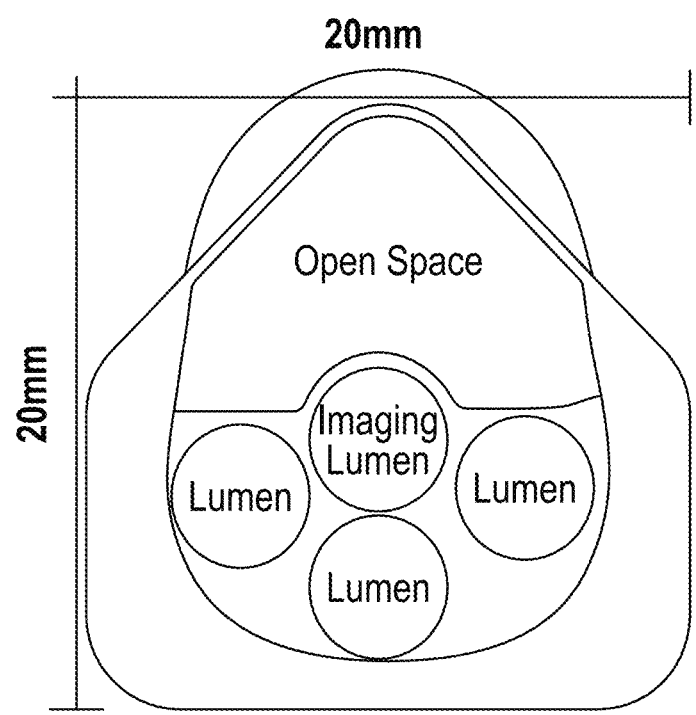
FIG. 4B illustrates generally an end view of a laryngoscope, showing an illustrative example of different regions that can be used to provide access for surgical implements or optical access, or combinations thereof.

FIG. 4A illustrates generally a view of a configuration that can be used to provide optical access to a laryngeal region, such as using a laryngoscope or other elongate member, and FIG. 4B illustrates generally an end view of a laryngoscope, showing an illustrative example of different regions that can be used to provide access for surgical implements or optical access, or combinations thereof. With reference to FIG. 4A, according to an illustrative example, optical access to the larynx 1 can be achieved by endoscopically delivering an ultrafast laser beam 102 and OCT beam 202 through a laryngoscope 20. The patient is positioned for direct line-of-sight to the larynx and to maximize the opening space. The laryngoscope enters the oral cavity 2 and is positioned superior of the larynx 1. The laryngoscope is inserted to move the tongue out of the way. Laryngoscopy surgery generally involves suspending the laryngoscope—roughly above the patient's chest—with a fixture, freeing up the surgeon to use both hands. With reference to FIG. 4B, an illustrative example is presented, such as showing how portions of a cross-sectional area of a working channel of a laryngoscope can be partitioned, such as having an open space for insertion of cold instruments, and lumens defined for imaging or other purposes. In another example, the open space can be used as a pathway for free-space beam propagation from a surgical head, through the laryngoscope, to a tissue site.

Integrated Surgical System

With reference to the systems shown and described herein, various components (such as a portion or entirety of certain described components) can be included as a portion of a surgical head or other assembly. For example, a portion or an entirety of the optical components can be located inside an enclosure sheath that connects to, and inserts into, the laryngoscope to hold the sheath in place. This elongate member can be referred to as the surgical sheath, or simply a sheath, but the subject matter described herein need not be restricted to use of a sheath. The sheath can include a pre-assembled opto-mechanical assembly with connections to mechanically mate the sheath to the laryngoscope, so that the location of the opto-mechanical assembly relative to the laryngoscope remained fixed as the laryngoscope is moved and suspended in place. The sheath can be a sealed unit, protecting the components, such as scanners and optics, from fluid ingress, dust, or other environmental contaminants.

In the following discussion, a beam may refer to a single function or "modality" of light, or a multi-modal combination comprising two or more electromagnetic waves with distinct properties. Distinct properties include wavelength or bandwidth for lasers or incoherent sources respectively, beam diameter, polarization, propagation direction (toward or away from the tissue site). Modality types include the ultrafast laser, OCT, aiming beam, illumination, or visualization as illustrative examples. For a multi-modal combination, the distinct beams can include a fully co-axial configuration, with a common optical axis, or an offset configuration, with decentered axes.

Figure 5A:
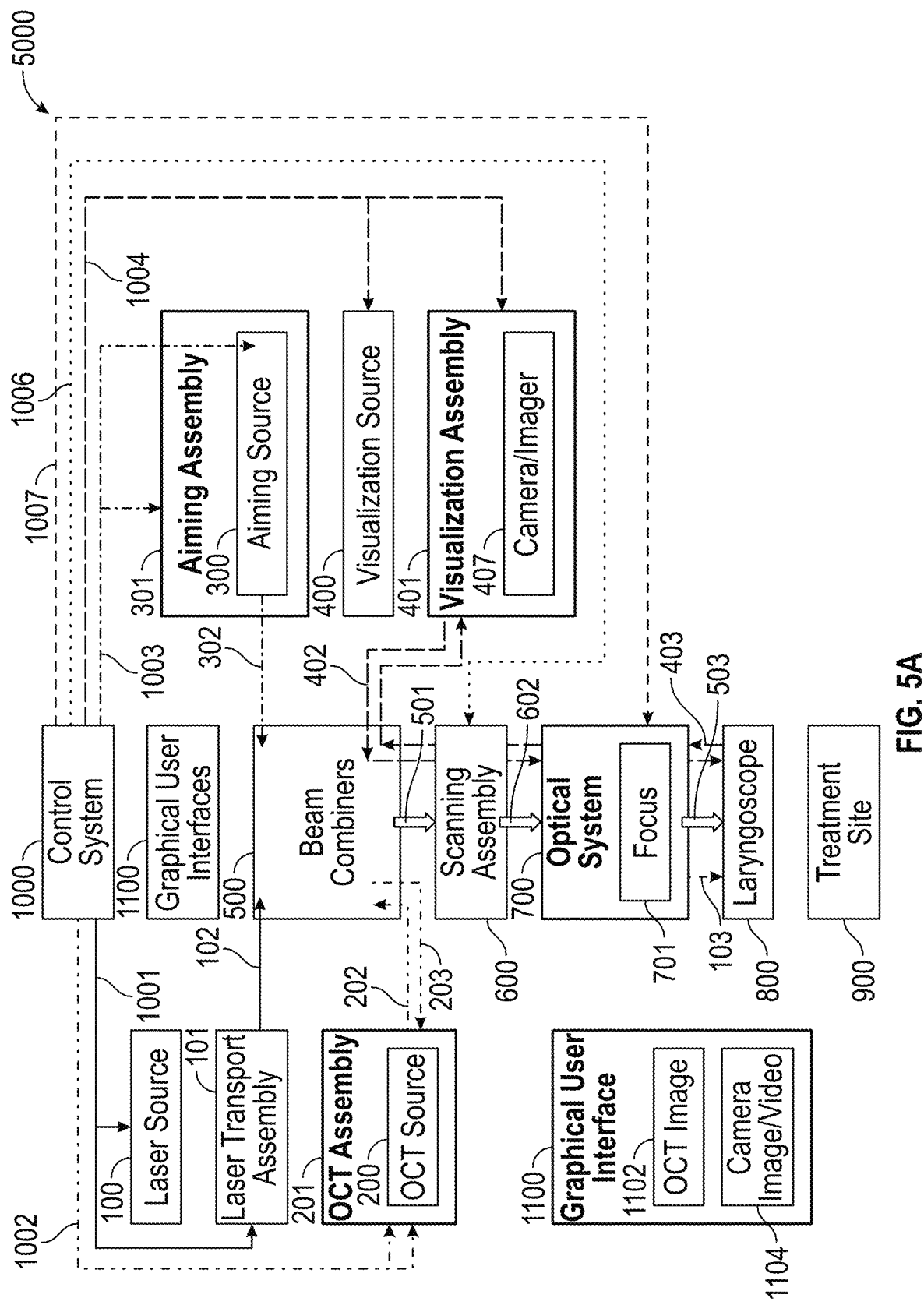
FIG. 5A illustrates generally an example comprising a system for surgical laser beam delivery and control.

FIG. 5A illustrates generally an example comprising a system 5000 for surgical laser beam delivery and control. With reference to FIG. 5A, an integrated surgical system 5000 for bladeless tissue processing (e.g., for trans-orally accessing a laryngeal region) can include a control system 1000 and associated graphical user interface 1100. The control system 1000 can include single or multiple processing facilities configured to control software and hardware components of the integrated system 5000. One or more of the parameters mentioned above can be controlled using instructions input by a user through a graphical user interface 1100. The control system 1000 memory or storage device can include firmware or software that translates user inputs into signals that precisely perform motion control such as generating control data for scanning mirror deflection for the scanners 600, visualization light intensity for the visualization sources 400, or movement of focusing optics 701 along a specified axis, or synchronization of movements over multiple axes, as illustrative examples.

The control system 1000 can generate ultrafast laser control signals 1001 for the ultrafast laser source 100 and ultrafast laser transport assembly 101. Ultrafast laser control signals 1001 can control one or more operations, such as: ultrafast laser source 100 warm up, laser warm down, turn on, turn off; adjusting the output laser beam 102 repetition rate and pulse energy; movement of beam shutters within the laser transport assembly 101; and the status of such actions displayed on the graphical user interface 1100. The control system 1000 can generate OCT system control signal 1002 for the OCT source 200 and OCT assembly 201. OCT system control signal 1002 can control one or more operations, such as: OCT source 200 turn on, turn off, warm up and warm down; adjusting the power of output OCT beam 202; movement of polarization and delay line hardware within the OCT assembly 201; acquisition of and synchronization of hardware within the OCT assembly 201 for OCT image processing such as balanced detectors, acquisition cards, and spectrometers, based on the output OCT beam 202 and return beam 203; and the display of OCT images 1102 (e.g., cross-sectional representations of tissue) and OCT status on the graphical user interface 1100.

The control system 1000 can generate aiming beam system control signals 1003 for the aiming source 300 and aiming assembly 301. Aiming controls signals 1003 can control one or more operations, such as: aiming source 300 turn on, turn off and adjusting the output aiming beam 302 power; movement of shutters within the aiming assembly 301; and the display of output aiming beam 302 status on the graphical user interface 1100. Visualization system control signals 1004 can control one or more operations, such as: visualization source 400 turn on, turn off and adjusting output visualization beam 402 power; camera or imaging 407 device settings, such as shutter speed, exposure time or white balance, in the visualization assembly 401; and movement of the camera or imaging device 407 according to focus in the visualization assembly 402. As an illustration, the visualization source 400 and visualization assembly 401 are include external third-party equipment, such as the surgical microscope, with which the beam combiners 500 can be optically interfaced.

Ultrafast laser beam 102, OCT beam 202 and aiming beam 302 are combined in the beam combiners 500. The beam combiners can be a single element or multiple elements combining the beams in stages through dichroic filters, polarization or another approach. The visualization beam 402 can also be combined with the other beams using the beam combiners 500. In another approach, the visualization beam 402 can be routed either via fiber or free-space separately from the surgical laser beam 102, OCT 202, and aiming beam 302. Beam combination may be achieved with all beams co-axial, a plurality of beams co-axial, or each beam having its own separate axis. The beam combiners 500 can include multiple separate components at different positions along the optical train, such as a first element that combines the ultrafast laser beam 102 and OCT beam 202, and another element that combines this ultrafast laser-OCT bundle with an aiming beam 302.

A combined beam output 501 is generally directed to a scanning assembly 600. Scanning control signals 1006 control the scanning pattern. For example, the ultrafast laser pattern can be three-dimensionally programmed for width, length, and depth. The three-dimensional scan can be established using a series of stacked two-dimensional scans. The scanners 600 can move the combined beam 501 in two dimensions along the width and length axes. The combined beam output 501 refers to a common optical path and does not necessarily mean the beams are enabled and propagating together contemporaneously at all times. For example, the ultrafast laser control signal 1001 and OCT control signal 1002 could be synchronized such that they propagate together, and are scanned contemporaneously, while the aiming control signal 1003 propagates at a different time. As an illustration, the ultrafast laser beam 102 and OCT output beam 202 can be programmatically scanned very quickly, while the aiming beam 302 is manually controlled through the graphical user interface 1100 and moves comparatively more slowly. This arrangement reflects the expected clinical practice of the aiming beam 202 being used as a range finder and target locater for the ultrafast laser beam 102 and output OCT beam 202.

The scanned combined beams 602 enter the optical system 700 (e.g., an achromatized optical system). The optical system 700 is a series of lenses arranged to focus the ultrafast laser beam 102 down to a diffraction-limited, or very close to diffraction-limited (e.g., high Strehl ratio), spot for a particular specification, such as f-number. The size of the spot is determined, at least in part, by the ultrafast laser beam 102 wavelength, a numerical aperture of the laser beam, and suppression (e.g., minimization) and balancing of aberrations of the optical elements. The same generally applies for the output OCT laser beam 202 and aiming beam 302. As mentioned above, the optical system 700 can be achromatic to establish co-located foci for the ultrafast laser beam 102, OCT laser beam 202, aiming beam 302 and visualization 402, or the optical system 700 can be arranged to have longitudinal chromatic dispersion deliberately. Control system signals 1007 can control the optical system 700 to provide focus adjustment (e.g., to control a depth of a focal plane).

The focus control 701 optics adjust the focus location of the beams along their local optical axes. This can include moving multiple lens elements or a single lens in the axial direction with a stepper motor or other mechanical positioner. The focus could also be changed using an electro-optical element. Once a layer of tissue has been treated (e.g., removed using the ultrafast laser beam 102), the focus control 701 can shift the focus deeper (further away from the scanners), or vice versa, and the two-dimensional pattern can be repeated. An initial depth of treatment can be sub-surface, and a range of depths being treated can be entirely sub-surface, as an illustrative example. The focused combined beam 503 can be delivered through a laryngoscope 800 to a treatment site 900 for aiming, tissue modification, and OCT. Reflected visualization beam light 403 can be collected by the optical system 700 and propagated back to camera/imager 407 for real-time display of a camera image or video 1104 on the graphical user interface 1100.

In the discussion above, and for reference below, a beam may refer to a single function or "modality" of light, or a multi-modal combination comprising two or more electromagnetic waves with distinct properties. Distinct properties include wavelength or bandwidth for lasers or incoherent sources respectively, beam diameter, polarization, or propagation direction (toward or away from the tissue site). Modality types include the ultrafast laser, OCT, aiming beam, illumination, or visualization as illustrative examples. For a multi-modal combination, the distinct beams can include a fully co-axial configuration, with a common optical axis, or offset, with decentered axes. In reference to FIG. 5A, the control system 1000 can include firmware or software containing instructions that, when executed by a processor, perform OCT image 1102 processing, analysis, and generation of a presentation for display. The control system 1000 can include a memory (or other storage device) or processing unit (e.g., one or more general purpose processor circuits or graphics processing units (GPUs)) to store, run and, process instructions (e.g., firmware or software) to establish a scanning pattern, such as based upon inputs from the graphical user interface 1100. The control system 1000 can also include software or related routines that manage, store, or establish calibration data or settings that can mathematically represent a relationship between the focus of the ultrafast laser beam, the OCT beam, and the aiming beam 302. These relationships could be presented to the user on the graphical user interface 1100 in the form of visual markers on the OCT image 1102 and camera image/video 1104.

In reference to FIG. 5A, an aiming beam source 300 can include an economical, compact, and monochromatic source such as a diode laser chip mounted on custom mechanicals, or an off-the-shelf fiber-coupled or free-space "plug and play" unit. The aiming assembly 301 can include a beam conditioner, comprising single or multiple optics, to alter the output aiming beam profile 302. The function of the conditioners can include one or more of: circularizing the beam profile, such as using cylindrical lenses, because a laser diode output can be elliptical and/or beam expansion, deliberate mechanical vignetting or aperturing to reduce the output beam size; or mechanical features to eliminate or reduce undesirable beam profile features such as diffraction rings. The conditioners can also house a beam splitter to create two separate, parallel beams having equal intensity to accomplish a "range finding" purpose. This beam splitter can be a glass window, with a specified thickness, coating specification, and mounted angle, to create the desired separation between respective beam portions.

In reference to FIG. 5A, visualization sources 400 can include LEDs, xenon lamps, or another visible light source. Generally, visualization sources 400 can be implemented as small, compact, high intensity, white LEDs, or other sources. The visualization assembly 401 can include multi-modal fibers or other visible light fiber delivery. The visualization assembly 401 can also comprise optics configured to illuminate and image the target tissue by both delivering the visualization beam 402 to the tissue and then collecting scattered light into a collection beam 403. The visualization assembly 401 can include an optical system to image the collection beam 403 onto a camera/imager 407, forming a finite conjugate imaging system, where light reflected from the tissue site is focused onto a solid-state (e.g., silicon) detector. The visualization optics are generally configured to meet specified resolution, magnification and field-of-view requirements that are clinically relevant. The detector can include a CMOS or CCD camera, such as available from Teledyne FLIR (Wilsonville. OR, USA), Ximea (Munster, Germany), or Basler (Ahrensburg, Germany).

The visualization beam 401 can be delivered separately from the visualization optics. For example, where a laryngoscope 800 is used, the visualization assembly optics may only serve to image the sample tissue. Generally, the visualization assembly 401 will contain filters to suppress scattered ultrafast laser 102 and OCT beams 202 and 203, and permit light that falls within the collection angle of the visualization optical system from reaching the detector, such as to inhibit adverse effects on visualization image quality.

In reference to FIG. 5A, the scanning assembly 600 can include one or more different scanner technologies used for the purpose of scanning the ultrafast laser beam 202, OCT beam 202, and aiming beam 302, such as to provide scanning in two dimensions. For example, angular galvanometer scanners are available from Cambridge Technology (Bedford, MA, USA), Scanlab (Munich. Germany) or ScannerMAX (Sanford, FL, USA). Microelectronic Mirrors (MEMs) are another technology and are available from Mirrorcle (Richmond, VA) and Hamamatsu (Hamamatsu City, Japan).

Another scanning device can include an acousto-optical deflector, such as available from Gouch & Housego (Torquay, UK) or Brimrose (Sparks, MD, USA). Generally, one galvanometer mirror or acousto-optical deflector is used per scan axis, while MEMs mirrors can be both single and double axis. Two scanning axes orthogonal to each other can be defined, lateral-medial and anterior-posterior. Looking down a patient's throat, the lateral-medial axis is horizontal or left-to-right and would correspond to scanning from the left vocal cord across the throat to the right vocal cord. The anterior-posterior axis is the vertical or top-to-down direction, corresponding to scanning from the epiglottis to the esophagus. The scanners can include: galvonometer-based with two separate mirrors, one mirror for each scanning axis; two separate MEMs mirrors, one mirror for each scanning axis; a two-axis MEMs mirror; or a series of acousto-optical deflectors, as illustrative examples.

Generally, OCT has two resolution components: axial resolution and lateral resolution. As previously discussed, the axial resolution is a function of source characteristics (bandwidth and center wavelength). The lateral resolution is a function of the optical configuration, such as f-number. The resolution of the OCT beam 202 can be regarded as the smallest possible feature that can be observed in an OCT image or other OCT data set. OCT imaging can provide specified resolution to image micrometer-scale anatomical features for surgery or diagnosis. For example, the superficial lamina propria—the critical layer of the vocal folds for phonation—is approximately 100 µm to 200 µm thick. Two-dimensional OCT images can be used to determine one or more of a shape, a size, or a location of lesions. Additionally, OCT images 1102 in the larynx can provide in vivo diagnostic capabilities that augment existing methods. Using superluminescent laser diodes (SLD) with center wavelengths in the near-infrared (NIR) range, an illustrative example may be capable of 5 µm OCT image resolution. For SD-OCT, the OCT assembly 201 could include the SLD, spectrometer, fiber network comprising elements such as splitters and circulators, reference arm sub-assembly and delay line. For a SS-OCT system, the components can include be a laser, k-clock, balanced detector, fiber network, and reference arm sub-assembly.

Figure 5B:
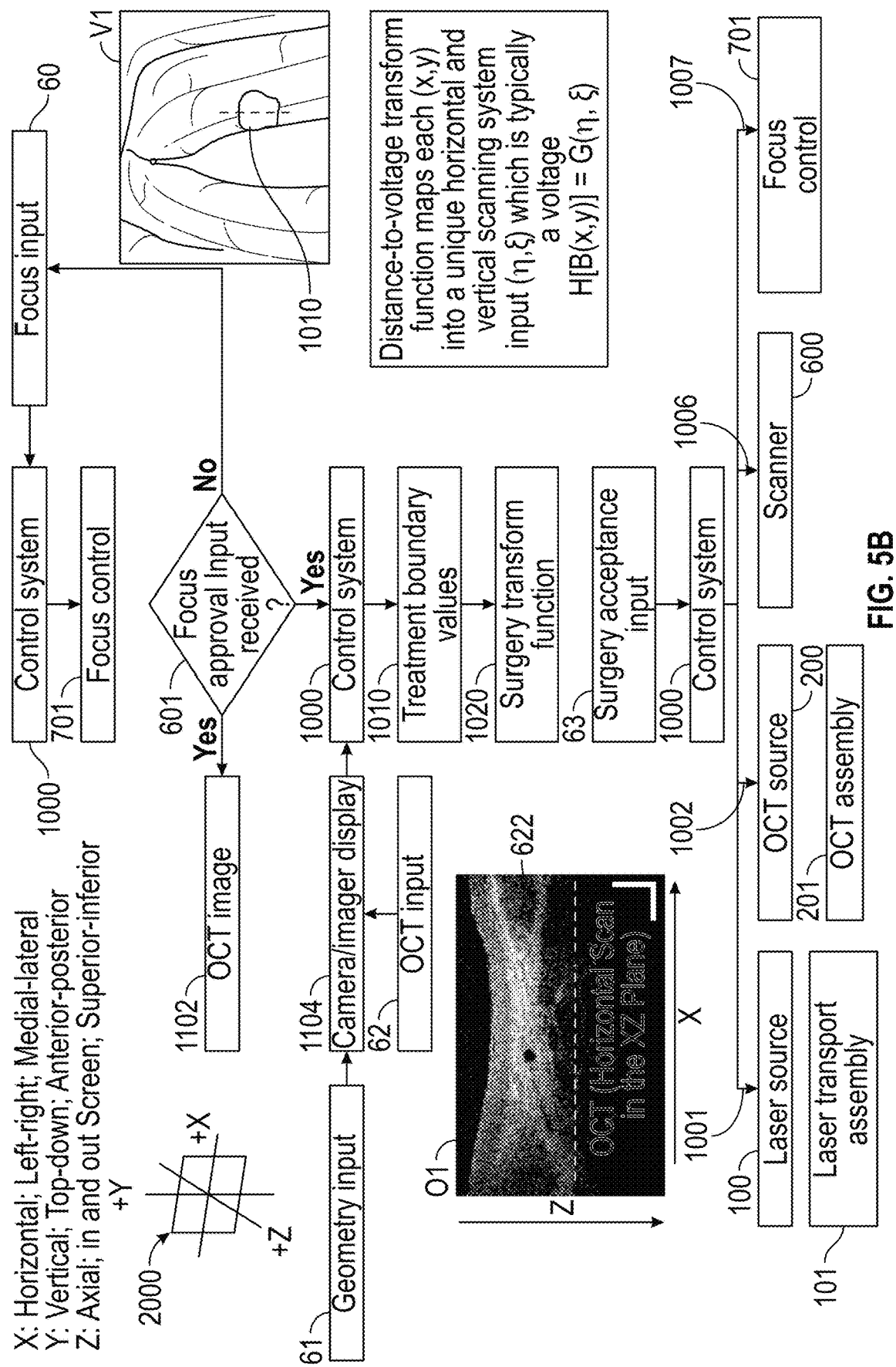
FIG. 5B illustrates generally an example comprising a workflow for performing laser surgery, such as can include use of the system shown in FIG. 5A or according to other examples herein.

FIG. 5B illustrates generally an example comprising a workflow for performing laser surgery, such as can include use of the system shown in FIG. 5A or according to other examples herein. In reference to FIG. 5B, the following description involves an illustrative example of a surgery facilitation sequence. The control system 1000 receives a focus input 60 from the user. In reference to FIG. 5A and FIG. 5B, based on this focus input 60, the control system 1000 generates a focus control signal 1007 which adjusts the focus control 701. The control system 1000 will receive the focus input 60 until, for example, the user decides the camera image 1104 is in focus. Alternatively (or in addition), if external imaging equipment is used, then the focus input 60 is applied to the control system 1000 based on the view through the oculars/surgical microscope. The control system 1000 will then be presented with user approval input 601 accepting the current focus position as the initial starting location for surgery. Focus acceptance input 601 breaks the focus input 60 loop described above and the OCT image 1102 can be activated. Focus acceptance input 601 permits the control system 1000 to receive a two-dimensional geometry-based input 61 on the camera/imager display 1104. The geometry-based input could be a freeform shape drawn by the user on the graphical user interface 1100 (for example using a touchscreen). The shape represents the treatment zone, and whose boundary represents the path of the focused ultrafast laser beam 102 (with such boundary 1010 shown illustratively in an inset image V1 on the right of FIG. 5B).

In another example, the geometry-based input could be a fixed shape, such as a rectangle, that is established by the control system 1000.

Figure 2:
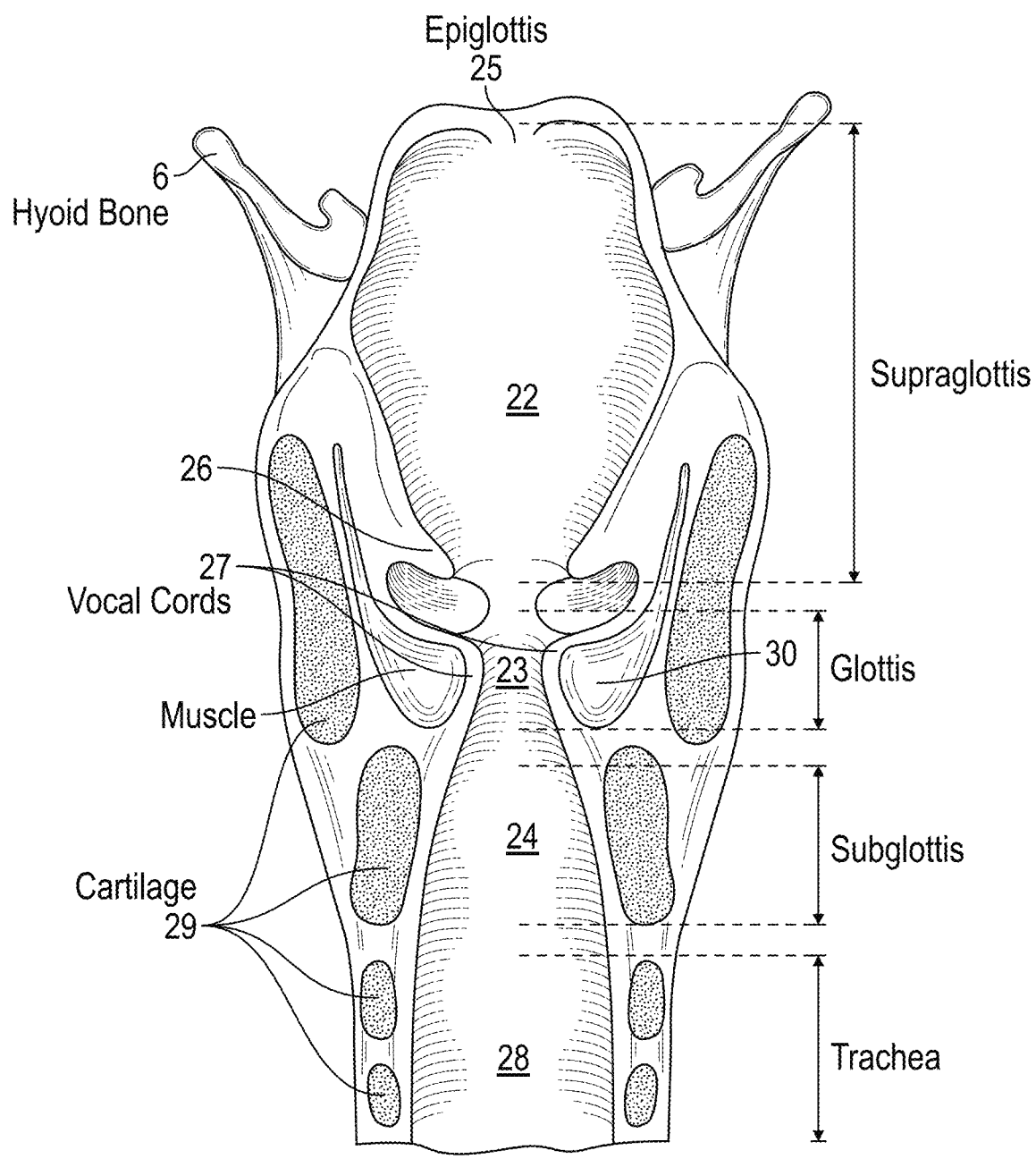
FIG. 2 illustrates generally a section view of human anatomy showing different laryngeal regions.
Figure 3A:
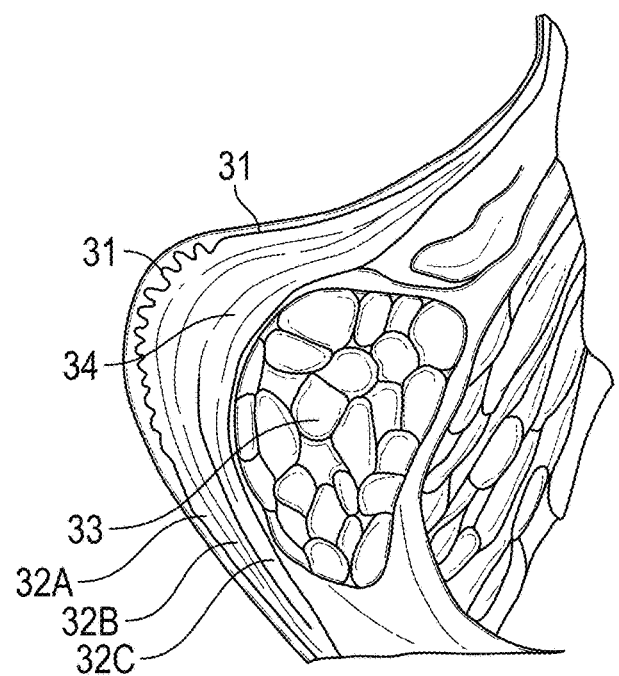
FIG. 3A illustrates generally a section view of human anatomy showing different tissue structures that can form a vocal fold region.
Figure 3B:
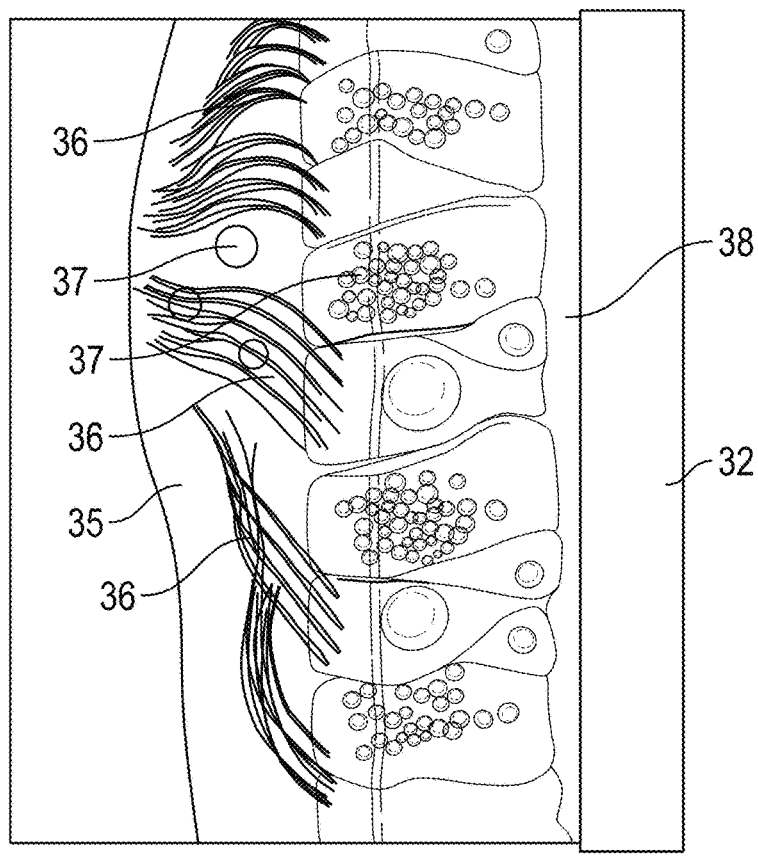
FIG. 3B illustrates generally a view of human anatomy showing different tissue structures associated with a squamous epithelium and associated mucociliary blanket.

The control system 1000 can store or generate a mathematical representation of points on the camera/imager display 1104 in a three-dimensional global co-ordinate system. A global coordinate system 2000 can include two orthogonal axes in plane with the camera/imager display 1104, with one axis parallel to the camera/imager display horizontal and the other axis parallel to the camera/imager display vertical. A third axis can be orthogonal to the camera/imager display 1104 plane. In the practical terms of the camera/imager display 1104 or view through a surgical microscope, the axes can be labeled "x," "y," and "z," where a positive z direction is "out of the screen," a positive x direction is right-facing and positive y direction is top-facing. In anatomical terms, in reference to FIG. 2, which represents the XY plane, the positive Y direction can be toward the epiglottis 5 and the negative Y direction can be toward the trachea 8, with the x axis spanning a medial-lateral direction across the vocal cords 7. In this coordinate system, the x-axis is the medial-lateral axis, the y-axis is the anterior-posterior axis, and the z-axis is the superior-inferior axis.

The control system 1000 can represent a boundary of the geometry input 61 as a discrete series of co-ordinates B(x,y) that represent the treatment boundary values 1010 and the control system 1000 can use a surgery transform function 1020 to map each (x,y) into uniquely mapped values $(\eta,\xi)$ that, in reference to FIG. 5A, correspond to scanning assembly control signals 1006 for the horizontal and vertical scanning of the ultrafast laser beam 102. Therefore, the B(x,y) coordinate values can be mapped to a set of control values $G(\eta,\xi)$. Such scanning assembly control signals 1006 are generally voltages and the transform function 1020 can include or use a calibration constant connecting physical laser beam movement to applied voltage, such as mapping an amount in microns (or other units) that the laser beam will move per applied volt. The transform function can be more complicated than a simple constant and could also be a function of the axial distance, z, as an illustrative example.

In reference to FIG. 5B, the control system 1000 may also receive a geometry-based OCT input 62 on the camera/imager display 1104. The OCT image 1102 could include a single panel, or multiple panels. For example, each panel can represent a cross-sectional OCT covered by a single scanning axis. For example, scanning in the y or vertical direction corresponds to an OCT image in the YZ plane and scanning in the x or horizontal direction corresponds to an OCT image in the XZ plane. In an example comprising a two-axis OCT scanning system, two OCT images 1102 (XZ and YZ planes) would be calibrated to each other such as that each image corresponds to the same z-range. In such an example, there would be a single OCT geometry-based input 62 presented to the control system 1000. This input would be the vertical position of a depth indicator 622, such as a horizontal line, on the two OCT images 1102 as shown in the inset O1 (which is representative of a cross-sectional representation of a tissue site as may be provided). With calibration relationships between the OCT images 1102, camera display 1104, and focus control 701, a vertical position of this indicator will correspond to a specific z-depth to excise tissue.

After the user is satisfied with their geometry input 61 and OCT input 62, then the control system 1000 can be presented with a surgery acceptance input 63 to begin automated treatment. After surgery boundary input 63, the control system 1000 generates ultrafast laser control signals 1001 for the laser source 100 and laser transport assembly 101; OCT control signals 1002 for the OCT source 200 and OCT assembly 201; scanner control signals 1006 for the scanners 600; and focus control signals 1007 for the focus control 701. The surgery acceptance input 63 could be generated in many ways, such as depressing a foot pedal, pressing a button on the screen, or using a voice command.

Figure 5C:
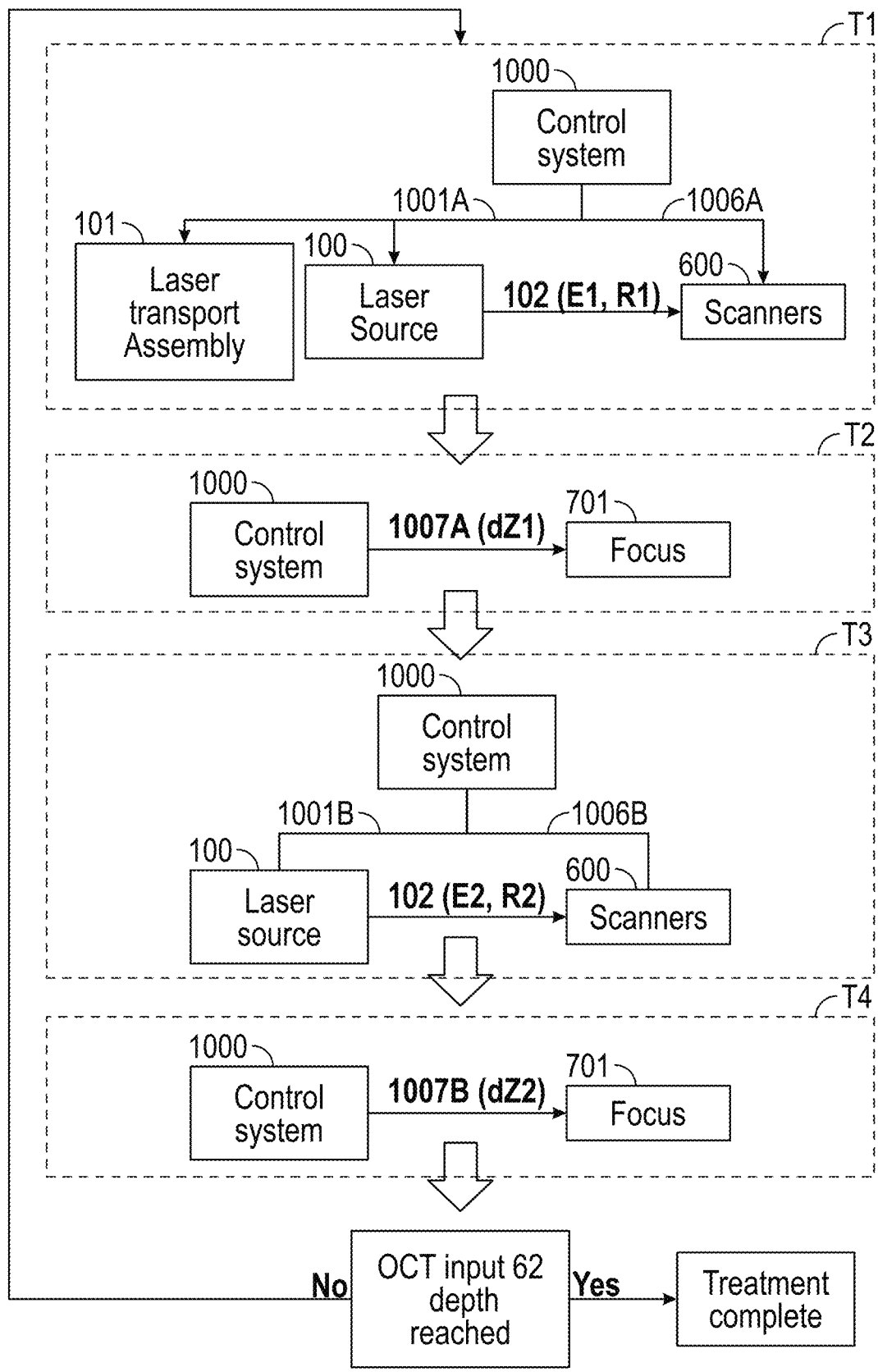
FIG. 5C illustrates generally an example comprising a treatment protocol, such as can be performed using the workflow shown in FIG. 5B and using the system as shown in FIG. 5A, or according to other examples herein.

FIG. 5C illustrates generally an example comprising a treatment protocol, such as can be performed using the workflow shown in FIG. 5B and using the system as shown in FIG. 5A, or according to other examples herein. The control system 1000 is configurable to synchronize and sequence control signals to perform treatments. As an illustration, ultrafast laser control signals 1001A are sent out contemporaneously with scanner controls signals 1006A. Ultrafast control signals 1001A fire the ultrafast laser source 100 to establish an ultrafast laser beam 102 with pulse energy E1 and repetition rate R1, and, for example, open shutters in the laser transport assembly 101 contemporaneously with scanner control signals 1006A to scan the ultrafast laser beam in a pre-configured pattern, such as a raster pattern at a particular depth to modify (e.g., remove) a layer of tissue. This can help to provide controlled spacing between spots; if the laser was firing during acceleration or deceleration then the spots would be bunched up or spread out respectively. This treatment stage is denoted as T1 and is an excision step, where E1 and R1 are chosen to excise tissue precisely with a controlled (e.g., very low) temperature rise. After the completion of the first treatment stage T1, treatment stage T2 involves the control system 1000 generating focus control signals 1007A to move the laser focus by a fixed amount dZ1. The treatment stage T3 can involve a different set of ultrafast laser control signals 1001B that are generated to fire the laser with a pulse energy of E2 and repetition rate R2. E2 and R2 can be chosen to cause hemostasis by either ablating blood vessels directly or deliberately inducing a very localized temperature rise at each scanning location. The deliberate temperature rise would cause coagulation, where blood clots at approximately 60 C (approximately 23 C temperature rise above normal body temperature).

The example above is merely illustrative. Hemostasis could be enhanced in many ways. Hemostasis could be enhanced by increasing a count of effective pulses per location. Laser signals 1001A and 1001B could be different to vary the repetition rate, having R2 greater than R1 as an illustrative example. Scanning signals 1006A and 1006B could be different to vary scanning parameter such as the scanning frequency or the spot size separation. Hemostasis could be enhanced through single, independent application of one of these approaches or a combination of multiple approaches. For example, establishing R2 to be higher than R1 and choosing scanning signals 1006B to result in slow mirror movement than scanning signals 1006A would result in the additive effect of more pulses per scanned location. Hemostasis could also be induced by adjusting the fluence at a focal location, which could be accomplished by establishing laser signals 1001A and 1001B that are different.

The difference in laser control signals between two different modes could include one or more of: altering the pulse energy, with E2 greater than E1 as an illustrative example; change the beam diameter to alter the spot size between T1 and T3 to change the fluence; change the pulse triggering mode that certain off-the-shelf laser systems offer, known as a "burst mode", which can be used to deliver a higher energy over a pulse envelope comprising a series of pulses which are triggered off the oscillator. Further, the laser control signals could be varied to change the wavelength of the laser for preferential molecule absorption.

All of the aforementioned approaches—count of effective pulses, spot separation, fluence or wavelength—can be applied independently, or in concert, to impart more energy to the same location to deliberately induce a temperature rise to facilitate hemostasis or to ablate blood-carrying structures, such as vessels, while still suppressing collateral damage. After the completion of the treatment stage T3, a treatment stage T4 can involve the control system 1000 generating focus control signals 1007B to move the laser focus by a fixed amount dZ2. In reference to FIG. 5C, the amount of total focus system 701 movement can be determined based on user OCT input 62, which can set a depth at which to complete the treatment, and the incremental focus movement for each T2 and T4.

For each incremental movement dZ1 or dZ2, the control system 1000 updates the total focus movement for the treatment. The sequence T1 through T4 can be repeated until the total focus movement first equals or exceeds the prescribed depth range corresponding to OCT input 62. The incremental fixed focus movements dZ1 and dZ2 could be the same value, or different values. In reference to FIG. 5C, as part of a pre-configured pattern, ultrafast control signals 1001A and 1001B could involve turning off or "blanking" during non-linear stages of scanning mirror motion, such as acceleration and deceleration when the line scan is changing directions.

In reference to FIG. 5C, the order or nature of treatment operations can vary. For example, the tissue treatment stages could be reversed, such as within a cycle or from cycle-to-cycle, where the hemostatic treatment T3 may occur before a tissue excision or removal operation. An intermediate focus stage T2 might not be required and only one focusing operation could be performed per excision and hemostasis iteration. In reference to FIG. 5C, a count of treatment stages could also be altered. For example, one treatment stage could be used with laser control and focus signals chosen to both excise and enhance hemostasis contemporaneously. Treatment stages may be repeated with one T1 stage followed by two T3 stages or three T1 stages followed by a single T3 stage, as an illustrative examples.

In an illustrative example, during excision cycle T1, spot size, $d_{spot}$=28 µm, R1=70 kHz and E1=200 µJ and during the hemostasis enhancement cycle T3, spot size=28 µm, R2=200 kHz and E2=200 µJ. An effective count of laser pulses per spot location, $N_{eff}$, is given by the following expression, where v is the linear scanning speed:

$$N_{eff} = \sqrt{\frac{\pi}{2}} \frac{d_{spot} R}{2v}$$

Generally, a linear scanning speed is a function of the treatment dimensions and the scanning frequency. With a cycle defined as two line scans in opposing directions, a scanning frequency is a count of cycles per second. In this illustrative example, for a 5 mm×5 mm×5 mm excision, the excision and hemostasis effective counts of pulses per spot are 0.58 and 5.85, respectively (e.g., a roughly ten-to-one ratio between an excision mode and a hemostasis-enhancement mode).

Figure 6:
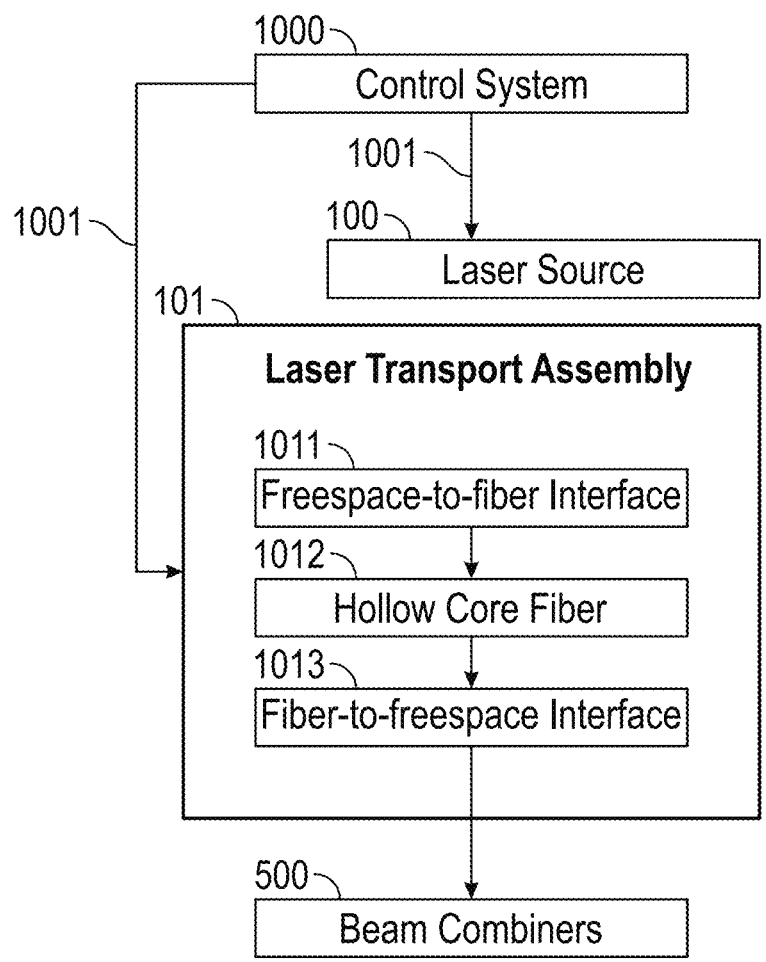
FIG. 6 illustrates generally an example comprising a laser transport assembly, such as can be used to provide delivery of ultrafast laser pulses using a hollow-core optical fiber structure.

FIG. 6 illustrates generally an example comprising a laser transport assembly, such as can be used to provide delivery of ultrafast laser pulses using a hollow-core optical fiber structure. In this example, the control system 1000 generates ultrafast laser control signals 1001 to fire the laser source 100 to create an ultrafast beam 102. The ultrafast beam 102 enters the laser transport assembly 101, and the free-space-to-fiber interface couples the ultrafast laser beam 102 into the hollow core fiber 1012. For example, laser transport assembly control signals 1001 could be responsible for opening and closing a shutter located prior to the free-space-to-fiber interface 1011. Waveguiding properties of HCFs involve in-coupling provisions that include, and may exceed, those for non-HCF solid-fiber optics. As with single mode non-HCF fibers, optical components generally focus the ultrafast laser beam 102 to a very small (e.g., diffraction-limited) focus with appropriate divergence to avoid large transmission losses, and such optical components are generally fixtured with very tight mechanical tolerances.

Connectorization may involve a region of collapsed holes (solid glass), where a cross section of the hollow-core fiber is compressed or fused. Such a region can suppress or entirely prevent moisture from getting into the cavities within the HCF and condensing; condensation can degrade or even destroy the HCF guidance mechanism. The HCF fiber 1012 can be manufactured with a 1 mm-to-2 mm region of solid glass from a connector facet to hollow core already "built in," as an illustrative example. Alternatively, this solid glass region could be incorporated into the free-space-to-fiber interface 1011 itself. The free-space-to-fiber interface 1101 could also include dynamic beam steering to ensure maximum coupling efficiency despite fluctuations in ambient temperature or fiber bending. Beam stabilization modules are also commercially available from GLOphotonics (Limoges, France), Photonic Tools (Berlin, Germany) and certain vendors that also make ultrafast lasers such as NKT (Birkerod, Denmark) and Amplitude Laser Systems (Pessac, France).

In reference to FIG. 6, the free-space-to-fiber interface 1011, the fiber-to-free-space interface 1013 or other upstream or downstream locations could include physical shutters, which block the beams for safety purposes and can be actuated by the laser transport assembly control signals 1001 generated by the control system 1000. Additionally, the free-space-to-fiber interface 1011 and fiber-to-free-space interface 1013 could also include separate connectorization for OCT fiber hardware. The fiber-to-free-space interface 1013 could also include opto-mechanical mounting and an optical sub-assembly to produce a collimated beam of a certain diameter. The interfaces 1011 and 1013 can include optical components, such as an aspheric lens or a series of lenses, with mechanical mounting to reduce or minimize losses, such as to establish a collimated (very low divergence) beam having a specified diameter. The interfaces 1101 and 1013 optical sub-assembly can be configured for either a fixed beam diameter, or a variable diameter.

In various examples described herein, the ultrafast laser is delivered by an HCF. However, such examples can include free-space delivery. In a free-space delivery example, the ultrafast laser need not be conveyed using a fiber and may be transported using a series of mirrors, such as to convey the ultrafast surgical laser beam (or a combination of optical beams) to an input aperture of an elongate structure such as a sheath. Various degrees of freedom for positioning can be provided, such as accomplished using an articulating arm, by which the ultrafast laser propagates via reflections. For example, such propagation can be through passages internal to the arm. The entrance of the articulating arm can be located at or near an output of a laser source, such as at or near a chassis. At an output port of the articulating arm (e.g., a beam exit port), aspects of the system can be similar to other examples discussed herein, including one or more of beam expanders, dichroics, scanners, along with objective and focusing optics.

Figure 7A:
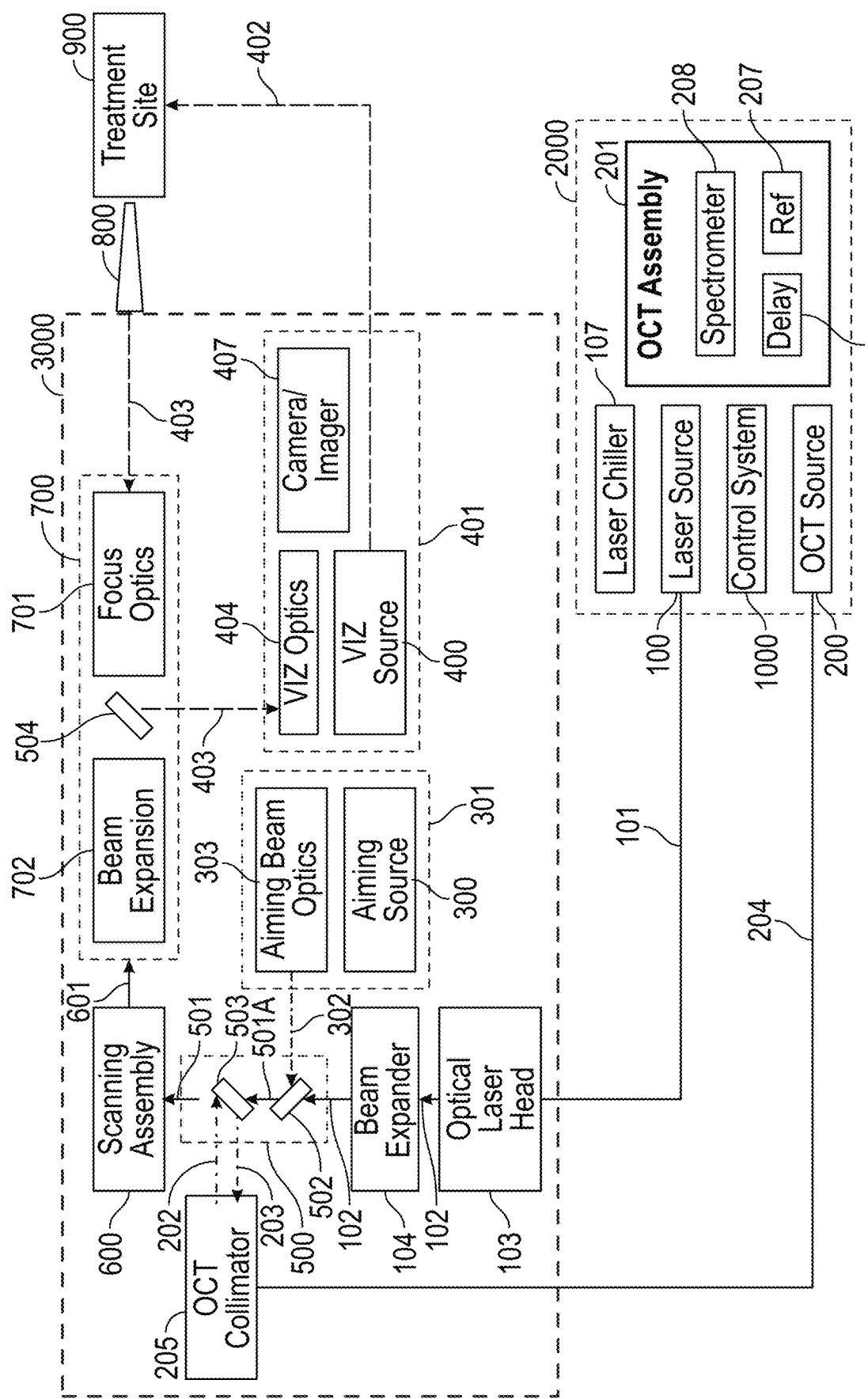
FIG. 7A illustrates generally an example comprising a system including a hybrid laser architecture.

Further examples are discussed below, with variations showing, for example, different laser transport assembly configurations, and placement of hardware relative to an elongate structure such as a laryngoscope. FIG. 7A illustrates generally an example comprising a system including a hybrid laser architecture. A hybrid laser has a non-ultrafast laser source which is physically separated from and connected by a fiber to an optical head, inside which the pulse compression occurs to generate an ultrafast laser pulse. In this manner, an ultrafast laser source is provided by a combination of the laser source 100, the laser transport assembly 101 (e.g., the fiber establishing propagation), and the optical laser head 103. The layout shown in FIG. 7A can include a chassis 2000, that can be positioned some distance away from the patient, and a surgical head or console 3000, such as positioned much closer to the patient. The chassis 2000 can house the control system 1000, which could include a computer and other electronics; a hybrid laser source 100 and a chiller 107; and an OCT source 200 and OCT spectrometer 208 for SD-OCT, as an illustration. The hybrid laser, such as available from IPG Photonics (Oxford, MA), has a laser source/control unit 100 and is connected to an optical head 103. In this example, the laser transport assembly 101 is the fiber propagating the non-ultrafast laser pulse to the optical head 103, which is commercially provided.

Figure 7B:
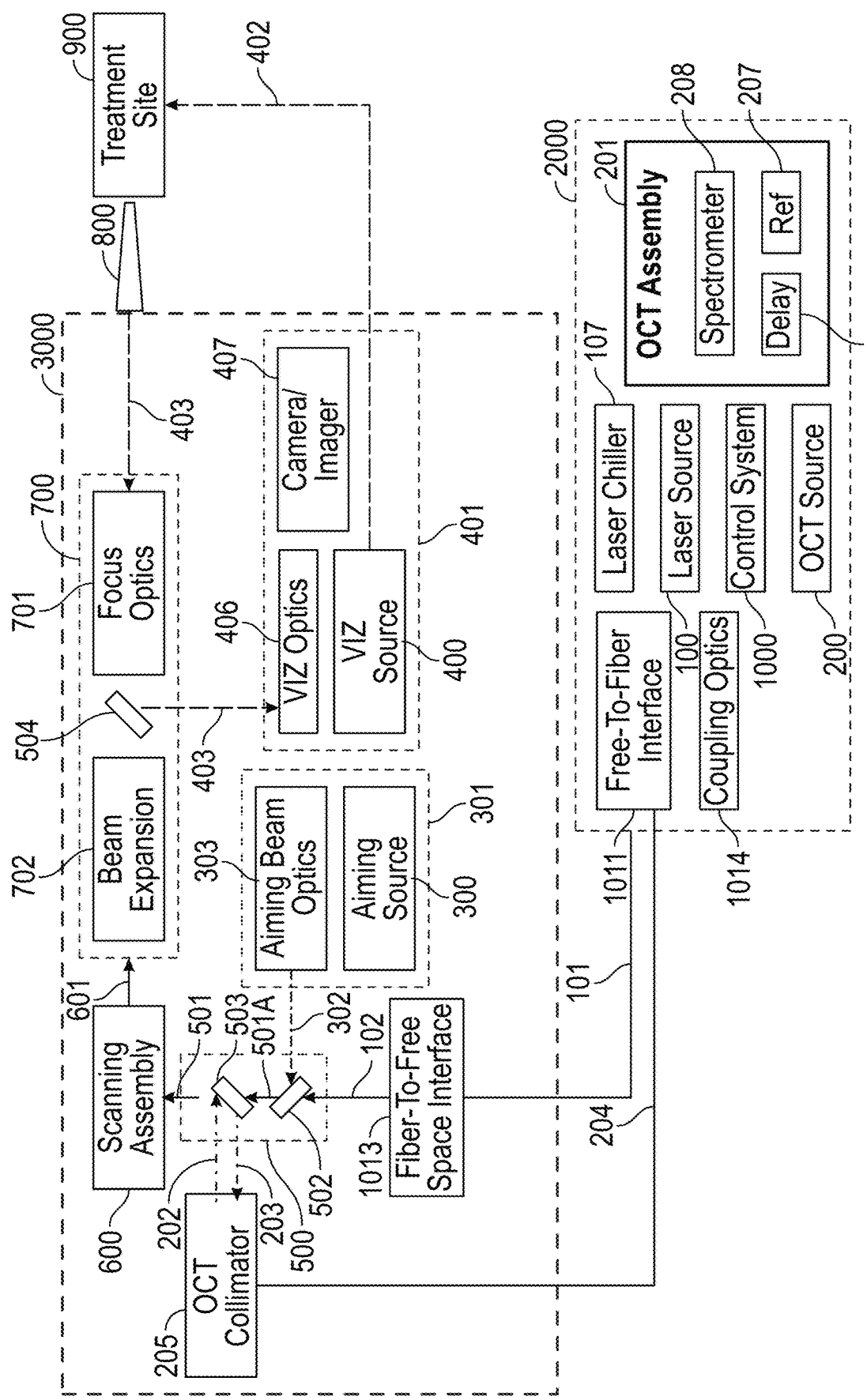
FIG. 7B illustrates generally an example comprising a system including a free-space-to-fiber interface.

FIG. 7B illustrates generally an example comprising a system including a free-space-to-fiber interface. In the example of FIG. 7B, the chassis can also include a free-space-to-fiber interface 1011, such as providing HCF connectorization for the ultrafast laser beam 102 and single mode fiber connection for the OCT beam 202. In this example, the laser source 100 has a free-space output and the chassis includes a free-space path section until reaching coupling optics 1014 to focus the ultrafast laser beam 102 into the HCF. The coupling optics 1014 could be part of the free-space-to-fiber interface 1011. In this case, the laser transport assembly 101 is the hollow core fiber. Inside a surgical console 3000, a fiber-to-free-space interface 1013 expands and collimates the laser light beam to a specific diameter for entrance to the combiners 500.

Figure 7C:
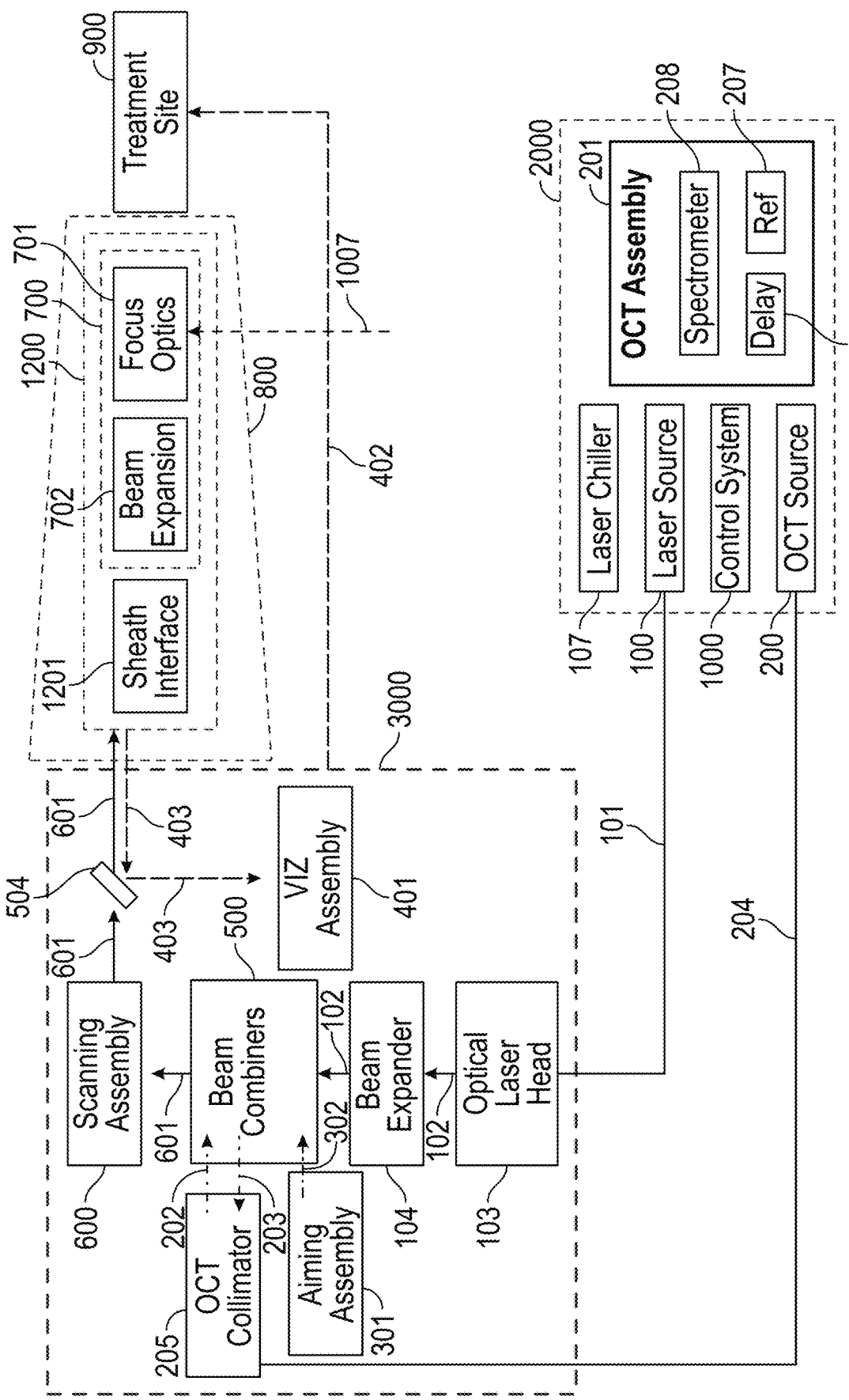
FIG. 7C illustrates generally an example comprising a system including a sheath.

FIG. 7C illustrates generally an example comprising a system including a sheath. In FIG. 7C, a surgical sheath 1200 can be used, such as in combination with a hybrid fiber laser as described in FIG. 7A. The surgical console 3000 can be positioned close to the patient head, such as feeding a proximal laryngoscope 800 end. The surgical console 3000 in this example can share many components as shown in FIG. 7A, including the optical laser head 103 and beam expander 104 for the ultrafast laser beam 102; aiming beam assembly 301 to deliver an aiming beam 302; OCT collimator 205 to send and receive inbound and return OCT beams 202 and 203 respectively; beam combiners 500 to combine the ultrafast laser beam 102, OCT beam 202 and aiming beam 302; scanning assembly 600; and a visualization assembly 401 which delivers an illumination beam 402 and collects an imaging beam 403. In this example, a dichroic 504, which splits the combined ultrafast laser beam 102, OCT beam 202, and aiming beam 302 from the visualization beam 403 can be located outside the optical system 700.

A surgical sheath can be inserted, included, or otherwise placed within a lumen defined by an elongate structure such as a laryngoscope 800. Here the optical system 700 can be contained within the sheath 1200 and accordingly, a working distance of the optical system can be much shorter than other examples. A sheath interface 1201 can provide a mechanical connection to the laryngoscope 800 to ensure that the sheath is positioned correctly and firmly. For example, the sheath interface 1201 could mate to the proximal or distal end of the laryngoscope 800 prior to insertion into a throat of a patient to provide trans-oral access to a treatment site 900.

Focus control signals 1007 from the control system 1000 actuate a focus control mechanism within the optical system 700. For example, an adjustment approach can include an indirect or remote actuation scheme that moves a linear stage, slide, or bearing upon which the optical system 700 was mounted. The sheath 1200 could be inserted anywhere along the length of an elongate structure such as a laryngoscope 800. The focus control mechanism could also be located inside the surgical console 3000 and could mechanically actuate the optical system, or elements of the optical system, from a distance, to provide focusing control. As an illustration, controllable focusing can include a physical electrical communication that applies a voltage to change the shape of a lens, such as a liquid lens, within the optical system 700.

Referring generally to the examples of FIG. 7A, FIG. 7B, and FIG. 7C, a location of the components could be distributed differently within the laryngoscope 800, surgical console 3000, and chassis 2000. For example, the scanning assembly 600 and beam combiners 500 could be miniaturized and fit inside the sheath 1200 which is inside the laryngoscope 800. Component size of scanners, optics, and beam combiners all scale proportionally to a distance between them and the treatment site 900. However, the laryngoscope 800 is typically a tapered elongate instrument with a small cross-section and any components included inside the sheath 1200 must still be sufficiently small. For example, the scanning assembly 600 could be implemented using a 2D MEMS mirror, which has a considerably smaller footprint than a two-axis galvanometer scanning assembly. Furthermore, the MEMS mirror diameter—due to its proximity to the treatment site—could be significantly smaller than corresponding galvanometer mirrors of FIG. 7A and FIG. 7B. Manufacturers such as Mirrorcle, Fraunhofer, and Hamamatsu produce MEMs mirrors with form factors small enough to package inside a sheath portion insertable or otherwise located within a laryngoscope 800.

Beam Expansion

In reference to FIG. 7A and FIG. 7C, the ultrafast laser pulse 102 enters a beam expander 104 to increase the beam diameter. The beam expander 104 could have a fixed or variable magnification, to increase the beam diameter to match an input design aperture of the optical system 700. Diffraction-limited off-the-shelf fixed beam expanders are available from a variety of manufacturers such as Asphericon (Jena, Germany), Thorlabs (Newton. NJ, USA), Newport (Irvine, CA, USA), or Edmund Optics (Barrington, NJ, USA).

Beam Combiners

In reference to FIG. 7A. FIG. 7B, and FIG. 7C, following expansion, the ultrafast laser beam 102 is sequentially combined in the beam combiners 500 with the aiming beam 302 (if present) and then the OCT beam 202. In reference to FIGS. 7A and 7B, the first dichroic filter 502 combines the ultrafast laser beam 102 with the aiming beam 302 for coaxial propagation. In the case that the ultrafast laser beam 102 and the aiming beam 302 are in the infrared and visible portions of the spectrum, respectively, the dichroic filter 502 would be a long-pass filter. The dichroic 503 transmits the dual aiming beam plus ultrafast laser bundle 501A and reflects the OCT beam 202. However, the opposite—with OCT transmission—is also possible and may, for certain instances, be preferred. An OCT source is generally randomly polarized and in reflection, off a dielectric coating stack, optical path length differences between polarization states can be enough to scramble the interference upon which the OCT technique relies, rendering its signal-to-noise ratio degraded. In FIG. 7A, FIG. 7B, and FIG. 7C, the beam combiner assembly 500 is placed after the beam expander 104, however its placement can be swapped with the expansion occurring downstream.

The combined co-axial aiming and ultrafast laser beams 501A enters a second dichroic 503 to be combined with a third beam, the collimated OCT inbound beam 202. The OCT light enters the surgical console 3000 through a single mode fiber 204, whose proximal end is connected to the OCT source 200 on the chassis 2000 and whose distal end is connected to an OCT collimator 205. The OCT collimator can be achromatically designed to accept a single-mode fiber connection and will output an OCT beam 202 of a specific diameter with diffraction-limited wavefront with very low chromatic dispersion across the entire OCT source 200 bandwidth. In an example, where the OCT center wavelength is longer than the ultrafast laser wavelength, the dichroic 503 can be a short-pass filter.

Aiming Beam

In reference to FIG. 7A, FIG. 7B, and FIG. 7C, the aiming beam is generated from an aiming source 300, which is part of the aiming beam assembly 301 and whose output could be conditioned by aiming beam optics 303. The aiming beam optics 303 could have a single or multiple functions including: altering the cross-sectional profile of the aiming beam, for example from elliptical to circular; mechanical solutions, such as deliberate aperturing or baffles, to reduce diffractive effects; or an optical element to split the single output beam from the aiming beam source 300 into two portions, comprising equal intensity beams decentered by a specified distance. The aiming beam assembly 301 could also include a mechanical shutter operated via aiming beam control signals 1003.

Scanners

In reference to FIG. 7A, FIG. 7B, and FIG. 7C, combined ultrafast, aiming, and OCT beam 501 is scanned by components in the scanning assembly 600 (e.g., the respective beams forming the combined beam are "co-scanned"). The scanner can be implemented using, for example, a two-axis galvanometer-based mirror scanning system, where the axes correspond to independent vertical and horizontal scanning axes (with respect to a video image or view down a laryngoscope). The combined scanned beam 601 enters the optical system 700.

Objective and Focus Control

In reference to FIG. 7A, FIG. 7B, and FIG. 7C, the optical system comprises a beam expansion sub-assembly 702, a dichroic 504, and a focus sub-assembly 701. In an example, the beam expansion sub-assembly 702 is an afocal magnification system, with collimated inputs and outputs, such that the output beam is larger than the input collimated combined scanned beam 601. The beam expansion sub-assembly 702 can be achromatic so that the ultrafast laser beam 102, OCT beam 202, and aiming beam 302 are all magnified by the same specified amount and can be controllably "co-focused" together.

The collimated light passes through a dichroic 504. The dichroic 504 spectral profile is established to provide efficient transmission for the collimated combined beam, mid-level reflectivity for the aiming beam bandwidth, and high reflectivity for the portion of the collected visible light beam 403 outside the aiming beam bandwidth. In such a manner, ultrafast beam 102 and OCT beam 202 throughput will be enhanced (e.g., maximized) to ensure highest surgical efficiency and OCT image quality; high, spectrally uniform collection efficiency for satisfactory visualization image intensity and quality; and an appropriate ratio of aiming beam 302 transmission-to-reflection to ensure the aiming beams can be seen on the visualization image. After the dichroic 504, the combined collimated beam enters the focus optics 701, which focus the beam through the laryngoscope 800 onto the treatment site 900.

In reference to FIG. 7A, FIG. 7B, and FIG. 7C, in conjunction with the scanners, the zoom and objective components can focus the ultrafast, aiming, or OCT beams (or combinations thereof) inside, and to different positions within a surgical volume. Such positioning can be accomplished with micrometer level accuracy, as an illustrative example. Generally, one aspect of the zoom and objective systems is to balance the optical aberrations, and create a diffraction-limited, or close to diffraction-limited, spot through a targeted surgical volume. Generally, the optical configuration accounts for manufacturing tolerances that introduce aberrations and cause deviation from ideal performance. Sources of aberrations introduced by manufacturing tolerances include: purely optical tolerances such as lens radius of curvature, glass thickness and lens wedge; individual lens or dichroic mountings or sub-assemblies, containing multiple lenses, being decentered or tilted; variability of "drop in" components such as acousto-optical deflectors, lenses or beam expanders; and power on nominally flat surfaces.

The objective structure is generally configured for a nominal f-number, which is the "speed" or relative aperture, to create a specified spot size (and therefore fluence). The f-number is the ratio of the effective focal length to the input beam diameter. For optical configurations where the lens system is to be located within a laryngoscope, a size of the entrance pupil can be constrained by an allowable maximum extent of the components within the laryngoscope visualization channel (or other channel). For optical configurations where the lens system is outside an elongate structure such as a laryngoscope, a minimum effective focal length can still be constrained by a length of an elongate structure such as a laryngoscope, through which the surgical laser beam is delivered to a tissue site. Such constraints are illustrative examples relating to the use of an elongate structure such as a laryngoscope, and other geometries are possible.

A zoom lens, which may include a single lens or groups of lenses, can be movable such that a location of the ultrafast spot is adjustable along the longitudinal axis of an elongate body such as a laryngoscope providing depth selectivity at the tissue site. For example, such as using the configuration of FIG. 7A, the surgical console 3000 can accommodate a movable mechanism that can include a servo or stepper motor. Servo or stepper motors having specifications to accomplish micrometer level depth precision to control collateral damage are available from manufacturers including Parker Hannifin (Mayfield Heights, OH, USA), Heydon Kerk (Milford, NH, USA), Zaber Technologies (Vancouver, Canada) and Motion Solutions (Aliso Viejo, CA, USA).

The zoom system can be partially or entirely contained within a section of a surgical sheath inside a laryngoscope, or other similar configuration, establishing a compact configuration. Examples of small-form-factor control mechanisms with the specified resolution and range include direct-current (DC) servo linear motors (e.g., having a height of 12 mm, width of about 6 mm, and length of about 27 mm) from Faulhaber (Schoenaich, Germany), and piezo-driven linear actuators (e.g., having a height of about 6 mm, a width of about 15 mm, and a length of about 23 mm) from Xeryon (Leuven, Belgium). Such examples are illustrative and other control configurations can be used. To accomplish a compact hardware footprint inside a surgical sheath, a diffractive lens structure can be used, instead of or in addition to refractive structures. The diffractive structure can include features having a wavelength or sub-wavelength scale. One or more metalenses can be used, such as in conjunction with conventional optics for the focusing optics, for example.

In reference to FIG. 7A, FIG. 7B, and FIG. 7C, and generally, for the examples in this document, portions, or the entirety, of the optics described above can be specified and arranged for reduced or minimal longitudinal and lateral chromatic aberration (achromatization). Such optics may be used to convey the visualization beam, scanning of the OCT beam, and scanning of the aiming beam, as an illustrative example. Throughout a surgical volume during depth and surface scanning, the focus location of the aiming beam, OCT beam, and ultrafast beam can be co-located to perform surgery. Non-idealities or offset effects can be accounted for through calibration. Further, deliberate wavelength-dependent offsets can also be a design feature and accounted for via a calibration approach. Similarly, a visualization system optical configuration is also specified to provide an achromatic response across the visible wavelength range.

Visualization Assembly

In reference to FIG. 7A, FIG. 7B, and FIG. 7C, after reflection off dichroic 504, the collected light beam 403 enters the visualization assembly 401. Visualization optics 406 form a finite conjugate system, whereby the treatment region 900 is imaged onto a detector 407 for a target magnification based on the sensor 407 dimensions to provide a visible-light visualization. Visualization optics 401 can be configured for a specified field-of-view and imaging resolution. The collected light beam 403 is a fraction of the illumination light beam 402. In this example, the illumination light beam 402 is delivered separately via flexible fiber optic cables, which are attached to the outside of the laryngoscope, so that the fiber distal ends are close to the treatment site 900 to maximize the illumination light irradiance striking the treatment site 900. The illumination beam 402 could also be coupled into and delivered through the optical system 700.

A visualization system provides a real-time image or video feed to aid a surgeon with diagnostics, surgical planning to identify anatomy and target tissue locations, feedback during surgery, or post-op observation. A visualization system generally includes illumination and collection paths. The illumination path can be referred to as the "inbound" path of photons (towards the tissue site) and the collection (imaging) path is "outbound." In the examples in this document, the illumination path can include light sources onboard the chassis which are fiber-coupled to transmit a broadband, visible light to the tissue site. For example, catalog laryngoscopes can provide side mounting features for illumination fibers. For flexibility, multi-core fibers can be used, such as those available from Industrial Fiber Optics (Tempe, AZ. USA). However, solid core multi-mode fibers can also be used. Light sources, such as surface mounted LEDs, can be mounted inside an elongate member such as a surgical sheath, and fiber-coupled, with the fibers routed on a side of a laryngoscope. As another example, a free-space illumination scheme can be implemented using surface-mounted LEDs on a distal end of a surgical sheath or custom laryngoscope.

Illumination photons striking the tissue site will scatter, and a fraction of these photons can back-scatter within a collection solid angle of the visualization system imaging optics. The collection beam can pass through a portion of the surgical optics, strike a dichroic (e.g., dichroic 504) and can be redirected via a series of, or a single, reflection to the visualization optics. Together the portion of the surgical optics and the visualization optics are configured to image a sample plane onto an imaging detector surface as a finite conjugate system providing specified magnification, field-of-view, and resolution. A visualization imager can be a digital system with specified frame rate to produce video, such as for contemporaneous (e.g., "real-time" or near-real-time) imaging to support surgical planning, diagnosis, or treatment. A camera or other imager used for visualization can include either a generally-available circuit assembly level or housed system, or a custom system.

FIG. 8A illustrates generally an example comprising an optical system, such as can be positioned using a movable platform. A collimated ultrafast laser beam 102 enters the scanners. In FIG. 8A, galvanometer mirrors are used where the scanners 601 and 602 are for vertical and horizontal laser beam deflection, respectively. Other scanning approaches can be used as shown and described in relation to other examples herein. The scanned collimated light enters a dichroic 504 which splits various beams, including surgical laser beam and OCT beams, along with aiming and visualization beams (if used). A beam expansion assembly expands the ultrafast laser beam to the diameter required for the f-number of focusing optics 701.

Figure 8C:
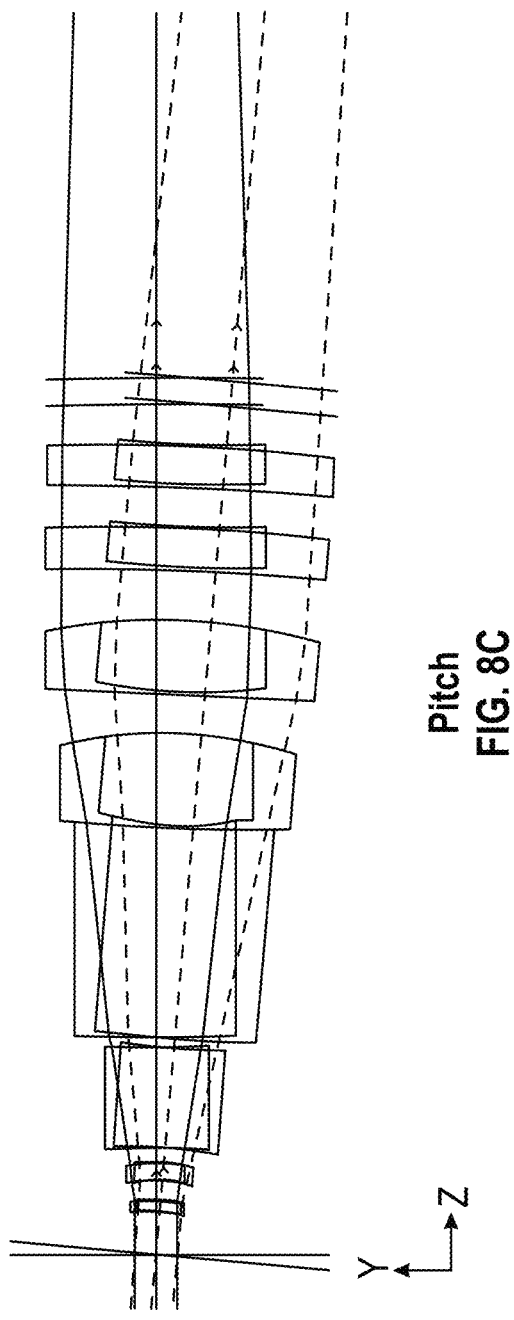
FIG. 8C illustrates generally movement (e.g., rotation) of the optical system of FIG. 8A about an X-axis in a pitch direction (e.g., vertically with respect to the illustration of FIG. 8A).
Figure 8D:
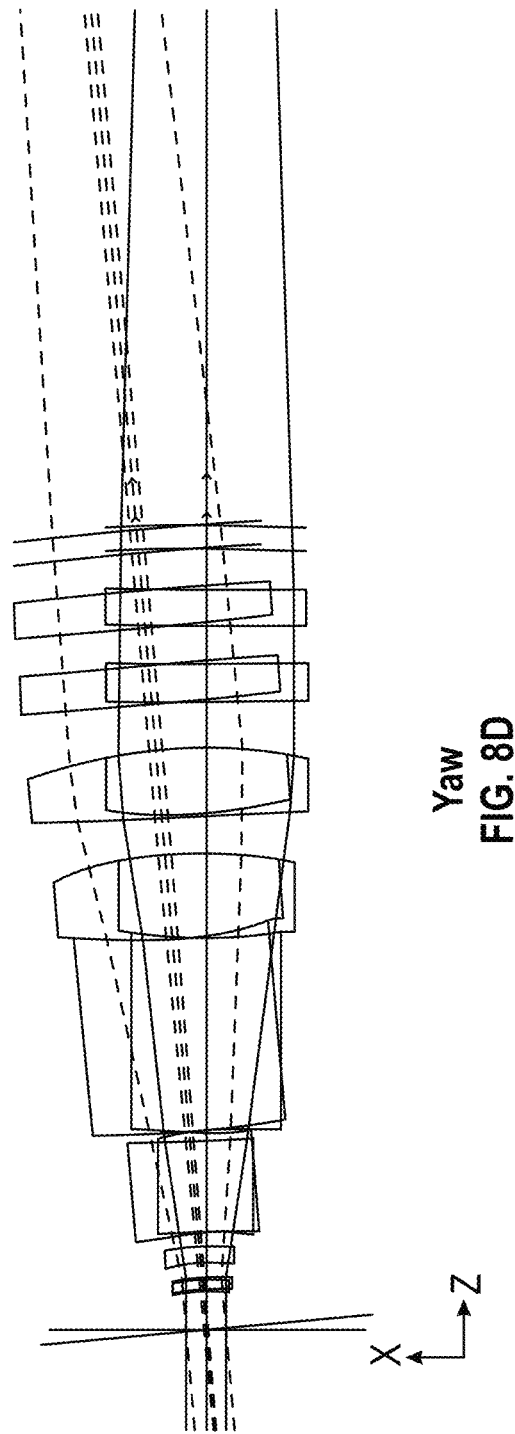
FIG. 8D illustrates generally movement (e.g., rotation) of the optical system of FIG. 8A about a Y-axis in a yaw direction (e.g., horizontally "in and out of page" with respect to the illustration of FIG. 8A).

As shown in the inset, the optical system (such as an achromatized optical system) can address a first addressable region 801, such as within a larger second addressable region 802 within the visualization field-of-view 803. For example, the larger second addressable region 802 can be a composite region created by moving the first addressable region 801 relative to visualization field-of-view 803. The first addressable region 801 corresponds to the accessible area on the treatment zone within the field of view 803 that can be reached exclusively by the scanners 601 and 602. The surgical console 3000 (or a portion thereof) can be mounted onto a movable platform, which can position the surgical console 3000 using, for example, two or more degrees of freedom. For example, the movable platform can rotate about two axes (e.g., "pitch" and "yaw") as shown illustratively in the examples of FIG. 8C and FIG. 8D, respectively, such as driven by respective electrically-operated actuators. For example, FIG. 8C illustrates generally movement (e.g., rotation) of the optical system of FIG. 8A about an X-axis in a pitch direction (e.g., vertically with respect to the illustration of FIG. 8A), and FIG. 8D illustrates generally movement (e.g., rotation) of the optical system of FIG. 8A about a Y-axis in a yaw direction (e.g., horizontally "in and out of page" with respect to the illustration of FIG. 8A).

In reference to FIG. 5B, the two rotation axes could be parallel to the x and y axes of the co-ordinate system 2000, such that the surgical console can be pitched upwards or downwards or yawed left or right relative to the treatment plane. The surgical console 3000 can include the scanners 600 and optical system 700 and, in reference to FIG. 7A, other components such as the beam expander 104, beam combiners 500, aiming beam assembly 301, OCT collimator 205 and visualization assembly 401. In this fashion, the first addressable 801 can be moved relative to the visualization field of view 803. Pitching or yawing (or both) can dramatically increase the accessible treatment area. A size of the addressable regions 801 and 802 shown in FIG. 8A can be determined by the focus optics 701 f-number and the entrance (proximal) laryngoscope cross-sectional shape and size.

A trade-off generally exists between spot size and scanning field-of-view. As an illustration, a nominal f-number of the focusing optics 701 is 18 for a spot size of 28 μm (Gaussian beam input) with a first addressable region 801 size of 4×5.5 mm and a second addressable region 802 of 14×18.5 mm for a standard DEDO laryngoscope and 400 mm working distance. As an illustration, FIG. 8B illustrates generally an example comprising various different regions that can be addressed within a cross-sectional area of an elongate instrument, such as using the optical system of FIG. 8A, where each of the circular regions shown in FIG. 8B can correspond to a first addressable region, with different positions of the first addressable region selected by the movable platform within a second addressable region within a cross-sectional area of the laryngoscope.

In an example, the focus optics may focus a collimated input only along one axis to create a focused line (as opposed to a focused spot). A length of the focused line can be specified to ensure that the line fluence is above a plasma-induced ablation threshold. Establishing such a line can be accomplished, for example, by using cylindrical lenses, which are only powered in one axis. The line can then be scanned vertically and horizontally by the scanning elements 601 and 602. In reference to the protocol shown in FIG. 5C, the excision T1 and hemostasis T3 steps could be completed more rapidly using a line-focused approach.

In reference to the examples of FIG. 8A, FIG. 8B, FIG. 8C, and FIG. 8D, the scanning field-of-view and focus adjustment can be a function of patient anatomy. Where the input to the focus optics 701 is collimated light, an effective focal length can be equivalent to a distance from the focus optics 701 to the treatment site 900. In practice, this "working distance" varies due to patient anatomy, such as epiglottis-to-tracheal length. This working distance is also influenced by user selection of laryngoscope, which could be due to surgeon preference or functional considerations such as the patient age (child vs adult), gender, mouth opening size, or the surgery type. As the throat diameter is also variable, then the position of the vocal cords will also be variable relative to the fixed image field-of-view. As such, one can define a "surgical volume," which is the spatial envelope that includes the entire laryngeal anatomical distribution.

The optical configuration shown illustratively in FIG. 8A can account for anatomical differences and can successfully address an entirety of a targeted surgical volume. For example, focus optic 701 adjustment, which corresponds to moving the focus optics along an axis parallel to the z-axis, can be specified to be sufficient to cover the depth of the surgical volume. The optical system and scanning assembly are capable of delivering and focusing the ultrafast laser beam to a spot size capable of plasma-induced ablation or photodisruption at any horizontal or vertical (x,y) with diffraction-limited or near diffraction-limited performance throughout the entire surgical volume.

Figure 9:
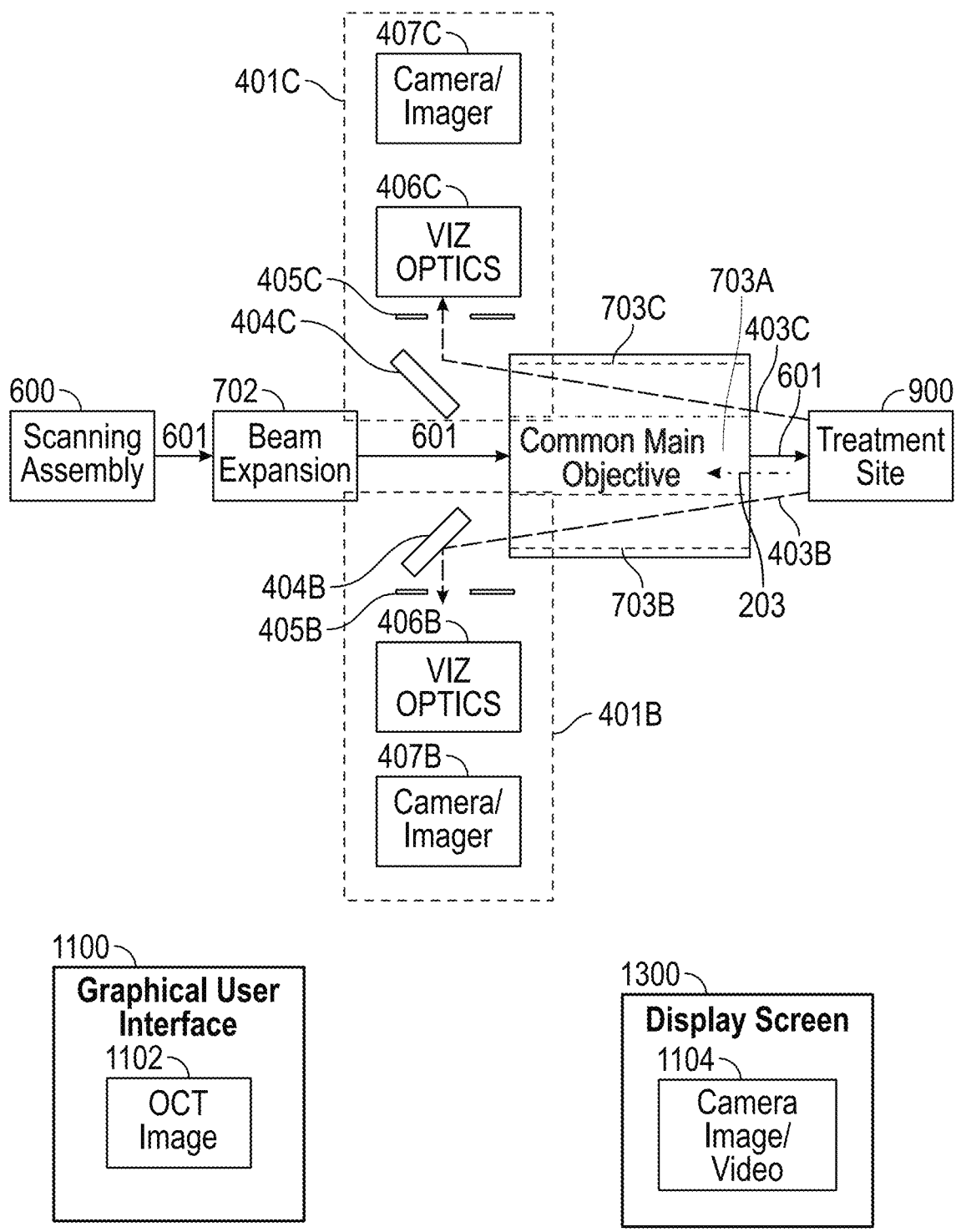
FIG. 9 illustrates generally an example comprising an objective that is shared by visualization optical pathways and a surgical laser beam.

FIG. 9 illustrates generally an example comprising an objective that is shared by visualization optical pathways and a surgical laser beam, such as supporting stereoscopic or 3D visualization to replace traditional oculars. A common main objective 703 can be optically divided into three sections: a central section 703A and two symmetrically arranged peripheral regions 703B and 703C. The combined beam 601, comprising the ultrafast laser, OCT, and aiming beams (if used), are transmitted, and focused through the central portion 703 of a common main objective (CMO) 703 onto the treatment site 900. This central portion is also responsible for collecting the back-scattered OCT beam 203. The visualization can include two physically separate systems 401B and 401C, each with their own optical components and detectors and only sharing the CMO 703. Visualization collection beams 403A and 403B, corresponding to spatially offset and slightly different perspectives of the treatment site 900, pass through peripheral sections 703A and 703B of the CMO.

The optical division between the three paths can be accomplished by the placement of two stops 405B and 405C, which constrain the collection angles of the two visualization assemblies 400B and 400C. These collection angles are equal in magnitude, but opposite in sign. Each visualization assembly can include a collection beam (403B, 403C), a mirror (404B, 404C), a stop (405B, 405C), and visualization optics (406B, 406C) to condition the rays for imaging onto the detector (407B, 407C). In both visualization arms, the systems form finite conjugate systems with the same optical performance, but with different perspectives.

The CMO 703A can provide diffraction-limited or near diffraction-limited performance for multiple modalities: OCT, ultrafast laser, aiming beam, and dual visualization. The two camera images can depict the treatment site 900, but due to their differing perspectives, such depictions will be spatially shifted. Image processing can be performed on the two images. Alignment correction can restore the 401B and 401C image alignment errors due to optical misalignment or fabrication tolerances. This can be accomplished, for example, by computing a homography matrix. Errors in this process could be sourced from decentration (vertical or horizontal or a combination), rotational error, and zoom. Color correction may also be performed because a raw image color profile may differ from the object color profile. However, it is possible that color correction is not necessary as the detectors may contain embedded white balance control and adjustment. A 3D display screen 1300 can provide 3D perspective of the treatment site 900 on the camera image 1104 and a standard 2D screen to display the OCT image 1102, as an illustrative example.

Benign lesions, such as polyps and nodules, have different morphology than the tissue in which they grow. Benign lesions typically manifest as protuberances above the surface and have low infiltration depths and are confined to the mucosa and lamina propria. These physical and morphological differences make benign lesions visually different than the surrounding tissue in cross-sectional images such histology. OCT can be used to produces in situ, non-destructive cross-sectional images, for presentation of information to the user allowing them to identify the margins of a lesion based on visual differences between the lesion and the surrounding endogenous tissue. These visual differences could be observed or inferred by the surgeon/user based on their knowledge of laryngeal tissue types and disease pathology.

Figure 10:
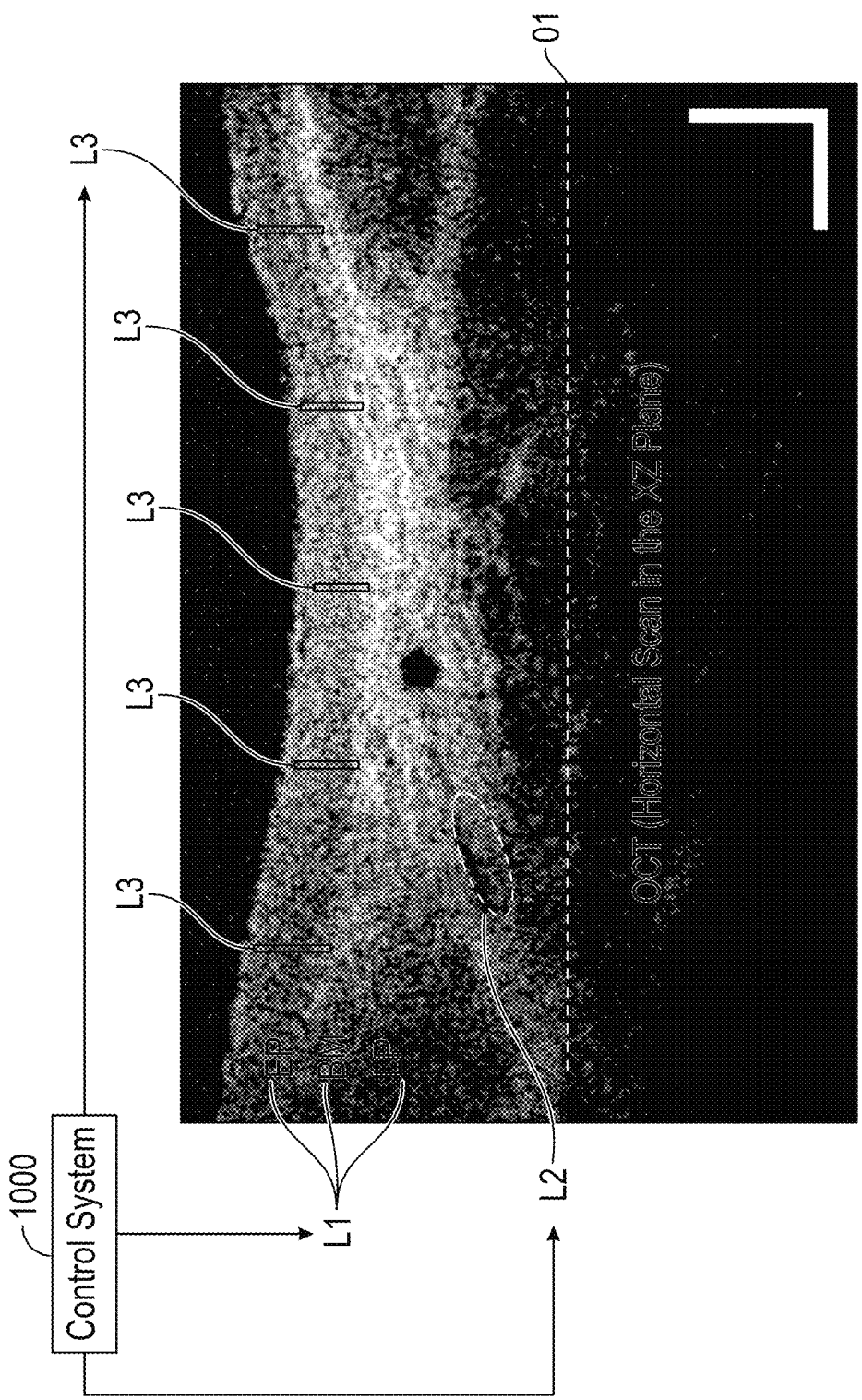
FIG. 10 shows an illustrative example of a visual presentation that can be used to provide image-guided laser surgery.

FIG. 10 shows an illustrative example of a visual presentation that can be used to provide image-guided laser surgery. In reference to FIG. 10, visual differences could be presented to the user in different ways. For example, on a representative cross-sectional OCT image O1, different tissue layers could be identified with labels L1; distinct structures, such as lesions, could be visually demarcated using borders such as label L2; vertical lines identifying the depth of a layer by label L3. Different layers or structure identification could also be presented to the user using color coding. The labels L1, L2, and L3 can be generated by the control system 1000 performing one or more of image segmentation and edge detection techniques.

Figure 11:
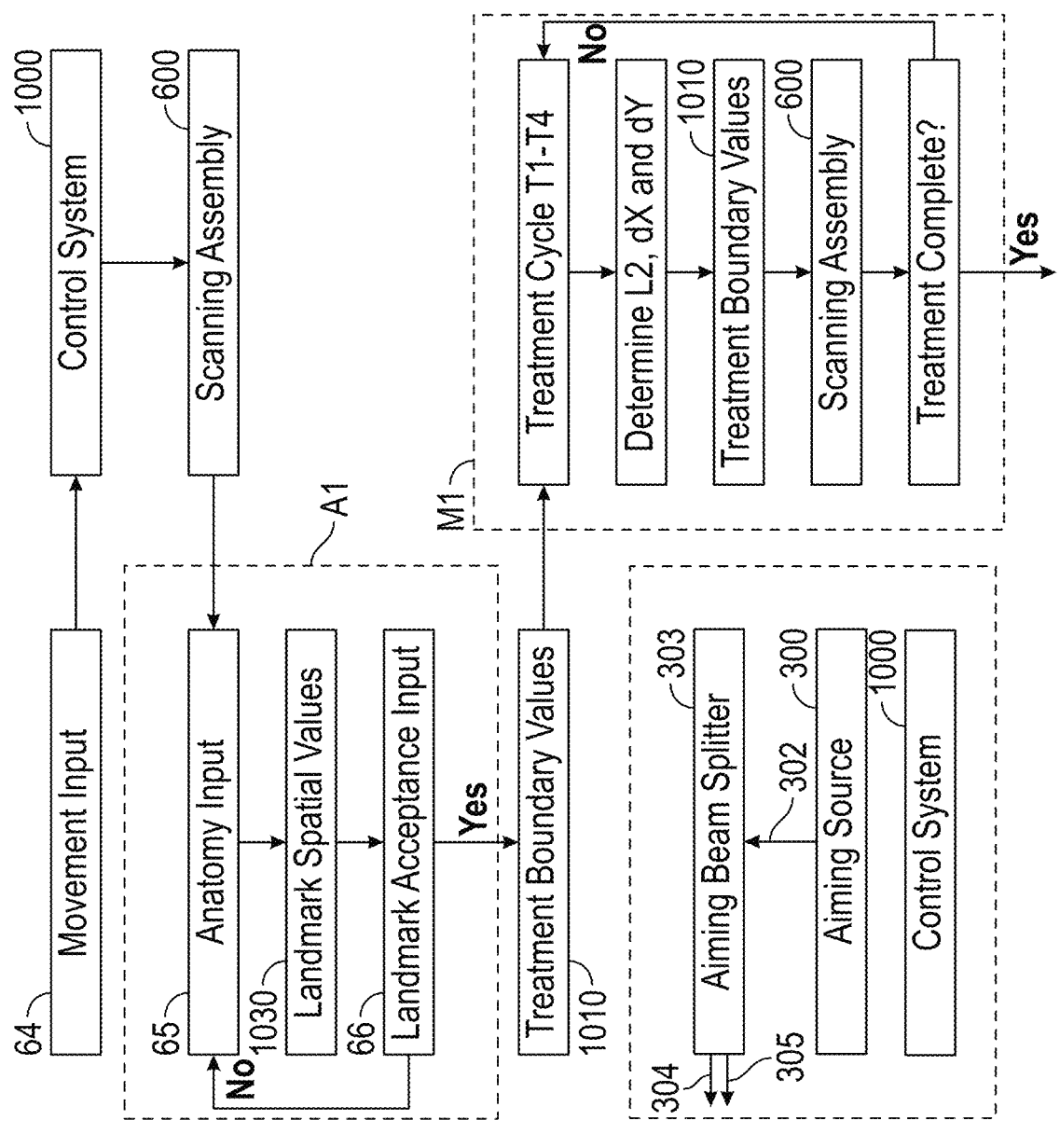
Figure 11:
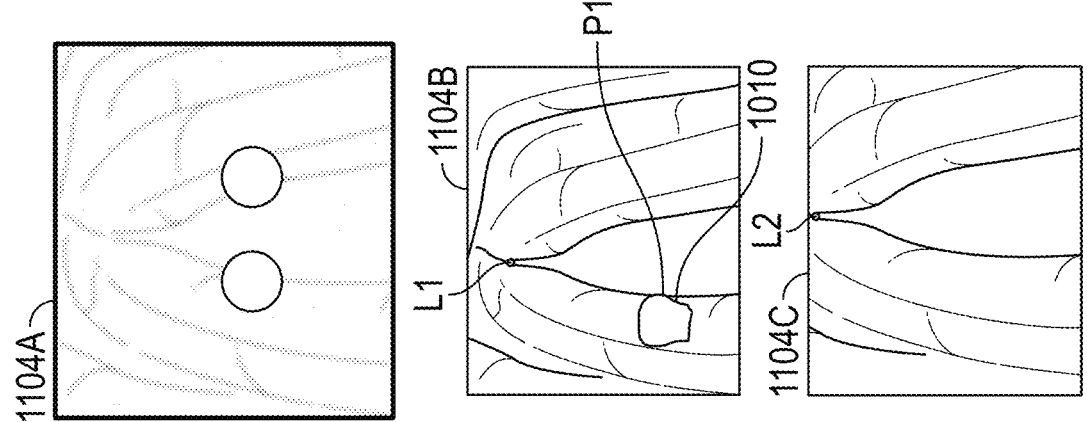

FIG. 11 shows an illustrative example of respective visual presentations that can be used to provide image-guided laser surgery, such as including acquiring focus to visualize a tissue surface and establishing a two-dimensional treatment area. During operating room (OR) laryngeal surgery, patients are anesthetized. As such, patient movement exists but is dramatically less than if the patient were awake. One advantage of ultrafast laser tissue processing is precision, which is on the order of the focused spot size, such as around 5 μm to 50 μm. Accordingly, anesthetized movement, while dramatically less than if a patient is awake, is still much larger than the ultrafast laser precision. Several methods are proposed for motion compensation for laryngeal tissue surgery. For example, a system can receive input (via user action) to turn an aiming beam on. With reference to the illustrative example of FIG. 11, a single collimated aiming beam 302 can be split passively by an optical element 303 into two collimated beams 304 and 305 that have equal intensity and that are spatially separated. For example, the splitter 303 can be a piece of optically transparent material, such as glass, that creates two equal intensity beams through coating of its surfaces and achieves a desired separation through the glass thickness and angle. In reference to FIG. 7A and FIG. 7B, the two aiming beams 304 and 305 propagate through the beam combiners 500, scanning assembly 600, optical system 700, laryngoscope 800 and onto the treatment site 900. The treatment site is illuminated by illumination beam 402 and the treatment site 900 imaged by the visualization assembly 400.

In reference to FIG. 11, the treatment site visualization can be presented to the user via the camera/imager display 1104. As shown in display 1104A, when the treatment site is out-of-focus, then two distinct spots are seen. In reference to FIG. 5B, FIG. 7A. FIG. 7B, and FIG. 11, as the control system 1000 is presented with the focus input 60 to adjust the focus optics 701, then image quality improves until an in-focus image 1104B is acquired. As this focus is approached, the two aiming beams 304 and 305 can spatially converge; the location on the tissue in image display 1104B where the two aiming beams 304 and 305 converge corresponds to that surface coinciding with the aiming beam convergence. In such a manner, the two aiming beams provide a means for locating the laryngeal tissue surface and therefore provide a marker or reference for motion compensation. The converged location of the two aiming beams can be adjusted, which is accomplished after the control system receives a scanning movement input 64. For example, the scanning assembly can move the aiming beams 304 and 305 to the location Xnew, Ynew as defined by the global co-ordinate system 2000. In reference to FIG. 9 and FIG. 5B, the control system 1000 can continue to be presented with movement inputs 64 until a surgery acceptance input is received and the scanning movement input 64 is disabled.

In reference to FIG. 11, manual input or automated feature recognition can be used to identify a target landmark (such as a candidate visible location for acceptance by a user) that will be present in any image of the targeted anatomy. For example, in a laryngeal context, the target could be an anatomical landmark such as the vocal cord medial edges, ventricular fold, or anterior or posterior commissure. The control system could receive an anatomy input 65 of which anatomical feature to identify such a feature. The control system can represent the landmark as a dataset of spatial information referenced to the global coordinate system. For example, landmark spatial values 1030 could be a line for the vocal cord medial edges or ventricular folds, or a single location for the anterior or posterior commissures. The control system 1000 can graphically presents to the user an indication depicting the landmark. The control system 1000 can be presented with a landmark acceptance input 66 accepting or rejecting this landmark. If the landmark acceptance input 66 is negative, then the anatomy input loop A1 can be repeated. In reference to FIG. 5C and FIG. 11, if the landmark is accepted then the control system 1000 can determine the treatment boundary values 1010 corresponding to a selected two-dimensional treatment region. The treatment protocol comprising T1 through T4 (or specified portions thereof) can then be initiated.

The control system 1000 can log the time during the treatment cycle, such continuously or at a specified discrete temporal resolution. A location of the landmark can be re-evaluated after a specified time duration, $t_{motion}$, and the position of the ultrafast laser beam can be adjusted by the scanning assembly 600 to track motion in the two dimensions corresponding to visualization field-of-view. For example, relative to the image field-of-view, the treatment site and therefore the original landmark location L1 may be in a different, new position L2, as shown in 1104C. In other words, L2 will have different spatial data than L1. The horizontal and vertical spatial differences, Dx and Dy, between L1 and L2 can be determined, and the treatment boundary values 1010 evaluated and ultrafast laser adjusted (e.g., translated in this illustrative example) by the same difference. The motion compensation routine M1 can continue until the treatment is complete.

A movement of L2 compared to L1, which is equivalent to the treatment site moving relative to the fixed image field-of-view, could occur due to patient breathing or the tissue being manually manipulated by a surgeon using cold steel tools. The time duration could be specified based on physiological factors such as patient motion during breathing under anesthesia. In this case, the time duration could be defined as some fraction of the time taken for a breath under anesthesia; breathing rates under anesthesia are approximately 8-12 breaths per minute (5-7.5 seconds per breath). In reference to FIG. 5C, the duration of a single treatment loop comprising T1 through T4 is generally a function of spot size, scanning frequency and laser repetition rate. In one illustrative example, during excision cycle T1 spot size=28 µm, R1=70 kHz and E1=200 µJ and during the hemostatic cycle spot size=28 µm, R2=225 kHz and E2=200 µJ. With these settings, for a 5 mm×5 mm×5 mm excision, the time to complete an excision treatment T1 is 275 ms and hemostatic treatment T3 is 1.2 seconds. Therefore, one treatment protocol is approximately 20-30% of a breath. In another approach, the time duration could be specified such that the interval is sufficiently short that any type of perturbation could be captured.

Figure 12:
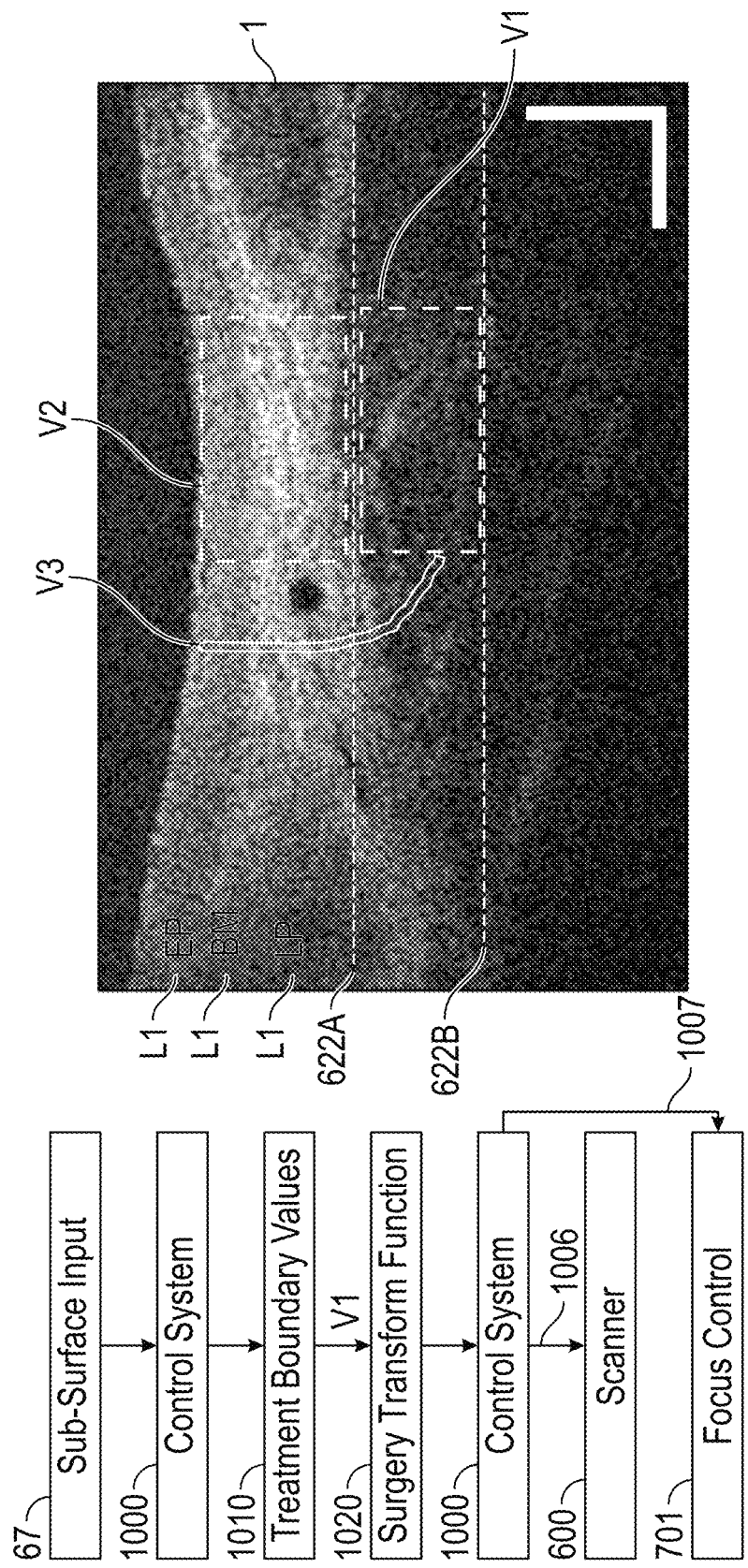
FIG. 12 shows an illustrative example of a visual presentation that can be used to provide image-guided laser surgery including use of a cross-sectional representation of a tissue region.

FIG. 12 shows an illustrative example of a visual presentation that can be used to provide image-guided laser surgery including use of a cross-sectional representation of a tissue region. FIG. 12 illustrates generally a capability of approaches described in this document for use in modifying (e.g., excising) a first region of tissue V1 very precisely without necessarily excising a second region of tissue V2 that the ultrafast laser passes through to reach the first region of tissue. Like the process described in relation to FIG. 5B, this can be accomplished by using a cross-sectional OCT image O1 to programmatically guide the ultrafast laser. As an example, the control system 1000 is presented with a geometry-based sub-surface input 67 that represents the region of tissue V1 that selected for removal (or other treatment). In reference to FIG. 5C and FIG. 12, the control system 1000 converts the geometry input 61 and sub-surface input 66 into treatment boundary values 1010. The first region of tissue V1 can be defined by the two-dimensional surface input 61 and a first depth 622A and a second depth 622B. Calibration can link the OCT field-of-view to the focus control, such that the control system 1000 can compute the focus control range required to remove tissue between depths 622A and 622B. A surgery transform function 1020 is applied, which provides control signals 1006 and 1007 to move the scanners 600 and the focus optics 701 respectively to remove a region of tissue coinciding with the sub-surface input 67.

Ultrafast laser excision ionizes tissue converting it to gas. For full volume excisions which start at the surface, the gas can easily escape. However, for sub-surface excisions such as V1, this gas could be trapped and could inhibit the excision process. Accordingly, the present inventors have also recognized, among other things, that single or multiple vent or port holes V3 can be formed in tissue (such as using ultrafast surgical laser excision) to allow ionized gas to escape or to otherwise facilitate pressure equalization. Alternatively (or in addition) another method for dissipation of ionized gas buildup is to deliberately introduce a delay after respective treatment cycles to allow gas to naturally dissipate or diffuse in the surrounding tissue.

Laryngoscope

As previously described, the surgical techniques and related apparatus described herein can convey an ultrafast surgical laser beam through an elongate member. The elongate member can include a catalog laryngoscope, such as the Benjamin or Kleinsasser models, or use of a customized model. For catalog laryngoscopes, a surgical sheath including different combinations of system elements as described above in various examples, can be insertable and removable from a laryngoscope. This provides a surgeon with versatility to transform the laryngoscope for OCT-guided ultrafast laser surgery by inserting the surgical sheath, or to use its original form for other, non-ultrafast laser purposes by detaching the surgical sheath. As another example, the system elements described herein can be included in a free-standing surgical head as shown in FIG. 7A and FIG. 7B.

Multimodal Operation

Generally, ultrafast laser surgical devices operate in a regime that results in very minimal tissue heating. Assuming a linear horizontal raster scan, a scanning frequency determines a corresponding linear speed on the image plane, given by:

$$v_{mirror} = 2 * L * f_{scan}$$

where L is the length of the scan and $f_{scan}$ is the scanning frequency.

When $f_{scan}$ represents a maximum scanning frequency, $f_{scan}$ is a count of how many times per second, a scanning element can move a laser beam along a length L and back, in the opposite direction along length L once more, to its original position. This expression is generally confined to a linear region, with constant velocity, and does not apply to the "turn around" regions where the mirror decelerates to a zero velocity and then accelerates in the opposite direction until reaching a constant velocity. This "turn around" time is generally a function of the scanning element's step response and linear speed. For example, MEMs mirrors have longer latency than galvanometer mirrors, with step responses approximately ten times that of galvanometer mirrors. The treatment zone where photodisruption or plasma-induced ablation is established can correspond to the linear region if the laser is deliberately blanked during the "turn around."

If a spot separation is represented by dx and the laser repetition rate is represented by f, then if the maximum scanning speed, $v_{mirror}$, is less than or equal to dx*f then each discrete scanned location can experience less than or equal to one laser pulse. However, in the case that $v_{mirror}$ is less than dx*f, then each scanned site can experience more than one laser pulse; as f increases, the count of pulses at each site can also increase. In other words, if the scanning speed is too low then the beam cannot be physically separated from successive pulses. In this latter case, the tissue does not fully cool between laser pulses and a cumulative temperature rise can occur; sufficiently high repetition rates could lead to thermal modification of the tissue.

Additionally, a temperature rise magnitude can be affected by one or more of: laser parameters such as higher energies per pulse, longer pulse durations, higher repetition rate or shorter wavelength; scan parameters such as lower scan frequencies; optical characteristics such as spot size; and tissue properties such as absorption and scattering coefficients and water fraction, which affects thermal conductivity. Therefore, for a given tissue type, selection of laser and hardware parameters can allow for deliberate, spatially controlled temperature rises. In an illustrative example, the laser repetition rate can then be altered to permit multi-modal surgical functionality: 1) low repetition rates for precise cutting (e.g., tissue excision using photodisruption) with very tight thermal confinement and negligible thermal rise and 2) much higher, for example 10-20×, repetition rates to induce hemostasis or other tissue modification.

A surgery could involve a protocol comprising a series of cutting and hemostasis enhancement cycles. For example, during the excision phase, a series of $N_{cut}$ cutting cycles with repetition $f_{cut}$ where the laser has a prescribed scan pattern with dimensions length L and width W, can excise a volume of tissue L×W×T, where T is the layer thickness. The cutting phase can be followed by a series of hemostatic cycles, where the surface area L×W would be scanned over $N_{hemo}$ cycles with a repetition rate $f_{hemo}$, where $f_{hemo} > f_{cut}$. This two-stage process would first precisely cut tissue with thermally induced damage to unexposed tissue, and then secondly enhance hemostasis (for example through coagulation) the treatment area with heat accumulation confined only to the surface.

As an illustration, a cumulative temperature rise due to multiple ultrafast laser pulses per site can be estimated by applying a two-dimensional heat equation. Assumptions include: 1) constant tissue optical properties (thermal conductivity, absorption and scattering properties do not change with laser exposure), 2) the laser is focused on the surface with spot radius, $r_{spot}$, with a Gaussian profile and 3) the only form of heat transfer is via conduction (radiation and convection are neglected). For a radial coordinate, r, and a depth coordinate, z, an estimated temperature distribution can be represented by:

$$T(r, z) = \frac{[(\mu_a[\lambda] + \mu_s'(\lambda)]AE\alpha}{k\pi r_{spot}^2} \exp\left(\frac{r^2}{r_{spot}^2}\right) \exp[(-\mu_a(\lambda) + \mu_s'(\lambda))z]$$

Tissue is a turbid medium where pa can represent an absorption coefficient and µ's can represent a reduced scattering coefficient. The variable E can represent an energy per pulse, A can represent an absorptivity (a fitted parameter), α can represent a thermal diffusivity, and k can represent a thermal conductivity.

The reduced scattering coefficient takes into account anisotropic tissue scattering because tissue is highly forward-scattering. An inverse of $\mu_a$ and µ's indicates a mean free path until an absorption or a scattering event, respectively. These values are generally wavelength and tissue type dependent; at wavelengths nominally emitted by ultrafast laser sources (e.g., 800 nm to 1100 nm), scattering dominates absorption with typical tissue values of µ's ranging from about 10-15 $cm^{-1}$ and $\mu_a$ ranging from about 0.1-0.5 $cm^{-1}$, such that a mean free path between scattering events is approximately 1 mm and mean free path between absorption events is 10 mm.

A thermal conductivity of tissue is a function of fractional tissue water content, $\rho_w$:

$$k = 0.06 + 0.57\rho_w \left[\frac{W}{m \cdot K}\right]$$

A thermal diffusivity is approximately the same for most tissues, and taken to be $1.4 \times 10^{-7}$ m²/s. Approximately, a temperature rise at a surface after the impact of N pulses with laser repetition rate R at the time of the arrival of the (N+1)th pulse can be represented by:

$$\Delta T(r, z, N) = \exp[(-(\mu_a(\lambda) + \mu_s'(\lambda))z]$$

$$\frac{[\mu_a(\lambda) + \mu_s'(\lambda)]AE}{k\pi r_{spot}^2} \alpha \sum_{i=1}^{N} \frac{r_{spot}^2}{(r_{spot}^2 + 4\alpha i/R)} \exp\left(-\frac{r^2}{(r_{spot}^2 + 4\alpha i/R)}\right)$$

For a particular set of parameters (e.g., repetition rate, energy per pulse) and tissue type, the expression above can represent a co-efficient corresponding to a maximum temperature rise, obtained at a center of the focused spot on the surface (where r=z=0, and where the exponential terms are unity). The first exponential term in the expression above captures temperature decay with depth, and the summation term captures the effect of successive pulses.

Figure 13A:
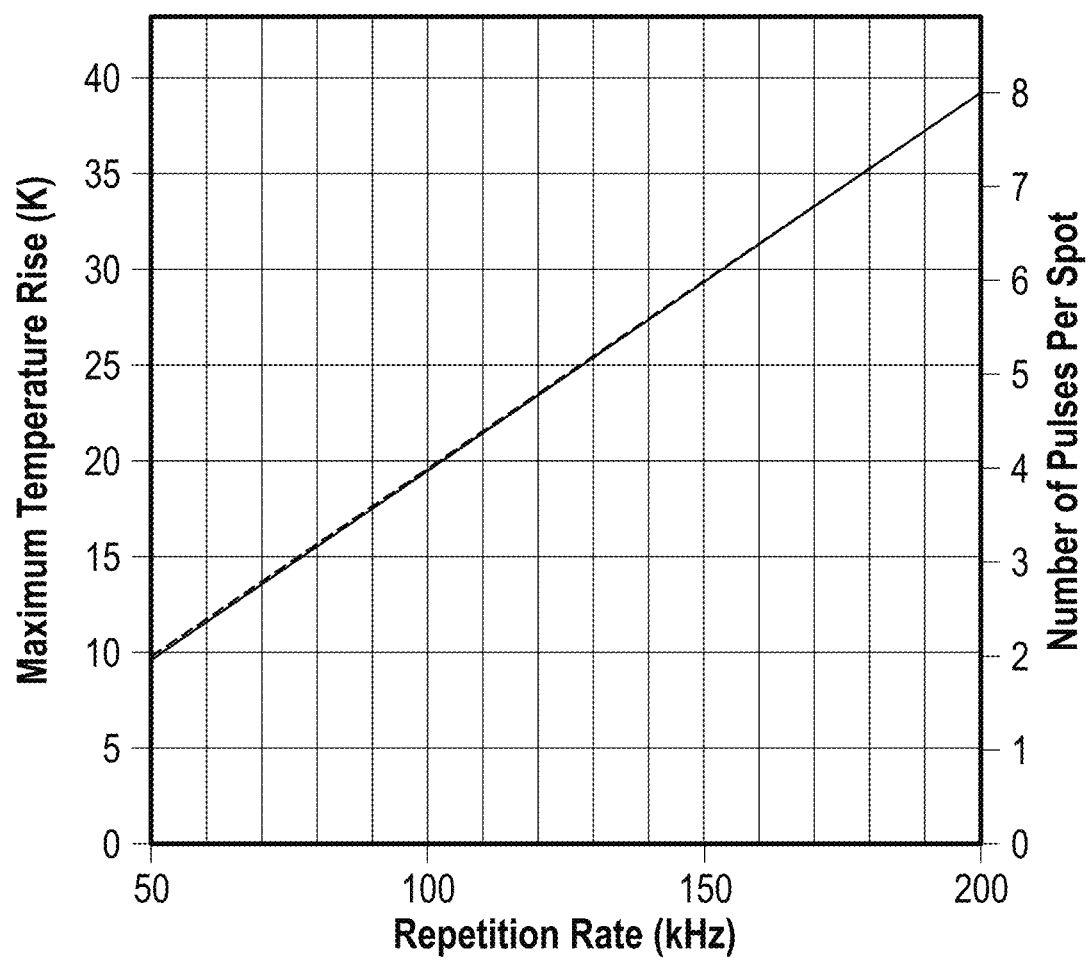
FIG. 13A shows an illustrative example comprising a relationship between tissue temperature rise and pulse repetition rate.

FIG. 13A shows an illustrative example comprising a relationship between tissue temperature rise and pulse repetition rate. FIG. 13A is a dual y-axis plot of a simulation, showing how the maximum temperature rise and count of pulses per spot changes with laser repetition rate (x-axis). Coagulation occurs at 60 C, for a temperature rise of approximately 23 degrees. Without being bound by theory, the simplified analysis herein suggests that for expected surgical parameters (e.g., a 3.5 mm cut, a spot separation of 30 µm, a 50 Hz scan frequency, 30 µm diameter focal spot and 200 µJ energy per pulse), a repetition rate of approximately 115 kHz is the threshold to achieve coagulation.

Figure 13B:
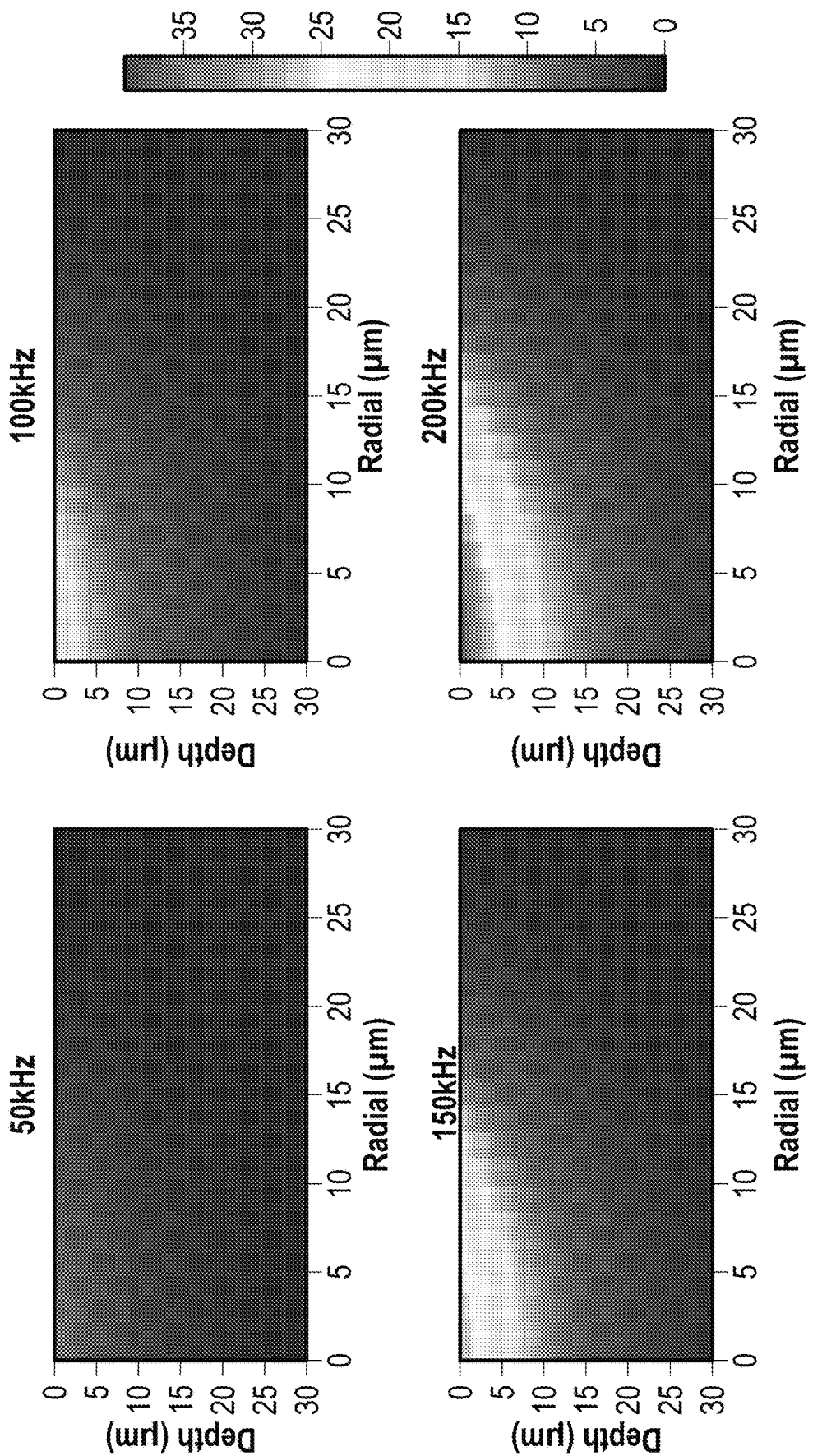
FIG. 13B shows a series of different numerically simulated heat maps showing a relationship between pulse repetition rate and spatial extent of elevated temperature.

FIG. 13B shows a series of different numerically simulated heat maps showing a relationship between pulse repetition rate and spatial extent of elevated temperature. The two-dimensional heat maps are computed over a range of repetition rates obtained by numerically evaluating the expression above. As the repetition rate increases, radial and depth diffusion increases; however, even at a maximum repetition rate of 2000 kHz, with 8 pulses at the spot, there is still very tight spatial confinement.

Distal Scanning Delivery System

The examples discussed above generally involve line-of-sight scanning, with free-space trajectory of an ultrafast laser beam through a channel in a structure such as a surgical sheath or other elongate instrument. Other approaches can be used. For example, distal ultrafast and OCT beam delivery and scanning can be performed, with HCF and single mode fibers traveling through a channel of an elongate structure, such that a distal end of HCF and single mode fibers are located much closer to the tissue (distal with respect to an ultrafast laser source and at or nearby a tissue site).

Figure 14A:
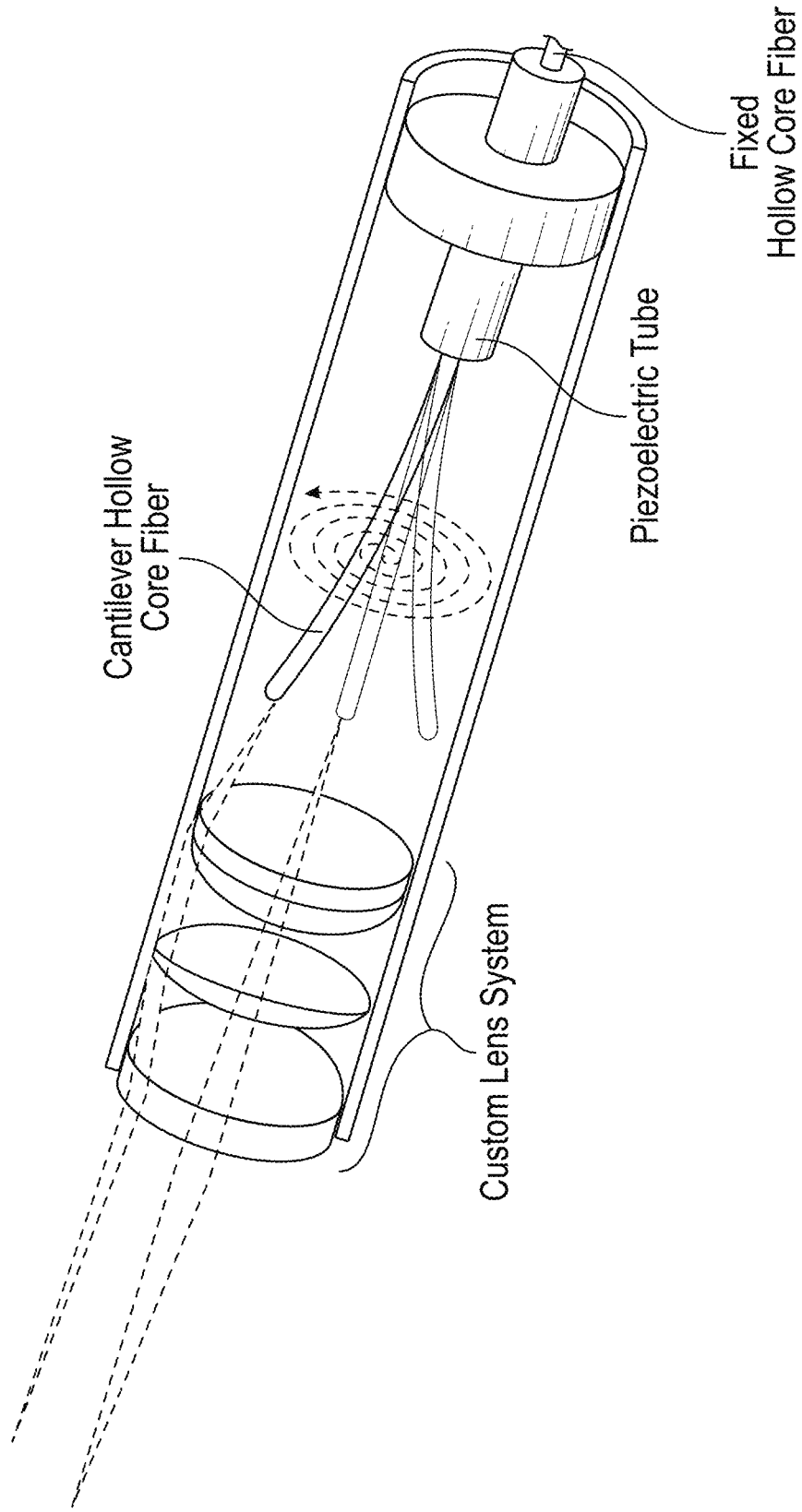
FIG. 14A shows an example comprising a cantilevered fiber-optic distal scanning configuration that can be used for delivery of a surgical laser beam to a tissue site.

FIG. 14A shows an example comprising a cantilevered fiber-optic distal scanning configuration that can be used for delivery of a surgical laser beam to a tissue site. As shown illustratively in FIG. 14A, a multi-modal fiber bundle carrying ultrafast surgical laser and OCT beams can be inserted through an operating lumen, such as a channel through which cold steel instrumentation may also pass. As an illustrative example, an endoscopic laser surgical apparatus can include a compact scanning system within the endoscope, with the scanning apparatus located at the distal end. Such a scanner configuration generally differs from the examples of FIG. 7A, FIG. 7B, and FIG. 7C, where scanning is performed more proximally with respect to a laser source.

In this configuration, shown illustratively in FIG. 14A, an HCF can be cantilevered and the free end fiber tip is deflected by vibrating the fiber. The actuation source can be piezoelectric as shown in FIG. 14A; however, electromagnetic, electrothermal, shape memory alloy, or an electroactive ionic polymer could also be used to perform actuation. A continuous deflection profile can be modeled as a series of discrete field points comprising an object and a finite conjugate imaging system established, with the desired magnification, to create a high-quality, low distortion and diffraction-limited scanned field-of-view on the tissue plane. Generally, the fiber is excited to elicit a mechanical resonance because this can produce the largest tip deflection. A first resonant frequency can be represented by:

$$f_1 = \frac{1.875}{4\pi} \sqrt{\frac{M}{\rho}} \frac{R_C}{L_C^2},$$

where M, $\rho$, $R_c$ and $L_c$ represent the Young's modulus, density, radius, and length of the cantilever, respectively. For the material properties generally associated with hollow core fibers, first-mode fiber resonances from approximately 1 to approximately 10 kHz are expected.

Piezoelectric materials possess electromechanical coupling such that an applied electric field results in mechanical deformation (with the reverse also being true: mechanical stress generates electric charge). In the illustrative example of FIG. 14A, a piezoelectric tube is shown. In this example, piezoelectric tube deformation resonantly drives a cantilevered hollow core fiber and can be used to produce two-dimensional scanning of a focused ultrafast laser beam. In a quadrant electrode configuration, the PZT can be selectively displaced in three axes: radial, axially, or laterally.

At voltages appropriate for medical device use, tube end deflections can be extremely small, on the order of tens of micrometers. For example, a PZT-5H material has a deflection constant of approximately 0.35 micron/V. These deflections are so small, they can be treated approximately as pure translation. However, when the PZT is sinusoidally driven with a frequency close to the first resonant mode of the hollow core fiber, the deflections of a cantilevered HCF fiber tip can be amplified by an order of magnitude or more, resulting in HCF fiber tip deflections of several hundred micrometers. This configuration can provide various aspects: 1) resonantly driven scanning of a focused ultrafast beam to process tissue as discussed above and below, 2) scanning of the ultrafast beam in conjunction with OCT scanning, with the OCT beam delivered within the same HCF, or separately, and 3) an image-guided surgical tool contained within a larger elongate member such as a surgical sheath.

A piezoelectric tube actuator, with a quadrant electrode arrangement, can establish a 2D motion range with a spiral scanning pattern. Such an electrode and scanning configuration can combine low power consumption, wide operating frequency range, and relatively low cost. Piezoelectric materials generally exhibit hysteresis in open loop (~10-15%), which could present challenges as the scanning field-of-view may not be sufficiently controlled in such an open-loop operational mode. Closed loop operation can significantly reduce hysteresis or eliminate it entirely.

Figure 14B:
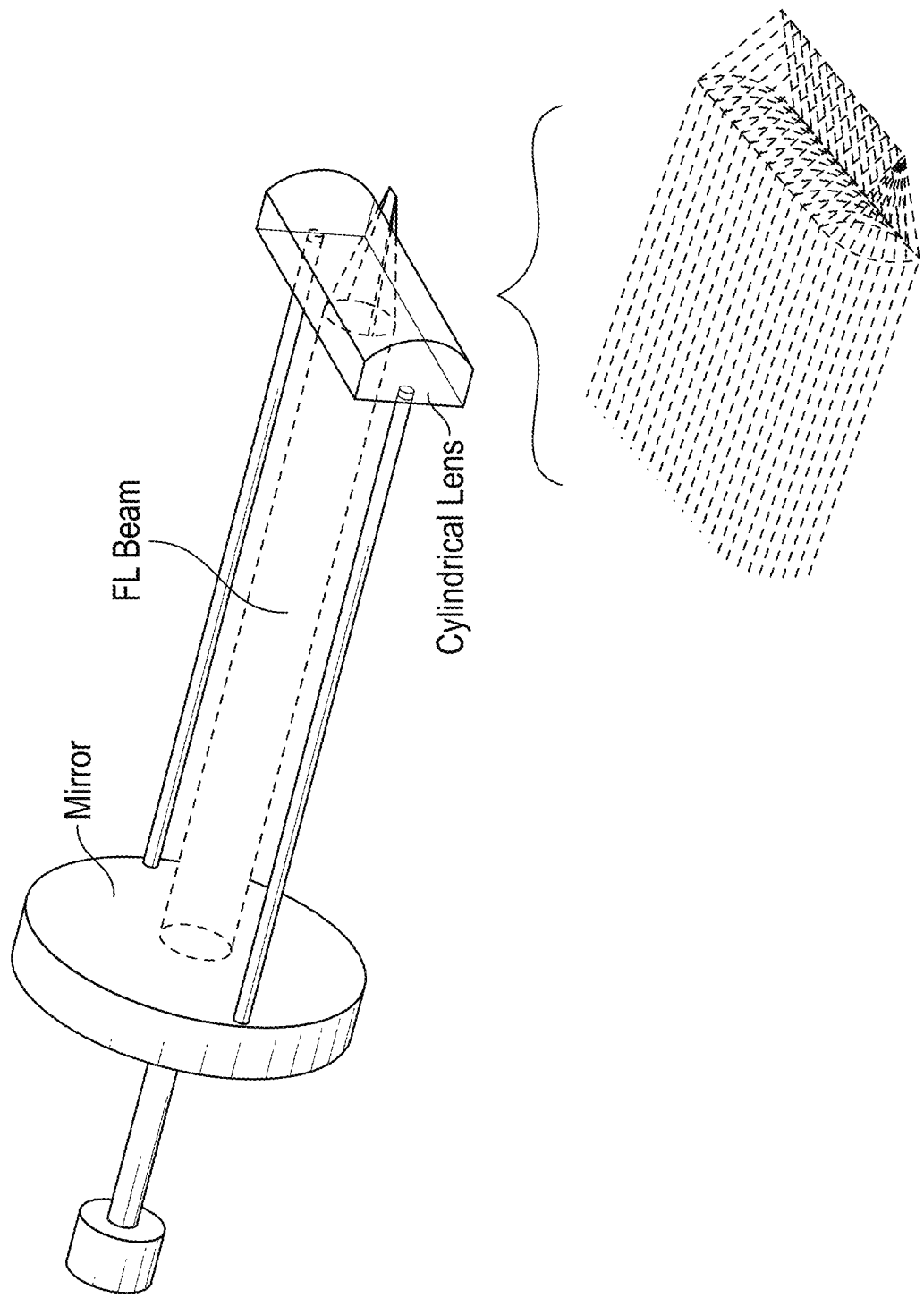
FIG. 14B shows an example comprising a cylindrical lens distal scanning configuration that can be used for delivery of a surgical laser beam to a tissue site.

FIG. 14B shows an example comprising a cylindrical lens distal scanning configuration that can be used for delivery of a surgical laser beam to a tissue site. Yet another scanning configuration is shown in FIG. 14B, such as for scanning at a distally-located portion of the laser surgery optical system at or nearby tissue. The configuration shown in FIG. 14B comprises a rotating cylindrical lens. A cylindrical lens focuses light in one axis, producing a line, and rotation can revolve this focused line, producing a circular footprint. The cylindrical lens can be recessed inside a tubular housing, providing a "stand-off" distance such that the cylindrical lens is located at its focal point away from tissue. In an example, a tubular housing for the scanner can be protected by an end cap, which slides over, and mates to, the housing. The mating feature can include a slide, lock, twist, bayonet, threaded or other configuration that securely attaches the end cap to a tubular housing and is detachable. The end cap comprises a transparent material, which can be placed in contact with tissue. The end cap material can include glass or plastic and can provide a sterile barrier and interface between the probe and tissue. Additionally, the end cap material can have refractive power, such as providing an element in the optical path to achieve a diffraction-limited line or other specific optical performance. The end cap can support one-time use only or can be sterilizable.

As successive layers of tissue are excised, the surgeon can re-position the laser beam delivery device (e.g., "surgical probe") so that a specified stand-off distance is established or maintained. As described below, the operation of the probe can include multi-modal, cycling between cutting and hemostatic modes, or operating at a single mode that combines excision and hemostasis. In this fashion, tissue can be removed in the oral cavity, pharynx, or larynx, as illustrative examples.

Surgical Parameters

Various examples above mentioned that a variety of ultrafast laser surgery system parameters can be used to facilitate one or more of tissue excision or hemostasis (e.g., coagulation of blood), such as in a mode-selective manner. TABLE I, below provides illustrative (but non-restrictive) examples of various parameter ranges that may be suitable for system capabilities to facilitate at least tissue excision, or a combination of tissue excision and hemostasis in a mode-selective manner, such as guided by OCT imaging or other surgery guidance or diagnostic techniques facilitated by OCT combined with ultrafast laser beam delivery. In one approach, mode selection can be achieved by controlling a photodisruptively-induced or plasma-induced ablation temperature rise locally at a tissue site, such as by selecting or otherwise controlling a nominal temperature rise. For example, a temperature rise can be selected from a range of 5 degrees to 60 degrees Celsius, such as relative to a baseline temperature.

TABLE I

Illustrative example of parameters that can be adjusted and related ranges.

| PARAMETER | RANGE |
| --- | --- |
| Ultrafast Laser Pulse Duration | 10 fs to 1 ns |
| Ultrafast Laser Wavelength | Up to 2500 nm |
| Surgical Fluence (on target, J/cm$^2$) | 0.5-150 |
| OCT Center Wavelength | 800 nm-1600 nm |
| Surgical Optical System Numerical Aperture | Up to 0.25 |
| Laser Repetition Rate (kHz) | Up to 2000 |
| Scanning Frequency | 1 Hz-600 Hz |

Figure 15:
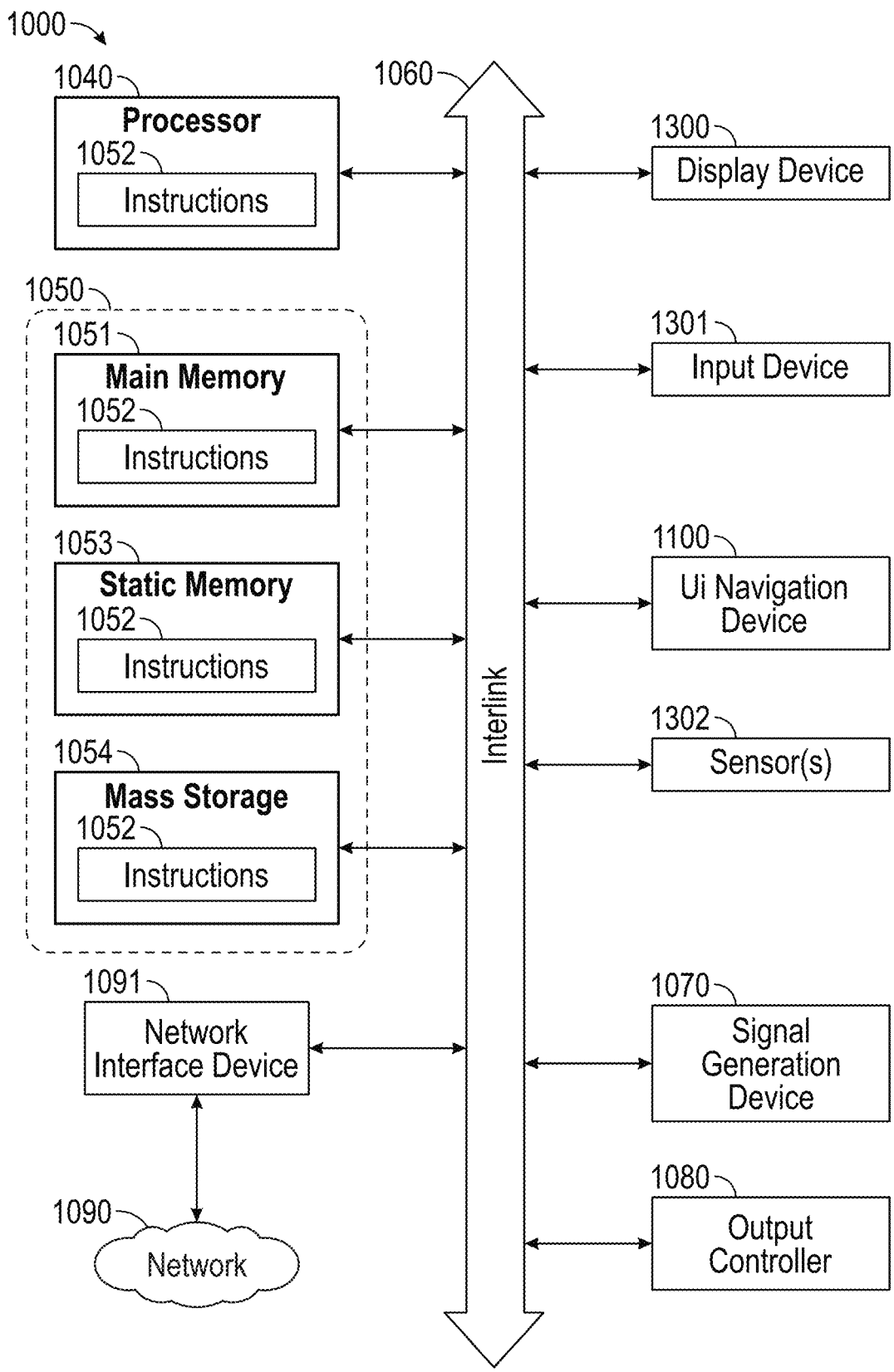
FIG. 15 illustrates a block diagram of an example comprising a machine or control system upon which any one or more of the techniques (e.g., methodologies) discussed herein may be performed.

FIG. 15 illustrates a block diagram of an example comprising a machine or control system 1000 upon which any one or more of the techniques (e.g., methodologies) discussed herein may be performed. Machine 1000 (e.g., computer system) may include a hardware processor 1040 (e.g., a central processing unit (CPU), a graphics processing unit (GPU), a hardware processor core, or any combination thereof), a main memory 1051 and a static memory 1053, connected via an interconnect 1060 (e.g., link or bus), as some or all of these components may constitute hardware for systems or related implementations discussed above.

Specific examples of main memory 1051 include Random Access Memory (RAM), and semiconductor memory devices, which may include storage locations in semiconductors such as registers. Specific examples of static memory 1053 include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; RAM: or optical media such as CD-ROM and DVD-ROM disks.

The machine 1000 may further include display devices 1300, an input device 1301 (e.g., a keyboard), and a user interface (UI) navigation device 1100 (e.g., a mouse). In an example, the display device 1300, input device 1301 and UI navigation device 1100 may be a touch-screen display. The control system 1000 may include a mass storage device 1054 (e.g., drive unit), a signal generation device 1070 (e.g., a speaker), a network interface device 1091, and one or more sensors 1302, such as a global positioning system (GPS) sensor, compass, accelerometer, or some other sensor. The machine 1000 may include an output controller 1080, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The mass storage device 908 may include a machine readable medium 1050 on which is stored one or more sets of data structures or instructions 1052 (e.g., software) embodying or utilized by any one or more of the techniques or functions described herein. The instructions 1052 may also reside, completely or at least partially, within the main memory 1051, within static memory 1053, or within the hardware processor 1040 during execution thereof by the control system 1000. In an example, one or any combination of the hardware processor 1040, the main memory 1051, the static memory 1053, or the mass storage device 1054 comprises a machine readable medium.

Specific examples of machine-readable media include, one or more of non-volatile memory, such as semiconductor memory devices (e.g., EPROM or EEPROM) and flash memory devices; magnetic disks, such as internal hard disks and removable disks, magneto-optical disks: RAM; or optical media such as CD-ROM and DVD-ROM disks. While the machine readable medium 1050 is illustrated as a single medium, the term "machine readable medium" may include a single medium or multiple media (e.g., a centralized or distributed database, or associated caches and servers) configured to store the one or more instructions 1052.

An apparatus of the machine 1000 includes one or more of a hardware processor 1040 (e.g., a central processing unit (CPU), a graphics processing unit (GPU), a hardware processor core, or any combination thereof), a main memory 1051 and a static memory 1053, sensors 1302, network interface device 920, antennas, a display device 1300, an input device 1301, a UI navigation device 1100, a mass storage device 1054, instructions 1052, a signal generation device 1070, or an output controller 1080. The apparatus may be configured to perform one or more of the methods or operations disclosed herein.

The term "machine readable medium" includes, for example, any medium that is capable of storing, encoding, or carrying instructions for execution by the machine 1000 and that cause the machine 1000 to perform any one or more of the techniques of the present disclosure or causes another apparatus or system to perform any one or more of the techniques, or that is capable of storing, encoding or carrying data structures used by or associated with such instructions. Non-limiting machine-readable medium examples include solid-state memories, optical media, or magnetic media. Specific examples of machine readable media include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks: Random Access Memory (RAM); or optical media such as CD-ROM and DVD-ROM disks. In some examples, machine readable media includes non-transitory machine-readable media. In some examples, machine readable media includes machine readable media that is not a transitory propagating signal.

The instructions 1052 may be transmitted or received, for example, over a communications network 1090 using a transmission medium via the network interface device 1091 utilizing any one of a number of transfer protocols (e.g., frame relay, internet protocol (IP), transmission control protocol (TCP), user datagram protocol (UDP), hypertext transfer protocol (HTTP), etc.). Example communication networks include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®). IEEE 802.15.4 family of standards, a Long Term Evolution (LTE) 4G or 5G family of standards, a Universal Mobile Telecommunications System (UMTS) family of standards, peer-to-peer (P2P) networks, satellite communication networks, among others.

In an example, the network interface device 1091 includes one or more physical jacks (e.g., Ethernet, coaxial, or other interconnection) or one or more antennas to access the communications network 1090. In an example, the network interface device 920 includes one or more antennas to wirelessly communicate using at least one of single-input multiple-output (SIMO), multiple-input multiple-output (MIMO), or multiple-input single-output (MISO) techniques. In some examples, the network interface device 1091 wirelessly communicates using Multiple User MIMO techniques. The term "transmission medium" shall be taken to include any intangible medium that is capable of storing, encoding or carrying instructions for execution by the machine 1000, and includes digital or analog communications signals or other intangible medium to facilitate communication of such software.

VARIOUS NOTES AND EXAMPLES

Each of the non-limiting examples below can stand on its own or can be combined in various permutations or combinations with one or more of the other aspects or other subject matter described in this document.

Example 1 comprises a system (or corresponding method) for performing depth-selective trans-oral laser beam delivery, the system comprising: a scanning assembly configured to co-scan respective beams in two axes, the respective beams comprising a surgical laser beam comprising monochromatic coherent pulsed light, an optical coherence tomography (OCT) beam comprising incoherent polychromatic light or coherent laser light having a varying wavelength, and a visible aiming beam; an optical system configured to controllably co-focus the respective beams including at least two visible aiming beam portions, including directing the at least two visible aiming beam portions trans-orally toward a tissue surface and conveying reflections of the visible aiming beam portions to a visualization imager: and a control system configured to: generate a presentation of a visible-light visualization of a tissue surface and the reflections of the visible aiming beam portions received by the visualization imager; acquire focus on the tissue surface as indicated by the respective visible aiming beam portions spatially converging in the generated presentation, by varying a focus of the optical system; and track motion in two axes using a visible feature in an in-focus generated presentation, for control of the scanning assembly.

In Example 2, the system of Example 1, wherein the optical system comprises an objective to convey the surgical laser beam to a treatment site and supporting visible light visualization by establishing at least two distinct visible light visualization optical pathways from the treatment site to respective visualization imagers to provide respective visualization perspectives.

In Example 3, the system of Example 1 comprises an ultrafast surgical laser source configured generate ultrafast pulses defined by having a duration from 10 femtoseconds to 300 picoseconds to generate the surgical laser beam for excising tissue, facilitating hemostasis, or both.

In Example 4, the system of Example 1, wherein the control system is configured to identify a candidate visible location for tracking, comprising an anatomical or artificial landmark; and wherein the visible feature is indicated graphically in the generated presentation.

In Example 5, the system of any of Examples 1 through 4, wherein the control system is configured to: receive an input defining a two-dimensional treatment area, in response to a presentation of a visible-light visualization of the tissue surface; and generate control data for actuating the scanning assembly to compensate for the tracked motion to scan the surgical laser beam across the two-dimensional treatment area.

In Example 6, the system of Example 5, wherein the control system is configured to: generate a presentation of a cross-sectional representation of a region below the tissue surface, the cross-sectional representation constructed using a scattered representation of the OCT beam conveyed by the optical system; and receive an input defining a depth range for treatment by the surgical laser beam, in response to the presentation of the cross-sectional representation of the region below the tissue surface.

In Example 7, the system of Example 6, wherein the control system is configured to contemporaneously present the visible light visualization and the cross-sectional representation to a user.

In Example 8, the system of any of Examples 6 or 7, wherein the control system, in response to the received inputs defining the two-dimensional treatment area and the depth range for treatment, is configured to generate control data defining cycles to modify and visualize tissue within a volume defined by the two-dimensional treatment area and the depth range, by actuating the optical system to focus on respective focal planes corresponding to different depths, and at respective depths, actuating the scanning assembly to scan the surgical laser beam and OCT beam across the two-dimensional area.

In Example 9, the system of any of Examples 6 through 8, wherein the control system is configured to: track motion in a third axis corresponding to a depth axis, using a feature in the cross-sectional representation; and generate control data for actuating the optical system to focus on respective focal planes corresponding to different depths including compensating for tracked motion in the third axis.

In Example 10, the system of any of Examples 6 through 9, wherein the cross-sectional representation of the region below the tissue surface shows regions in the cross-sectional representation corresponding to different tissue characteristics.

In Example 11, the system of any of Examples 1 through 10, wherein the tissue surface is located on or within false or true vocal fold tissue.

In Example 12, the system of any of Examples 1 through 10, wherein the tissue surface is located on or within a larynx.

In Example 13, the system of any of Examples 1 through 10, wherein the tissue surface is located on or within at least one of an oral cavity, an oropharynx, a hypopharynx, or a trachea.

In Example 14, the system of any of Examples 1 through 13, wherein the optical system is configured to establish the at least two aiming beam portions including splitting an aiming beam into the at least two portions and directing the at least two aiming beam portions to converge with each other at a specified focal location.

Example 15 comprises a system (or corresponding method) for performing depth-selective trans-oral laser beam delivery, the system comprising: a scanning assembly configured to co-scan respective beams in two axes to define a first addressable region, the respective beams comprising a surgical laser beam comprising monochromatic coherent pulsed light, and an optical coherence tomography (OCT) beam comprising incoherent polychromatic light or coherent laser light having a varying wavelength; an optical system configured to controllably co-focus the respective beams in a depth-selective manner; a movable platform comprising electrically-operated actuators configured to adjust an orientation of the scanning assembly and optical system to move the first addressable region within a larger second addressable region; and a control system configured to: control the movable platform using the electrically-operated actuators platform to align the first addressable region with a tissue region of interest; and generate control data for actuating the optical system to direct the respective beams trans-orally including focusing the surgical laser beam at respective focal planes corresponding to different depths, and at respective depths, actuating the scanning assembly to scan the surgical laser beam across a specified two-dimensional treatment area to excise tissue using at least one of plasma-induced ablation or photodisruption.

In Example 16, the system of Example 15, wherein the optical system comprises an objective to convey the surgical laser beam to a treatment site and supporting visible light visualization by establishing at least two distinct visible light visualization optical pathways from the treatment site to respective visualization imagers to provide respective visualization perspectives.

In Example 17, the system of any of Examples 15 or 16, comprising an ultrafast surgical laser source configured to generate the surgical laser beam for excising tissue, facilitating hemostasis, or both.

In Example 18, the system of Example 17, wherein the ultrafast surgical laser source is configured to generate ultrafast pulses defined by having a duration from 10 femtosecond to 300 picoseconds.

In Example 19, the system of any of Examples 15 through 18, wherein the movable platform is configured to adjust the orientation with at least two degrees of freedom comprising rotation in a pitch direction and rotation in a yaw direction, respectively.

In Example 20, the system of Example 15, wherein the respective beams comprise a visible aiming beam, the visible aiming beam comprising at least two aiming beam portions oriented symmetrically about a central axis.

In Example 21, the system of any of Examples 15 through 20, wherein the control system is configured to: generate a presentation of a cross-sectional representation of a region below a tissue surface, the cross-sectional representation constructed using a scattered representation of the OCT beam conveyed by the optical system; and receive an input defining a depth range for treatment by the surgical laser beam, in response to the presentation of the cross-sectional representation of the region below the tissue surface.

In Example 22, the system of Example 21, wherein the control system is configured to contemporaneously present a visible light visualization of the tissue surface and the cross-sectional representation of the region below the tissue surface to a user.

In Example 23, the system of any of Examples 21 and 22, wherein the control system is configured to receive an input defining a depth range for treatment by the surgical laser beam, in response to the presentation of the cross-sectional representation of the region below the tissue surface.

In Example 24, the system of Example 23, wherein the control system, in response to the received inputs defining the two-dimensional treatment area and the depth range for treatment, is configured to generate control data defining cycles to modify and visualize tissue within a volume defined by the two-dimensional treatment area and the depth range, by actuating the optical system to focus on respective focal planes corresponding to different depths, and at respective depths, actuating the scanning assembly to scan the surgical laser beam and OCT beam across the two-dimensional area.

Example 25 comprises a machine-implemented method for providing depth-selective trans-oral laser beam delivery, the method comprising: co-scanning, by a scanning assembly, respective beams in two axes, the respective beams comprising a surgical laser beam comprising monochromatic coherent pulsed light, an optical coherence tomography (OCT) beam comprising incoherent polychromatic light or coherent laser light having a varying wavelength, and a visible aiming beam; co-focusing the respective beams including at least two visible aiming beam portions, including directing the at least two visible aiming beam portions trans-orally toward a tissue surface and conveying reflections of the visible aiming beam portions to a visualization imager; generating a presentation of a visible-light visualization of a tissue surface and the reflections of the visible aiming beam portions received by the visualization imager; acquiring focus on the tissue surface as indicated by the respective visible aiming beam portions spatially converging in the generated presentation, by varying a focus of an optical system; and tracking motion in two axes using a visible feature in an in-focus generated presentation, for control of the co-scanning.

In Example 26, the machine-implemented method of Example 25, wherein the co-scanning and co-focusing include directing the respective beams trans-orally toward the tissue surface on or within at least one of an oral cavity, an oropharynx, a hypopharynx, a larynx, or a trachea.

In Example 27, the machine-implemented method of Example 25, wherein the co-scanning and co-focusing include directing the respective beams trans-orally toward the tissue surface located on or within a larynx corresponding to an epiglottis, a glottis, a sub-glottis, false or true vocal folds, muscle, cartilage, ligament, or bone.

In Example 28, the machine-implemented method of any of Examples 25 through 27, comprising: generating ultrafast pulses defined by having a duration from 10 femtosecond to 300 picoseconds to modify a volume of tissue; and visualizing the tissue by presentation of a cross-sectional representation of a region below the tissue surface, the cross-sectional representation constructed using a scattered representation of the OCT beam conveyed by the optical system showing different tissue morphology of a larynx comprising one or more of epithelium, basement membrane, or lamina propria defined by superficial, middle, or deep layers, or muscle.

Example 29 comprises a machine-implemented method for performing depth-selective trans-oral laser beam delivery, the method comprising: co-scanning, by a scanning assembly, respective beams in two axes to define a first addressable region, the respective beams comprising a surgical laser beam comprising monochromatic coherent pulsed light, and an optical coherence tomography (OCT) beam comprising incoherent polychromatic light or coherent laser light having a varying wavelength; controllably co-focusing, by an optical system, the respective beams in a depth-selective manner, adjusting, by electrically-operated actuators of a movable platform, an orientation of the scanning assembly and optical system to move the first addressable region within a larger second addressable region, including controlling the movable platform using the electrically-operated actuators to align the first addressable region with a tissue region of interest; and generating control data for actuating the optical system to direct the respective beams trans-orally including focusing the surgical laser beam at respective focal planes corresponding to different depths, and at respective depths, actuating the scanning assembly to scan the surgical laser beam across a specified two-dimensional treatment area to excise tissue using at least one of plasma-induced ablation or photodisruption.

In Example 30, the machine-implemented method of Example 29, wherein adjusting the orientation with at least two degrees of freedom comprises rotation about two axes to shift the first addressable region; and wherein the method comprises: modifying a laryngeal tissue volume within the first addressable region using the surgical laser beam generated by an ultrafast laser source with pulses having a duration from a range of 10 femtoseconds to 300 picoseconds; and visualizing, using a cross-sectional representation constructed using a scattered representation of the OCT beam conveyed by the optical system, a cross-sectional representation of the laryngeal tissue.

Example 31 comprises a system (or corresponding method) for performing depth-selective surgical laser beam delivery, the system comprising: a scanning assembly configured to co-scan respective beams in two axes, the respective beams comprising a surgical laser beam comprising monochromatic coherent pulsed light, an optical coherence tomography (OCT) beam comprising incoherent polychromatic light or coherent laser light having a varying wavelength; an optical system configured to controllably co-focus the respective beams in a depth-selective manner; an ultrafast surgical laser source configured to generate the surgical laser beam to modify a volume of tissue by excision or facilitating hemostasis, or both; and a control system communicatively coupled with the scanning assembly, the optical system, and the ultrafast surgical laser source, the control system configured to establish at least one characteristic of a focused pulse or focused pulses of the surgical laser beam as delivered to a tissue site to selectively enhance hemostasis.

In Example 32, the system of Example 31, wherein the control system is configured to enhance hemostasis by at least one of (1) increasing a count of focused pulses of the surgical laser beam striking a focal location or (2) decreasing a spatial separation between focused spots of the surgical laser beam, as compared to a mode corresponding to excising tissue where hemostasis is not enhanced.

In Example 33, the system of Example 31, wherein the control system is configured to enhance hemostasis by increasing a fluence associated with a spot striking a focal location by at least one of (1) adjusting an energy-per-pulse, (2) adjusting a spot size, or (3) adjusting a triggering mode of the ultrafast laser source as compared to a mode corresponding to excising tissue where hemostasis is not enhanced.

In Example 34, the system of Example 31, wherein the control system is configured to enhance hemostasis by adjusting a wavelength of the surgical laser beam to enhance molecular absorption.

In Example 35, the system of any of Examples 31 through 34, wherein the surgical laser source configured to generate ultrafast pulses defined by having a duration from a range of 10 femtoseconds to 300 picoseconds.

In Example 36, the system of any of Examples 31 through 35, wherein the control system is configured to control the optical system to controllably focus the surgical laser beam through a series of focal planes corresponding to different depths, bounded by an initial focal plane and final focal plane, to progressively modify a volume of tissue by actuating the scanning assembly to scan the surgical laser beam across a defined two-dimensional area without requiring excision or damage of tissue at depths other than the depth of a respective focal plane along a direction from which the surgical laser beam is delivered.

In Example 37, the system of Example 36, wherein the focal planes are below a tissue surface and the volume of tissue modified is entirely sub-surface.

In Example 38, the system of any of Examples 31 through 37, wherein the control system is configured to: generate a presentation of a cross-sectional representation of the tissue site, the cross-sectional representation constructed using a scattered representation of the OCT beam conveyed by the optical system; and receive an input defining a depth range for treatment by the surgical laser beam, in response to the presentation of the cross-sectional representation of a region below a tissue surface.

In Example 39, the system of Example 31, wherein the control system is configured to control the optical system to excise tissue to establish at least one vent or port to a sub-surface region beneath a tissue surface.

Example 40 comprises a system (or corresponding method) for performing surgical laser beam delivery, the system comprising: an ultrafast surgical laser source configured to generate a surgical laser beam for excising tissue, facilitating hemostasis, or both; an optical fiber coupled to the ultrafast surgical laser source and configured to deliver and focus light spanning at least a wavelength of the surgical laser beam, including delivering monochromatic coherent pulsed light of the surgical laser beam, comprising ultrafast pulses defined by a duration ranging from 10 femtoseconds to 300 picoseconds, to a tissue site; a scanning assembly configured to scan the light in a two-dimensional pattern; and a control system communicatively coupled with the scanning assembly and the ultrafast surgical laser source, the control system configured to establish at least one characteristic of a focused pulse or focused pulses of the surgical laser beam as delivered to the tissue site by the optical fiber, to selectively enhance hemostasis.

In Example 41, the system of Example 40, wherein the scanning assembly is located at or near the tissue site at a distal end of the optical fiber.

In Example 42, the system of Example 41, wherein the distal end of the optical fiber is cantilevered; and wherein the scanning assembly comprises an actuator mechanically coupled with the cantilevered optical fiber.

In Example 43, the system of any of Examples 40 or 41, wherein the scanning assembly comprises a cylindrical lens structure that is configured to rotate.

In Example 44, the system of Example 40, wherein the optical fiber is configured to deliver and focus an optical coherence tomography (OCT) beam comprising incoherent polychromatic light or coherent laser light having a varying wavelength; and wherein the control system is configured to generate a presentation of a cross-sectional representation of a tissue region at the tissue site, the cross-sectional representation constructed using a scattered representation of the OCT beam conveyed by the optical fiber.

In Example 45, the system of any of Examples 40 through 44, wherein light exiting a distal end of the optical fiber at the tissue site is focused by a refractive structure.

In Example 46, the system of any of Examples 40 through 44, wherein light exiting a distal end of the optical fiber at the tissue site is focused by a wavelength or sub-wavelength scale diffractive structure.

In Example 47, the system of any of Examples 40 through 46, wherein the optical fiber and the scanning assembly are housed by a protective sheath comprising a sterile outer barrier; and wherein at least an area of the protective sheath to be placed in contact with the tissue site is fluid-tight.

In Example 48, the system of Example 47, wherein the protective sheath is replaceable.

In Example 49, the system of any of Examples 40 through 48, wherein the optical fiber traverses at least a portion of an interior of an elongate instrument; and wherein the optical fiber comprises a hollow-core photonic crystal fiber, the hollow-core photonic crystal fiber defining a gas-filled hollow region to support optical propagation.

In Example 50, the system of any of Examples 40 through 49, wherein the control system is configured to enhance hemostasis by at least one of (1) increasing a count of focused pulses of the surgical laser beam striking a focal location or (2) decreasing a spatial separation between focused spots of the surgical laser beam, as compared to a mode corresponding to excising tissue where hemostasis is not enhanced.

In Example 51, the system of any of Examples 40 through 49, wherein the control system is configured to enhance hemostasis by increasing a fluence associated with a spot striking a focal location by at least one of (1) adjusting an energy-per-pulse, (2) adjusting a spot size, or (3) adjusting a triggering mode of the ultrafast laser source, as compared to a mode corresponding to excising tissue where hemostasis is not enhanced.

In Example 52, the system of any of Examples 40 through 49, wherein the control system is configured to enhance hemostasis by adjusting a wavelength of the surgical laser beam to enhance molecular absorption.

Example 53 comprises a machine-implemented method for performing depth-selective surgical laser beam delivery using a system comprising a scanning assembly, an optical system, an ultrafast surgical laser source, and a control system, the method comprising: co-scanning respective beams in two axes using the scanning assembly, the respective beams comprising a surgical laser beam comprising monochromatic coherent pulsed light, an optical coherence tomography (OCT) beam comprising incoherent polychromatic light or coherent laser light having a varying wavelength; controllably co-focusing the respective beams in a depth-selective manner using the optical system; generating the surgical laser beam to modify a volume of tissue by excision or facilitating hemostasis, or both; and establishing at least one characteristic of a focused pulse or focused pulses of the surgical laser beam as delivered to a tissue site to selectively enhance hemostasis using the control system.

In Example 54, the machine-implemented method of Example 53, wherein the tissue site is located on or within false or true vocal fold tissue.

In Example 55, the machine-implemented method of Example 53, wherein the tissue site is located on or within a larynx.

In Example 56, the machine-implemented method of Example 53, wherein the tissue site is located on or within at least one of an oral cavity, an oropharynx, a hypopharynx, or a trachea.

Example 57 comprises a machine-implemented method for performing surgical laser beam delivery using a system comprising an ultrafast surgical laser source, an optical fiber, a scanning assembly, and a control system, the method comprising: generating a surgical laser beam for excising tissue, facilitating hemostasis, or both using the ultrafast surgical laser source; delivering and focusing light spanning at least a wavelength of the surgical laser beam, including delivering monochromatic coherent pulsed light of the surgical laser beam, comprising ultrafast pulses defined by a duration ranging from 10 femtoseconds to 300 picoseconds, to a tissue site, using the optical fiber; scanning the light in a two-dimensional pattern; and establishing at least one characteristic of a focused pulse or focused pulses of the surgical laser beam as delivered to the tissue site by the optical fiber, to selectively enhance hemostasis.

In Example 58, the machine-implemented method of Example 57, wherein the tissue site is located on or within false or true vocal fold tissue.

In Example 59, the machine-implemented method of Example 57, wherein the tissue site is located on or within a larynx.

In Example 60, the machine-implemented method of Example 57, wherein the tissue site is located on or within at least one of an oral cavity, an oropharynx, a hypopharynx, or a trachea.

Example 61 comprises a system (or corresponding method) for performing depth-selective trans-oral laser beam delivery, the system comprising: a scanning assembly configured to co-scan respective beams in two axes, the respective beams comprising a surgical laser beam comprising monochromatic coherent pulsed light, an optical coherence tomography (OCT) beam comprising incoherent polychromatic light or coherent laser light having a varying wavelength; an optical system configured to controllably co-focus the respective beams and supporting visible light visualization; and a control system configured to: generate a presentation of a visible-light visualization of a tissue surface; receive an input defining a two-dimensional treatment area, in response to a presentation of a visible-light visualization of the tissue surface; generate a presentation of a cross-sectional representation of a region below the tissue surface, the cross-sectional representation constructed using a scattered representation of the OCT beam conveyed by the optical system; receive an input defining a depth range for treatment by the surgical laser beam, in response to the presentation of the cross-sectional representation of the region below the tissue surface; and generate control data defining cycles to modify and visualize tissue within a volume defined by the two-dimensional treatment area and the depth range, by actuating the optical system to focus on respective focal planes corresponding to different depths, and at respective depths, actuating the scanning assembly to scan the surgical laser beam and OCT beam across the two-dimensional area including delivering the surgical laser beam and OCT beam trans-orally.

In Example 62, the system of Example 61, wherein the control system is configured to contemporaneously present the visible light visualization and the cross-sectional representation to a user.

In Example 63, the system of any of Examples 61 or 62, wherein the optical system comprises an objective to convey the surgical laser beam and OCT beam trans-orally to a treatment site and supporting visible light visualization by establishing at least two distinct visible light visualization optical pathways from the treatment site to respective visualization imagers to provide respective visualization perspectives.

In Example 64, the system of Example 63, wherein the respective visualization perspectives are formed using finite conjugate optical arrangements sharing the objective.

In Example 65, the system of any of Examples 63 or 64, wherein the at least two distinct visible light visualization optical pathways include respective symmetrically-arranged peripheral regions of the objective.

In Example 66, the system of any of Examples 61 through 65, comprising a surgical laser source configured to generate ultrafast pulses defined by having a duration from a range of 10 femtoseconds to 300 picoseconds.

In Example 67, the system of any of Examples 61 through 66, wherein the control system is configured to control the optical system to controllably focus the surgical laser beam at one or more specified depths to perform tissue excision without requiring excision or damage of tissue at depths other than the specified depth along a direction from which the surgical laser beam is delivered.

In Example 68, the system of Example 67, wherein the one or more specified depths comprises a sub-surface depth beneath the tissue surface.

In Example 69, the system of any of Examples 67 or 68, wherein an initial depth of excision is sub-surface.

In Example 70, the system of any of Examples 61 through 69, wherein the control system is configured to control the optical system to excise tissue to establish at least one vent or port to a sub-surface region beneath the tissue surface.

In Example 71, the system of any of Examples 61 through 70, wherein the tissue surface is located on or within at least one of an oral cavity, an oropharynx, a hypopharynx, a trachea, or a larynx.

Example 72 comprises a system (or corresponding method) for performing depth-selective laser beam delivery, the system comprising: a scanning assembly configured to scan a surgical laser beam in two axes; an optical system configured to controllably focus the surgical laser beam in a depth-selective manner, the optical system comprising an objective to convey the surgical laser beam to a treatment site and supporting visible light visualization by establishing at least two distinct visible light visualization optical pathways from the treatment site to respective visualization imagers to provide respective visualization perspectives; and an ultrafast surgical laser source configured to generate the surgical laser beam for excising tissue, facilitating hemostasis, or both.

In Example 73, the system of Example 72, wherein the respective visualization perspectives are formed using finite conjugate optical arrangements sharing the objective.

In Example 74, the system of any of Examples 72 or 73, wherein the at least two distinct visible light visualization optical pathways include respective symmetrically-arranged peripheral regions of the objective.

In Example 75, the system of any of Examples 72 through 74, wherein respective collection angles associated with the at least two distinct visible light visualization optical pathways are controlled using respective stops.

In Example 76, the system of any of Examples 72 through 75, wherein the optical system is configured to controllably co-focus the surgical laser beam and an optical coherence tomography (OCT) beam in a depth-selective manner, the objective conveying the surgical laser beam and the OCT beam to the treatment site; wherein the surgical laser beam comprises monochromatic coherent pulsed light; and wherein the OCT beam comprises incoherent polychromatic light or coherent laser light having a varying wavelength.

In Example 77, the system of Example 76, wherein the scanning assembly is configured to co-scan the surgical laser beam and the OCT beam.

In Example 78, the system of any of Examples 72 through 77, wherein the surgical laser source is configured to generate ultrafast pulses defined by having a duration from a range of 10 femtoseconds to 300 picoseconds.

In Example 79, the system of any of Examples 72 through 78, wherein the control system is configured to control the optical system to controllably focus the surgical laser beam at one or more specified depths to perform tissue excision without requiring excision or damage of tissue at depths other than the specified depth along a direction from which the surgical laser beam is delivered.

In Example 80, the system of Example 79, wherein the one or more specified depths comprises a sub-surface depth beneath a tissue surface at the treatment site.

In Example 81, the system of any of Examples 79 or 80, wherein an initial depth of excision is sub-surface.

In Example 82, the system of any of Examples 72 through 81, wherein the control system is configured to control the optical system to excise tissue to establish at least one vent or port to a sub-surface region beneath a tissue surface at the treatment site.

In Example 83, the system of any of Examples 72 through 82, wherein the treatment site is located on or within at least one of an oral cavity, an oropharynx, a hypopharynx, a trachea, or a larynx.

Example 84 comprises a machine-implemented method for performing depth-selective trans-oral surgical laser beam delivery using a system comprising a scanning assembly, an optical system, and a control system, the method comprising: co-scanning respective beams in two axes using the scanning assembly, the respective beams comprising a surgical laser beam comprising monochromatic coherent pulsed light, an optical coherence tomography (OCT) beam comprising incoherent polychromatic light or coherent laser light having a varying wavelength; controllably co-focusing the respective beams and supporting visible light visualization using the optical system; generating a presentation of a visible-light visualization of a tissue surface; receiving an input defining a two-dimensional treatment area, in response to a presentation of a visible-light visualization of the tissue surface; generating a presentation of a cross-sectional representation of a region below the tissue surface, the cross-sectional representation constructed using a scattered representation of the OCT beam conveyed by the optical system; receiving an input defining a depth range for treatment by the surgical laser beam, in response to the presentation of the cross-sectional representation of the region below the tissue surface; and generating control data defining cycles to modify and visualize tissue within a volume defined by the two-dimensional treatment area and the depth range, by actuating the optical system to focus on respective focal planes corresponding to different depths, and at respective depths, actuating the scanning assembly to scan the surgical laser beam and OCT beam across the two-dimensional area including delivering the surgical laser beam and OCT beam trans-orally.

In Example 85, the machine-implemented method of Example 84, wherein the treatment area is located on or within false or true vocal fold tissue.

In Example 86, the machine-implemented method of Example 84, wherein the treatment area is located on or within a larynx.

In Example 87, the machine-implemented method of Example 84, wherein the treatment area is located on or within at least one of an oral cavity, an oropharynx, a hypopharynx, or a trachea.

Example 88 comprises a machine-implemented method for performing depth-selective surgical laser beam delivery using a system comprising a scanning assembly, an optical system, an ultrafast surgical laser source, and a control system, the method comprising: generating the surgical laser beam for excising tissue, facilitating hemostasis, or both, using the ultrafast surgical laser source; scanning the surgical laser beam in two axes using the scanning assembly; and controllably focusing the surgical laser beam in a depth-selective manner using the optical system, the optical system comprising an objective to convey the surgical laser beam to a treatment site and supporting visible light visualization by establishing at least two distinct visible light visualization optical pathways from the treatment site to respective visualization imagers to provide respective visualization perspectives.

In Example 89, the machine-implemented method of Example 88, wherein the treatment site is located on or within false or true vocal fold tissue.

In Example 90, the machine-implemented method of Example 88, wherein the treatment site is located on or within a larynx.

In Example 91, the machine-implemented method of Example 88, wherein the treatment site is located on or within at least one of an oral cavity, an oropharynx, a hypopharynx, or a trachea.

The above detailed description includes references to the accompanying drawings, which form a part of the detailed description. The drawings show, by way of illustration, specific embodiments in which the invention can be practiced. These embodiments are also referred to generally as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc., are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Such instructions can be read and executed by one or more processors to enable performance of operations comprising a method, for example. The instructions are in any suitable form, such as but not limited to source code, compiled code, interpreted code, executable code, static code, dynamic code, and the like. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for performing depth-selective trans-oral laser beam delivery, the system comprising:
    a scanning assembly configured to co-scan respective beams in two axes, the respective beams comprising a surgical laser beam comprising monochromatic coherent pulsed light, an optical coherence tomography (OCT) beam comprising incoherent polychromatic light or coherent laser light having a varying wavelength, and a visible aiming beam;
    an optical system configured to controllably co-focus the respective beams including at least two visible aiming beam portions, including directing the at least two visible aiming beam portions trans-orally toward a tissue surface and conveying reflections of the visible aiming beam portions to a visualization imager; and
    a control system configured to:
        generate a presentation of a visible-light visualization of a tissue surface and the reflections of the visible aiming beam portions received by the visualization imager;
        acquire focus on the tissue surface as indicated by the respective visible aiming beam portions spatially converging in the generated presentation, by varying a focus of the optical system; and
        track motion in two axes using a visible feature in an in-focus generated presentation, for control of the scanning assembly.

2. The system of claim 1, wherein the optical system comprises an objective to convey the surgical laser beam to a treatment site and supporting visible light visualization by establishing at least two distinct visible light visualization optical pathways from the treatment site to respective visualization imagers to provide respective visualization perspectives.

3. The system of claim 1, comprising an ultrafast surgical laser source configured generate ultrafast pulses defined by having a duration from 10 femtoseconds to 300 picoseconds to generate the surgical laser beam for excising tissue, facilitating hemostasis, or both.

4. The system of claim 1, wherein the control system is configured to identify a candidate visible location for tracking, comprising an anatomical or artificial landmark; and
wherein the visible feature is indicated graphically in the generated presentation.

5. The system of claim 1, wherein the control system is configured to:
receive an input defining a two-dimensional treatment area, in response to a presentation of a visible-light visualization of the tissue surface; and
generate control data for actuating the scanning assembly to compensate for the tracked motion to scan the surgical laser beam across the two-dimensional treatment area.

6. The system of claim 5, wherein the control system is configured to:
generate a presentation of a cross-sectional representation of a region below the tissue surface, the cross-sectional representation constructed using a scattered representation of the OCT beam conveyed by the optical system; and
receive an input defining a depth range for treatment by the surgical laser beam, in response to the presentation of the cross-sectional representation of the region below the tissue surface.

7. The system of claim 6, wherein the control system is configured to contemporaneously present the visible light visualization and the cross-sectional representation to a user.

8. The system of claim 6, wherein the control system, in response to the received inputs defining the two-dimensional treatment area and the depth range for treatment, is configured to generate control data defining cycles to modify and visualize tissue within a volume defined by the two-dimensional treatment area and the depth range, by actuating the optical system to focus on respective focal planes corresponding to different depths, and at respective depths, actuating the scanning assembly to scan the surgical laser beam and OCT beam across the two-dimensional area.

9. The system of claim 6, wherein the control system is configured to:
track motion in a third axis corresponding to a depth axis, using a feature in the cross-sectional representation; and
generate control data for actuating the optical system to focus on respective focal planes corresponding to different depths including compensating for tracked motion in the third axis.

10. The system of claim 6, wherein the cross-sectional representation of the region below the tissue surface shows regions in the cross-sectional representation corresponding to different tissue characteristics.

11. The system of claim 1, wherein the tissue surface is located on or within false or true vocal fold tissue.

12. The system of claim 1, wherein the tissue surface is located on or within a larynx.

13. The system of claim 1, wherein the tissue surface is located on or within at least one of an oral cavity, an oropharynx, a hypopharynx, or a trachea.

14. The system of claim 1, wherein the optical system is configured to establish the at least two aiming beam portions including splitting an aiming beam into the at least two portions and directing the at least two aiming beam portions to converge with each other at a specified focal location.

15. A system for performing depth-selective trans-oral laser beam delivery, the system comprising:
a scanning assembly configured to co-scan respective beams in two axes to define a first addressable region, the respective beams comprising a surgical laser beam comprising monochromatic coherent pulsed light, and an optical coherence tomography (OCT) beam comprising incoherent polychromatic light or coherent laser light having a varying wavelength;
an optical system configured to controllably co-focus the respective beams in a depth-selective manner;
a movable platform comprising electrically-operated actuators configured to adjust an orientation of the scanning assembly and optical system to move the first addressable region within a larger second addressable region; and
a control system configured to:
control the movable platform using the electrically-operated actuators platform to align the first addressable region with a tissue region of interest; and
generate control data for actuating the optical system to direct the respective beams trans-orally including focusing the surgical laser beam at respective focal planes corresponding to different depths, and at respective depths, actuating the scanning assembly to scan the surgical laser beam across a specified two-dimensional treatment area to excise tissue using at least one of plasma-induced ablation or photodisruption.

16. The system of claim 15, wherein the optical system comprises an objective to convey the surgical laser beam to a treatment site and supporting visible light visualization by establishing at least two distinct visible light visualization optical pathways from the treatment site to respective visualization imagers to provide respective visualization perspectives.

17. The system of claim 15, comprising an ultrafast surgical laser source configured to generate the surgical laser beam for excising tissue, facilitating hemostasis, or both.

18. The system of claim 17, wherein the ultrafast surgical laser source is configured to generate ultrafast pulses defined by having a duration from 10 femtosecond to 300 picoseconds.

19. The system of claim 15, wherein the movable platform is configured to adjust the orientation with at least two degrees of freedom comprising rotation in a pitch direction and rotation in a yaw direction, respectively.

20. The system of claim 15, wherein the respective beams comprise a visible aiming beam, the visible aiming beam comprising at least two aiming beam portions oriented symmetrically about a central axis.

21. The system of claim 15, wherein the control system is configured to: generate a presentation of a cross-sectional representation of a region below a tissue surface, the cross-sectional representation constructed using a scattered representation of the OCT beam conveyed by the optical system; and
receive an input defining a depth range for treatment by the surgical laser beam, in response to the presentation of the cross-sectional representation of the region below the tissue surface.

22. The system of claim 21, wherein the control system is configured to contemporaneously present a visible light visualization of the tissue surface and the cross-sectional representation of the region below the tissue surface to a user.

23. The system of claim 21, wherein the control system is configured to receive an input defining a depth range for treatment by the surgical laser beam, in response to the presentation of the cross-sectional representation of the region below the tissue surface.

24. The system of claim 23, wherein the control system, in response to the received inputs defining the two-dimensional treatment area and the depth range for treatment, is configured to generate control data defining cycles to modify and visualize tissue within a volume defined by the two-dimensional treatment area and the depth range, by actuating the optical system to focus on respective focal planes corresponding to different depths, and at respective depths, actuating the scanning assembly to scan the surgical laser beam and OCT beam across the two-dimensional area.

25. A machine-implemented method for providing depth-selective trans-oral laser beam delivery, the method comprising:
co-scanning, by a scanning assembly, respective beams in two axes, the respective beams comprising a surgical laser beam comprising monochromatic coherent pulsed light, an optical coherence tomography (OCT) beam comprising incoherent polychromatic light or coherent laser light having a varying wavelength, and a visible aiming beam;
co-focusing the respective beams including at least two visible aiming beam portions, including directing the at least two visible aiming beam portions trans-orally toward a tissue surface and conveying reflections of the visible aiming beam portions to a visualization imager;
generating a presentation of a visible-light visualization of a tissue surface and the reflections of the visible aiming beam portions received by the visualization imager;
acquiring focus on the tissue surface as indicated by the respective visible aiming beam portions spatially converging in the generated presentation, by varying a focus of an optical system; and
tracking motion in two axes using a visible feature in an in-focus generated presentation, for control of the co-scanning.

26. The machine-implemented method of claim 25, wherein the co-scanning and co-focusing include directing the respective beams trans-orally toward the tissue surface on or within at least one of an oral cavity, an oropharynx, a hypopharynx, a larynx, or a trachea.

27. The machine-implemented method of claim 25, wherein the co-scanning and co-focusing include directing the respective beams trans-orally toward the tissue surface located on or within a larynx corresponding to an epiglottis, a glottis, a sub-glottis, false or true vocal folds, muscle, cartilage, ligament, or bone.

28. The machine-implemented method of claim 25, comprising:
generating ultrafast pulses defined by having a duration from 10 femtosecond to 300 picoseconds to modify a volume of tissue; and
visualizing the tissue by presentation of a cross-sectional representation of a region below the tissue surface, the cross-sectional representation constructed using a scattered representation of the OCT beam conveyed by the optical system showing different tissue morphology of a larynx comprising one or more of epithelium, basement membrane, or lamina propria defined by superficial, middle, or deep layers, or muscle.

29. A machine-implemented method for performing depth-selective trans-oral laser beam delivery, the method comprising:
co-scanning, by a scanning assembly, respective beams in two axes to define a first addressable region, the respective beams comprising a surgical laser beam comprising monochromatic coherent pulsed light, and an optical coherence tomography (OCT) beam comprising incoherent polychromatic light or coherent laser light having a varying wavelength;
controllably co-focusing, by an optical system, the respective beams in a depth-selective manner;
adjusting, by electrically-operated actuators of a movable platform, an orientation of the scanning assembly and optical system to move the first addressable region within a larger second addressable region, including controlling the movable platform using the electrically-operated actuators to align the first addressable region with a tissue region of interest; and
generating control data for actuating the optical system to direct the respective beams trans-orally including focusing the surgical laser beam at respective focal planes corresponding to different depths, and at respective depths, actuating the scanning assembly to scan the surgical laser beam across a specified two-dimensional treatment area to excise tissue using at least one of plasma-induced ablation or photodisruption.

30. The machine-implemented method of claim 29, wherein adjusting the orientation with at least two degrees of freedom comprises rotation about two axes to shift the first addressable region; and wherein the method comprises:
modifying a laryngeal tissue volume within the first addressable region using the surgical laser beam generated by an ultrafast laser source with pulses having a duration from a range of 10 femtoseconds to 300 picoseconds; and
visualizing, using a cross-sectional representation constructed using a scattered representation of the OCT beam conveyed by the optical system, a cross-sectional representation of the laryngeal tissue.

* * * * *

UNITED STATES PATENT AND TRADEMARK OFFICE
CERTIFICATE OF CORRECTION

| | | |
|---|---|---|
| PATENT NO. | : 11,903,641 B1 | Page 1 of 1 |
| APPLICATION NO. | : 18/381941 | |
| DATED | : February 20, 2024 | |
| INVENTOR(S) | : Sharma et al. | |

It is certified that error appears in the above-identified patent and that said Letters Patent is hereby corrected as shown below:

On the Title Page

In item (73), in "Assignee", in Column 1, Line 1, delete "Femto Vox" and insert --FemtoVox-- therefor On page 2, in Column 2, under "Other Publications", Lines 42-43, delete "interventionsinotorhinolaryngology - Currenttechniquesand" and insert --interventions in otorhinolaryngology - Current techniques and-- therefor In the Claims In Column 54, Line 59, in Claim 21, after "to:", insert a linebreak Signed and Sealed this
Twenty-ninth Day of April, 2025

Coke Morgan Stewart
*Acting Director of the United States Patent and Trademark Office*